US008697117B2

(12) United States Patent
Zilberman

(10) Patent No.: US 8,697,117 B2
(45) Date of Patent: Apr. 15, 2014

(54) DRUG-ELUTING FILMS

(75) Inventor: Meital Zilberman, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 9 days.

(21) Appl. No.: 13/196,050

(22) Filed: Aug. 2, 2011

(65) Prior Publication Data

US 2012/0027833 A1   Feb. 2, 2012

Related U.S. Application Data

(60) Provisional application No. 61/369,811, filed on Aug. 2, 2010.

(51) Int. Cl.
*A61F 13/00* (2006.01)
*A61K 9/70* (2006.01)

(52) U.S. Cl.
CPC .................................. *A61K 9/7007* (2013.01)
USPC ........................................................ 424/443

(58) Field of Classification Search
None
See application file for complete search history.

(56) References Cited

U.S. PATENT DOCUMENTS

| 2001/0033853 | A1* | 10/2001 | Swanbom et al. | 424/402 |
| 2005/0163812 | A1* | 7/2005 | Hoath et al. | 424/400 |
| 2005/0214330 | A1* | 9/2005 | Yamamoto et al. | 424/400 |
| 2007/0134305 | A1* | 6/2007 | Zilberman | 424/443 |
| 2009/0098183 | A1* | 4/2009 | Detamore et al. | 424/423 |

FOREIGN PATENT DOCUMENTS

| WO | WO 2007/066339 | 6/2007 |
| WO | WO 2009/150650 | 12/2009 |

OTHER PUBLICATIONS

Freitas et al. "Flow-Through Ultrasonic Emulsification Combined With Static Micromixing for Aseptic Production of Microspheres by Solvent Extraction", European Journal of Pharmaceutics and Biopharmaceutics, 61(3): 181-187, Oct. 2005.
Uson et al. "Formation of Water-in-Oil (W/O) Nano-Emulsions in a Water/Mixed Non-Ionic Surfactant/Oil Systems Prepared by a Low-Energy Emulsification Method", Colloids and Surfaces A: Physicochemical and Engineering Aspect, 250(1-3): 415-421, Dec. 10, 2004.
Whang et al. "A Novel Method to Fabricate Bioabsorbable Scaffolds", Polymer, 36(4): 837-842, 1995.
Whang et al. "Ectopic Bone Formation Via rhBMP-2 Delivery From Porous Bioabsorbable Polymer Scaffolds", Journal of Biomedical Materials Research, 42(4):491-499, Dec. 15, 1998.
Elsner et al. "Novel Biodegradable Composite Wound Dressings With Controlled Release of Antibiotics: Results of a Guinea Pig Burn Model", Burns, 37(5): 895-903, Aug. 2011.
Grinberg et al. "Highly Porous Bioresorbable Scaffolds With Controlled Release of Bioactive Agents for Tissue-Regeneration Applications", Acta Biomaterialia, 6: 1278-1287, 2010.

(Continued)

*Primary Examiner* — Bethany Barham

(57) ABSTRACT

Polymeric porous films, capable of eluding a bioactive agent when coming in contact with a physiological medium according to a pre-determined and controlled release profile suitable for particular type of drug and indication, and medical devices including the same are disclosed. Also disclosed are processes for producing the polymeric porous films by freeze-drying an inverted emulsion formulation in which the polymer's composition, the polymer's concentration, the polymer's initial molecular weight, the concentration and/or the type of a surfactant, the homogenization rate and/or the oil phase to aqueous phase ratio (O:A) are selected so as to impart a desired release profile of the bioactive agent from the polymeric film.

41 Claims, 14 Drawing Sheets
(4 of 14 Drawing Sheet(s) Filed in Color)

(56) References Cited

OTHER PUBLICATIONS

Ham et al. "Macroporous Polymer Thin Film Prepared From Temporarily Stabilized Water-in-Oil Emulsion", Journal of Physical Chemistry B, 110(28): 13959-13964, 2006.

Rachelson et al. "Highly Porous Nano- and Microstructured Films Loaded With Bioactive Agents for Biomedical Applications: Structure-Release Profile Effects", Advanced Engineering Materials, 11(8): B122-B128, 2009.

Shifrovitch et al. "Metronidazole-Loaded Bioabsorbable Films as Local Antibacterial Treatment of Infected Peridontal Pockets", Journal of Periodontology, 80(2): 330-337, Feb. 2009.

Shifrovitch et al. "Metronidazole-Loaded Bioabsorbable Films as Local Antibacterial Treatment of Infected Periodontal Pockets", Journal of Periodontology, 80(2): 330-337, Feb. 2009.

Zilberman et al. "HRP-Loaded Bioresorbable Microspheres: Effect of Copolymer Composition and Molecular Weight on Microstructure and Release Profile", Journal of Biomaterials Applications, 22(5): 391-407, Mar. 2008.

Zilberman et al. "Structured Drug-Eluting Bioresorbable Films: Microstructure and Release Profile", Journal of Biomaterials Applications, 23: 385-406, Mar. 2009.

Zilberman et al. "Structured Drug-Eluting Bioresorbable Films: Microstructure and Release Profile", Journal of Biomaterilas Applications, 23(5): 385-406, Mar. 2009.

* cited by examiner

DRUG-ELUTING FILMS

RELATED APPLICATION

This application claims the benefit of priority under 35 USC 119(e) of U.S. Provisional Patent Application No. 61/369,811 filed Aug. 2, 2011.

FIELD AND BACKGROUND OF THE INVENTION

The present invention, in some embodiments thereof, relates to polymeric systems and, more particularly, but not exclusively, to polymeric systems loaded with a bioactive agent, which are designed so as to controllably release the bioactive agent.

Drug-eluting medical devices have become increasingly in demand in the last decade. Drug-eluting medical devices for topical administration, such as skin patches and wound dressing, are commonly used for systemic and local drug delivery, various skin treatments and tissue regeneration. Implantable drug-eluding devices are used to deliver a drug to a target organ or bodily site in fields such as cardiology, tissue regeneration, pain management and cancer treatment.

Drug-delivery systems have been developed over the years for uses in various applications, including topical and systemic treatments. Controlled drug delivery applications include both sustained delivery over days/weeks/months/years and targeted (e.g., to an infected wound, an exposed tissue, a damaged tissue, a tumor, a diseased blood vessel, etc.) delivery on a "one-time" or sustained basis. Controlled release formulations can be used to reduce the amount of drug necessary to cause the same therapeutic effect in patients. The convenience of fewer and more effective doses also increases patient compliance. Over the years of controlled release research, different systems, ranging from coated tablets and gels to biodegradable microspheres and osmotic systems, have been explored experimentally and computationally to get pre-designed release profiles. In many of the controlled release formulations, immediately upon placement in the release medium, an initial large bolus of drug is released before the release rate reaches a stable profile. This phenomenon is typically referred to as "burst release".

Burst release may be the optimal mechanism of delivery in several instances. One of the current difficulties with burst release is that it is unpredictable, and even when the burst is desired, the amount of burst cannot be significantly controlled. It has been shown that many drugs need to be administered at varying rates, and for some drugs, such as those used at the beginning of wound treatment, an initial burst provides immediate relief followed by prolonged release to promote gradual healing. The food industry have a vested interest in the development of burst release systems where coatings are desired to protect flavors and aromas during processing and storage, but must allow rapid release when the product is consumed. Recent advances in the ability to target specific cells and organs, through either surface modification or implantation, allows the location of the delivery to be highly specific, and either burst or prolonged release may be desired at that site, after the coating has served its purpose of sequestering the drug to protect it from denaturation and first-pass metabolism. In several pulsatile delivery processes, burst release may also be a goal, so that the active agent can be delivered rapidly upon changes in environmental conditions that trigger the release.

Organ and tissue failure or loss, such as in burn wounds, trauma wounds, diabetic ulcers and pressure sores, is one of the most frequent and devastating problems in human healthcare. The skin, being the largest organ in the body, serving many different functions, still possesses some of the most difficult challenges in modern medicine. The moist, warm, and nutritious environment provided by topical wounds, together with a diminished immune function secondary to inadequate wound perfusion, may enable the build-up of physical factors such as devitalized, ischemic, hypoxic, or necrotic tissue and foreign material, all of which provide an ideal environment for bacterial growth. In burns, infection is the major complication after the initial period of shock. Drug-eluting wound dressing is one of the most advanced and effective therapeutic solutions to such medical conditions.

Presently known wound dressings are designed to maintain a moist environment to promote healing by preventing cellular dehydration and encouraging collagen synthesis and angiogenesis. Nevertheless, over-restriction of water evaporation from the wound should be avoided as accumulation of fluid under the dressing may cause maceration and sustain infection. Water vapor transmission rate (WVTR) from skin has been found to vary considerably depending on the wound type and healing stage; increasing from 204 grams per square meter per day for normal skin to 278 and as much as 5138 grams per square meter per day, for first degree burns and granulating wounds, respectively. Therefore, the physical and chemical properties of the dressing should be suited to the type of wound and importantly to the degree of exudation from it.

A range of dressing formats based on films, hydrophilic gels and foams are available or have been investigated. These include, for example, OPTSITE® (Smith&Nephew) and BIOCLUSSIVE® (Johnson & Johnson); carboxymethylcellulose-based INTRASITE GEL® (Smith&Nephew) and alginate-based TEGAGEL® (3M); and LYOFOAM® (Mölnlycke Healthcare) and ALLEVYN® (Smith&Nephew).

The partial efficacy of films and foams has encouraged the development of improved wound dressings that provide an antimicrobial effect by eluting germicidal compounds such as iodine (IODOSORB®, Smith&Nephew), chlorohexidime (BIOPATCH®, Johnson & Johnson) or most frequently silver ions (e.g. ACTICOAT® by Smith&Nephew, ACTISORB® by Johnson & Johnson and AQUACELL® by ConvaTec). Such dressings are designed to provide controlled release of the active agent through a slow sustained release mechanism which helps to avoid toxicity yet ensures delivery of a therapeutic dose to the wound.

Biodegradable film dressings made of lactide-caprolactone copolymers such as Topkin® (Biomet) and Oprafol® (Lohmann & Rauscher) have been made available. Bioresorbable dressing based on biological materials such as collagen and chitosan have been reported to perform better than conventional and synthetic dressings in accelerating granulation tissue formation and epithelialization. However, controlling the release of antibiotics from devices made from these hydrophilic materials is deficient since in most cases the drug's reservoir is depleted in less than two days, resulting in a very short antibacterial effect.

A major area of research in tissue engineering is the development of medical devices that elute bioactive agents such as growth factors, which upon placement of such device, recruit cells from the body thereto, and thus enable tissue formation therein. Typically the administration of growth factors is problematic, due to their poor in vivo stability. It is therefore necessary to develop systems with controlled delivery of bioactive agents that can achieve prolonged availability as well as protection of these bioactive agents, which may otherwise undergo rapid proteolysis.

The main obstacle to successful incorporation and delivery of small molecules, as well as proteins, from scaffolds is their inactivation during the process of scaffold manufacture due to exposure to high temperatures or harsh chemical environments. Methods that minimize protein inactivation must therefore be developed. Three approaches to protein (growth factor) incorporation into bioresorbable scaffolds have recently been presented: (i) adsorption onto the surface of the scaffold [Elcin A E, et al., *Tissue Eng* 2006, 12, p. 959-68]; (ii) composite scaffold/microsphere structures [Zhu X H, et al. *J Biomed Mater Res A*, 2009, 89(2), p. 411-23; Wei G, et al., *J Controlled Release* 2006; 112(1), p. 103-10]; and (iii) freeze-drying of inverted emulsions. The third method is briefly described below.

Emulsions are metastable colloids formed by two immiscible fluids, where one is dispersed in the other in the presence of surface-active agents (surfactants) [Bibette J.; *Emulsion Science: Basic Principles: an overview*; Berlin, Springer Verlag; 2002, chp. 5-6]. Inverted emulsions are composed of water droplets dispersed in a continuous oil (organic) phase. Emulsions are obtained by shearing two immiscible fluids, leading to the fragmentation of one phase into the other. They are metastable and their lifetime may vary considerably depending on the temperature and their composition. The instability is due to the large interfacial area, which results in a large surface energy that is associated with finely dispersed systems [Becher P. *Encyclopedia of emulsion technology*, New York, Marcel Dekker; 1988, chp. 1-2]. The technique of freeze-drying inverted emulsions is unique in being able to preserve the liquid structure in solids. Also, it is important to note that incorporation of bioactive molecules is carried out during the scaffold-production process. This fabrication process enables the incorporation of both water-soluble and water-insoluble drugs into the film in order to obtain an "active implant" that releases drugs to the surrounding in a controlled manner. Water-soluble bioactive agents are incorporated in the aqueous phase of the inverted emulsion, whereas water-insoluble drugs are incorporated in the organic (polymer) phase. Sensitive bioactive agents, such as proteins, can also be incorporated in the aqueous phase. This prevents their exposure to harsh organic solvents and enables the preservation of their activity. Whang et al. [Whang K, et al., *Polymer*, 1995, 36(4), p. 837-42; Whang K et al., *J Biomed Mater Res*, 1998, 42(4), p. 491-9] used this method to prepare poly(DL-lactic-co-glycolic acid) (PDLGA or PLGA) scaffolds loaded with a recombinant human bone morphogenetic protein (rhBMP-2) and investigated the effect of the rhBMP-2 release in vivo using a rat model. The rhBMP-2-incorporated scaffold induced bone formation, which confirmed the preserved bioactivity of the rhBMP-2 released from the scaffold. Contact radiography, radiomorphometry, histology and histomorphometry revealed significantly more bone in the rhBMP-2 implants than in the controls.

Nanoemulsions are thermodynamically stable when the surface tension is reduced to approximately zero, or metastable in very small-scale emulsions. The literature on nanoemulsion formation refers to two main techniques: dispersion (high-energy emulsification) and condensation (low-energy emulsification). Dispersion techniques use energy input, generally from mechanical devices such as rotor-stator systems, high shear stirring, high pressure homogenizers, and ultrasound generators, whereas condensation methods use chemical energy stored in the components (usually surfactants). The small droplet size makes nanoemulsions stable against coalescence and creaming. Most publications and applications of nanoemulsions are related to the oil-in-water (O:W) type. Only a few recent publications described water-in-oil (W:O) nanoemulsions, which are also referred to in the art as inverted emulsions [N. Uson, et al., *Colloids Surf A*, 2004, 250, p. 415; S. Freitas et al., *Eur. J. Pharm. Biopharm.*, 2005, 61, p. 181; and Ham, H. T. et al., *J. Phys. Chem. B*, 2006, 110, p. 13959].

The freeze-drying of inverted emulsions technique is unique in being able to preserve the liquid structure in solids in order to produce highly porous nanostructured films that can be used as basic elements or parts of various implants and scaffolds for tissue regeneration. This fabrication process enables the incorporation of both water-soluble and water-insoluble drugs into the film in order to obtain an "active implant" that releases drugs to the surrounding in a controlled manner and therefore induces healing effects in addition to its regular role (of support, for example). Water-soluble bioactive agents are incorporated in the aqueous phase of the inverted emulsion, whereas water-insoluble drugs are incorporated in the organic (polymer) phase. Sensitive bioactive agents, such as proteins, can also be incorporated in the aqueous phase. This prevents their exposure to harsh organic solvents and enables the preservation of their activity.

The presence of surface-active agents (surfactants) is necessary for stabilizing an emulsion since they reduce the interfacial tension between the two immiscible phases. Proteins are widely used as emulsion stabilizers in the food industry [K. Whang, T. K. et al., *Biomaterials*, 2000, 21, p. 2545; Tcholakova, S. et al., *Adv. Colloid Interface Sci.*, 2006, 123, p. 259].

It has been reported that metastable W:O nanoemulsions can be stabilized by bovine serum albumin (BSA) [Sarker, D. K., *Curr. Drug Deliv.*, 2005, 2, p. 297; Whang, K. et al., *Biomaterials*, 2000, 21, p. 2545; Yang, Y. Y. et al., *Biomaterials*, 2001, 22, p. 231]. Hydrophilic polymers, such as poly (vinyl alcohol) (PVA) and poly(ethylene glycol) (PEG), act as surfactants due to their amphiphilic molecular structure, thus increasing the affinity between the aqueous and organic phases [Liu, Y. et al., *J. Control. Release* 2002, 83, 147; Castellanos, I. J. et al., *J. Pharm. Pharmacol.*, 2005, 57, p. 1261; and Delgado, A. et al., *Eur. J. Pharm. Biopharm.*, 2000, 50, p. 227].

U.S. Patent Application having Publication No. 20070134305, by the present inventor, which is incorporated by reference as if fully set forth herein, teaches composite structures, composed of a fibril core and a polymeric coat, which are capable of encapsulating both hydrophobic and hydrophilic bioactive agents while retaining the activity of these agents and favorable mechanical properties of the core fiber. These composite fibers, comprising a coat made of a freeze-dried layer of an emulsion containing a biodegradable polymer and the drug(s), can be used to construct medical devices and disposable articles.

U.S. Patent Application having Publication No. 20110091515, of which the present inventor is a co-author, which is incorporated by reference as if fully set forth herein, teaches composite structures composed of a mesh device as a core structure, being a medical device or article, and a porous polymeric coat and designed capable of encapsulating bioactive agents while retaining the activity of these agents.

The structures disclosed in U.S. Patent Applications having Publication Nos. 20070134305 and 20110091515 are useful in applications such as tissue engineering where encapsulation of biomolecules such as growth factors and cells can be effected without compromising bioactivity or mechanical strength.

Additional background art includes Zilberman, M. et al., *J. Biomater. Appl.*, 2008, 22(5), p. 391-407; Zilberman et al., *J.*

Biomater. Appl., 2009, 23(5), p. 385-406; and Shifrovitch et al., J. Periodontol, 2009, 80(2), p. 330-337.

SUMMARY OF THE INVENTION

Polymeric porous films, capable of eluding a bioactive agent when coming in contact with a physiological medium according to a pre-determined and controlled release profile suitable for particular type of drug and indication, and medical devices including the same are disclosed. Also disclosed are processes for producing the polymeric porous films by freeze-drying an inverted emulsion formulation in which the polymer's composition, the polymer's concentration, the polymer's initial molecular weight, the concentration and/or the type of a surfactant, the homogenization rate and/or the oil phase to aqueous phase ratio (O:A) are selected so as to impart a desired release profile of the bioactive agent from the polymeric film.

According to an aspect of some embodiments of the present invention, there is provided a polymeric system which includes a first polymeric porous film having incorporated therein a bioactive agent, the system being characterized by at least one of:

(a) the first polymeric porous film being prepared by freeze-drying a water-in-oil emulsion in which a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium (high burst release);

(b) the first polymeric porous film is prepared by freeze-drying a water-in-oil emulsion in which a polymer's composition, a polymer's concentration, a polymer's initial molecular weight, a concentration and/or type of a surfactant, a homogenization rate and/or an oil phase to aqueous phase ratio (O:A) are selected such that no more than 20% of the bioactive agent are released within 6 hours of contacting the system with a physiological medium (low burst release);

(c) a composite structure which includes the first polymeric porous film and which further includes a second polymeric film onto which the first polymeric porous film is applied; and (d) a mean pore diameter of the first polymeric porous film lower than 1 micron.

According to some embodiments of the invention, the system is for high burst release of the bioactive agent and is characterized by the first polymeric porous film being prepared by freeze-drying a water-in-oil emulsion in which a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium, wherein the bioactive agent is an antibiotic agent, an analgesic agent and/or a hemostatic agent.

According to some embodiments of the invention, the polymer is a hydrophobic biodegradable polymer.

According to some embodiments of the invention, the polymer is PDLGA.

According to some of these embodiments of the invention, the polymer's composition of the PDLGA is such that a lactic acid to glycolic acid ratio is lower than 60:40.

According to some of these embodiments of the invention, the concentration of the PDLGA in the emulsion is equal to or higher than 17% w/v.

According to some of these embodiments of the invention, the initial molecular weight of the PDLGA is higher than 100 kDa.

According to some of these embodiments of the invention, the emulsion includes a surfactant.

According to some of these embodiments of the invention, the surfactant is a high molecular weight amphiphilic or hydrophilic surfactant.

According to some of these embodiments of the invention, the concentration of the surfactant is higher than 3%.

According to some high burst release embodiments of the invention, the emulsion is prepared at a homogenization rate of more than 20000 rpm.

According to some of these embodiments of the invention, the oil phase to aqueous phase ratio (O:A) is lower than 5:1.

According to some of these embodiments of the invention, the system is characterized by a mean pore diameter lower than 5 μm.

According to some of these embodiments of the invention, the system is characterized by a mean pore diameter lower than 1 μm.

According to some of these embodiments of the invention, the system is characterized by a porosity higher than 86%.

According to some of these embodiments of the invention, the system is characterized by a first polymeric porous film prepared by freeze-drying a water-in-oil emulsion in which at least two of a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium.

According to some of these embodiments of the invention, the polymeric film is prepared from an emulsion in which:
  the polymer is PDLGA;
  a lactic acid to glycolic acid ratio of the PDLGA is lower than 60:40;
  a concentration of the PDLGA is higher than 17% w/v;
  an initial molecular weight of the PDLGA is higher than about 100 kDa;
  the emulsion includes a high molecular weight amphiphilic or hydrophilic surfactant;
  a concentration of the surfactant is higher than 3%;
  the emulsion is prepared at a homogenization rate of more than 20000 rpm; and
  an oil phase to aqueous phase ratio (O:A) in the emulsion is lower than 5:1.

According to some of these embodiments of the invention, the polymeric film is prepared from an emulsion in which:
  the polymer is PDLGA;
  a lactic acid to glycolic acid ratio of the PDLGA is 50:50;
  a concentration of the PDLGA is 25% w/v;
  an initial molecular weight of the PDLGA is 185 kDa;
  the emulsion includes a protein-type surfactant;
  a concentration of the surfactant is 5%;
  the emulsion is prepared at a homogenization rate of 28000 rpm; and
  an oil phase to aqueous phase ratio (O:A) in the emulsion is 4:1.

According to some of these embodiments of the invention, the system is used in the treatment of an acute infection, acute pain management and/or hemostasis.

According to some of these embodiments of the invention, the system further includes a second polymeric film onto which the first polymeric porous film is applied.

According to some of these embodiments of the invention, the system further which includes a third polymeric film applied on the first polymeric porous film.

According to some of these embodiments of the invention, the first polymeric porous film is characterized by a mean pore diameter lower than 1 μm and the second and third polymeric porous films are characterized by a mean pore diameter higher than 10 μm.

According to some embodiments of the invention, the system is for low burst release of the bioactive agent and is characterized by a first polymeric porous film prepared by freeze-drying a water-in-oil emulsion in which a polymer's composition, a polymer's concentration, a polymer's initial molecular weight, a concentration and/or type of a surfactant, a homogenization rate and/or an oil phase to aqueous phase ratio (O:A) are selected such that less than 20% of the bioactive agent are released within 6 hours of contacting the system with a physiological medium, wherein the bioactive agent is being selected from the group consisting of a proliferative agent, an anti-proliferative agent, an analgesic agent, an anti-cancer agent, a vitamins and a hormones.

According to some of these embodiments of the invention, the bioactive agent is a biomolecule.

According to some of these embodiments of the invention, the system being used in tissue engineering.

According to some of these embodiments of the invention, the polymer is a hydrophobic biodegradable polymer.

According to some of these embodiments of the invention, the polymer is PDLGA.

According to some of these embodiments of the invention, the polymer's composition of the PDLGA is such that a lactic acid to glycolic acid ratio is higher than 60:40.

According to some of these embodiments of the invention, the concentration of the PDLGA in the emulsion is equal to or lower than 17% w/v.

According to some of these embodiments of the invention, the initial molecular weight of the PDLGA is lower than 100 kDa.

According to some of these embodiments of the invention, the emulsion includes a surfactant.

According to some of these embodiments of the invention, the surfactant is a low molecular weight hydrophobic surfactant.

According to some of these embodiments of the invention, the concentration of the surfactant is less than 3%.

According to some of these embodiments of the invention, the emulsion is prepared at a homogenization rate of less than 20000 rpm.

According to some of these embodiments of the invention, the oil phase to aqueous phase ratio (O:A) is higher than 5:1.

According to some of these embodiments of the invention, the system is further characterized by a mean pore diameter higher than 1 μm.

According to some of these embodiments of the invention, the system is further characterized by a porosity lower than 86%.

According to some of these embodiments of the invention, the polymeric film is prepared from an emulsion in which:
the polymer is PDLGA;
a lactic acid to glycolic acid ratio of the PDLGA is higher than 60:40;
a concentration of the PDLGA is lower than 17% w/v;
an initial molecular weight of the PDLGA is lower than about 100 kDa;
the emulsion includes a low molecular weight hydrophobic surfactant;
a concentration of the surfactant is less than 3%;
the emulsion is prepared at a homogenization rate of less than 20000 rpm; and
an oil phase to aqueous phase ratio (O:A) in the emulsion is higher than 5:1.

According to some of these embodiments of the invention, the polymeric film is prepared from an emulsion which includes in which:
the polymer is PDLGA;
a lactic acid to glycolic acid ratio of the PDLGA is 75:25;
a concentration of the PDLGA is 15% w/v;
an initial molecular weight of the PDLGA is 50 kDa;
the emulsion is prepared at a homogenization rate of 14000 rpm; and
an oil phase to aqueous phase ratio (O:A) in the emulsion is 8:1.

According to some of these embodiments of the invention, the system is characterized by a polymeric porous film prepared by freeze-drying a water-in-oil emulsion in which at least two of a polymer's composition, a polymer's concentration, a polymer's initial molecular weight, a concentration and/or type of a surfactant, a homogenization rate and/or an oil phase to aqueous phase ratio (O:A) are selected such that less than 20% of the bioactive agent are released within 6 hours of contacting the system with a physiological medium.

According to some of these embodiments of the invention, the system is characterized by a polymeric porous film prepared by freeze-drying a water-in-oil emulsion in which a polymer's concentration, a polymer's initial molecular weight, a concentration of a surfactant and/or an oil phase to aqueous phase ratio (O:A) are selected such that less than 20% of the bioactive agent are released within 6 hours of contacting the system with a physiological medium.

According to some of these embodiments of the invention, the system is characterized by a polymeric porous film prepared by freeze-drying a water-in-oil emulsion in which at least two of a polymer's concentration, a polymer's initial molecular weight, a concentration of a surfactant and/or an oil phase to aqueous phase ratio (O:A) are selected such that less than 20% of the bioactive agent are released within 6 hours of contacting the system with a physiological medium.

According to some of these embodiments of the invention, the system is characterized by a polymeric porous film prepared by freeze-drying a water-in-oil emulsion in which at least three of a polymer's concentration, a polymer's initial molecular weight, a concentration of a surfactant and/or an oil phase to aqueous phase ratio (O:A) are selected such that less than 20% of the bioactive agent are released within 6 hours of contacting the system with a physiological medium.

According to some of these embodiments of the invention, the polymer is hydrophobic and the surfactant is a protein-type surfactant.

According to some of these embodiments of the invention, the polymer is PDLGA.

According to some of these embodiments of the invention, the concentration of the PDLGA in the emulsion is higher than 17% w/v and the concentration of the surfactant is less than 1%.

According to some of these embodiments of the invention, the initial molecular weight of the PDLGA is higher than 100 kDa and the concentration of the surfactant is less than 1%.

According to some of these embodiments of the invention, the oil phase to aqueous phase ratio (O:A) is higher than 5:1 and the concentration of the surfactant is less than 1%.

According to some of these embodiments of the invention, the concentration of the PDLGA in the emulsion is higher than 17% w/v, the oil phase to aqueous phase ratio (O:A) is higher than 5:1 and the concentration of the surfactant is less than 1%.

According to some of these embodiments of the invention, the system is further characterized by a porosity lower than 86%.

According to some of these embodiments of the invention, the system is for use in a prophylactic antimicrobial treatment, a pain relief treatment, an anti-proliferative treatment, a hormone deliver, a vitamin delivery and/or a tissue regeneration treatment.

According to some of these embodiments of the invention, the system further which includes a second polymeric film onto which the first polymeric porous film is applied.

According to some of these embodiments of the invention, the system which includes at least two polymeric porous films.

According to some embodiments of the invention, the system includes the first polymeric porous film and a second polymeric film onto which the first polymeric porous film is applied, wherein the second polymeric film includes a wettable polymer.

According to some embodiments of the invention, the wettable polymer is a wettable biodegradable polymer.

According to some embodiments of the invention, the wettable biodegradable polymer is selected from the group consisting of collagen, chitosan, cellulosic-base polymer and a polyethylene glycol.

According to some of these embodiments of the invention, the first polymeric porous film being prepared by freeze-drying a water-in-oil emulsion in which a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium.

According to some of these embodiments of the invention, the first polymeric porous film is prepared by freeze-drying a water-in-oil emulsion in which a polymer's composition, a polymer's concentration, a polymer's initial molecular weight, a concentration and/or type of a surfactant, a homogenization rate and/or an oil phase to aqueous phase ratio (O:A) are selected such that less than 20% of the bioactive agent are released within 6 hours of contacting the system with a physiological medium.

According to some embodiments of the invention, the system includes a second polymeric porous film, and the first polymeric porous film is characterized by a mean pore diameter lower than 1 μm.

According to some embodiments of the invention, the system includes a third polymeric film applied on the first polymeric porous film.

According to some embodiments of the invention, the polymer which comprises the first polymeric porous film is a hydrophobic biodegradable polymer, such as PDLGA.

According to some embodiments of the invention, the first polymeric porous film is characterized by a mean pore diameter lower than 1 μm, thus being a nanostructured porous polymeric film. In some of these embodiments of the invention, the first polymeric porous film is prepared by freeze-drying a water-in-oil emulsion which includes a polymer, the bioactive agent and a surfactant.

According to some of these embodiments of the invention, the first polymeric porous film is prepared by freeze-drying an emulsion in which a surfactant type, a surfactant concentration and/or a homogenization rate are selected such that at least 20% of the bioactive agent are released within 6 hours of contacting the system with a physiological medium.

According to some of these embodiments of the invention, the polymer is a hydrophobic biodegradable polymer.

According to some of these embodiments of the invention, the polymer is PDLGA.

According to some of these embodiments of the invention, the surfactant is a high molecular weight amphiphilic or hydrophilic surfactant.

According to some of these embodiments of the invention, the concentration of the surfactant is higher than 3%.

According to some of these embodiments of the invention, the emulsion is prepared at a homogenization rate of more than 20000 rpm.

According to some of these embodiments of the invention, the system is further characterized by a porosity higher than 80%.

According to some of these embodiments of the invention, the polymeric porous film is prepared from an emulsion in which:
the polymer is PDLGA;
the emulsion includes a high molecular weight amphiphilic or hydrophilic surfactant;
a concentration of the surfactant is higher than 3%; and
the emulsion is prepared at a homogenization rate of more than 20000 rpm.

According to some of these embodiments of the invention, the polymeric film is prepared from an emulsion in which:
the polymer is PDLGA;
a lactic acid to glycolic acid ratio of the PDLGA is 50:50;
a concentration of the PDLGA is 17% w/v;
an initial molecular weight of the PDLGA is 83 kDa;
the emulsion includes a protein-type surfactant;
a concentration of the surfactant is 5%;
the emulsion is prepared at a homogenization rate of 28000 rpm; and
an oil phase to aqueous phase ratio (O:A) in the emulsion is 4:1.

According to some embodiments of the invention, the system consists of the first polymeric porous film having the bioactive agent incorporated therein.

According to an aspect of some embodiments of the present invention, there is provided a medical device which includes any one of the polymeric systems described herein.

According to some medical device embodiments of the invention, the first polymeric porous film is being prepared by freeze-drying a water-in-oil emulsion in which a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium, such that the system is for high burst release of the bioactive agent. According to some of these embodiments, the device is selected from the group consisting of a wound dressing and a skin patch.

According to some medical device embodiments of the invention, the first polymeric porous film is prepared by freeze-drying a water-in-oil emulsion in which a polymer's composition, a polymer's concentration, a polymer's initial molecular weight, a concentration and/or type of a surfactant, a homogenization rate and/or an oil phase to aqueous phase ratio (O:A) are selected such that no more than 20% of the bioactive agent are released within 6 hours of contacting the system with a physiological medium, such that the system is for low burst release of the bioactive agent. According to some of these embodiments, the device is selected from the group consisting of a sustained release drug delivery system, a wound dressing and a skin patch, a tissue regeneration device and a directed antitumor device.

According to an aspect of some embodiments of the present invention, there is provided a process of preparing any of the polymeric systems presented herein, the process is effected by:

casting a first layer of a water-in-oil emulsion in or on a mold;

freeze-drying the first layer, thereby obtaining the first polymeric porous film; and detaching the first polymeric porous film from the mold to thereby obtain the system.

According to some embodiments of the invention, the process further includes:

prior to the detaching the first polymeric porous film, casting a second layer of a second water-in-oil emulsion on the first layer;

freeze-drying the first layer and the second layer, thereby obtaining a second polymeric porous film applied onto the first polymeric porous film; and detaching the first polymeric porous film from the mold to thereby obtain composite structure which includes the first polymeric porous film and which further includes a second polymeric porous film onto which the first polymeric porous film is applied;

or subsequent to the detaching the first polymeric porous film, casting a second layer of a second water-in-oil emulsion on the first polymeric porous film;

freeze-drying the second layer, to thereby obtain composite structure which includes the first polymeric porous film and which further includes a second polymeric porous film onto which the first polymeric porous film is applied.

According to some embodiments of the invention, the process further includes, subsequent to the detaching the first polymeric porous film, contacting the first polymeric porous film with a second water-in-oil emulsion the to thereby form a second layer of the second emulsion one side of the first polymeric porous film and a third layer of the second emulsion the other side of the first polymeric porous film;

freeze-drying the second layer and the third layer, to thereby obtain composite structure which includes the first polymeric porous film and which further includes a second polymeric porous film applied onto the first polymeric porous film and a third polymeric porous film applied onto the first polymeric porous film.

According to some embodiments of the invention, the process further includes:

prior to the detaching the first polymeric porous film, casting a second layer which includes a biodegradable and wettable polymer on the first layer;

freeze-drying the first layer and the second layer, thereby obtaining a biodegradable and wettable polymeric film applied onto the first polymeric porous film; and detaching the first polymeric porous film from the mold to thereby obtain composite structure which includes the first polymeric porous film and which further includes a biodegradable and wettable polymeric film applied onto the first polymeric porous film;

or subsequent to the detaching the first polymeric porous film, casting a second layer which includes a biodegradable and wettable polymer on the first polymeric porous film;

freeze-drying the second layer, to thereby obtain composite structure which includes the first polymeric porous film and which further includes a biodegradable and wettable polymeric film applied onto the first polymeric porous film.

Further according to some embodiments of the present invention there are provided methods utilizing the systems and/or devices described herein for the treatment of a medical condition that is treatable by the bioactive agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 1:
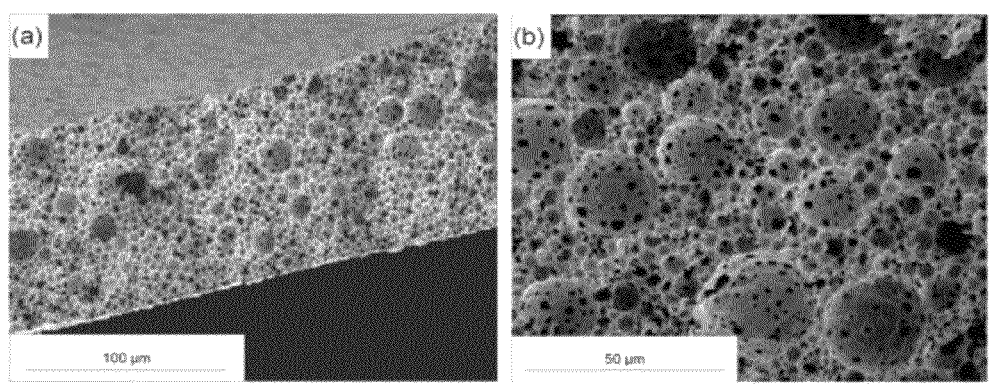
Figure 3:
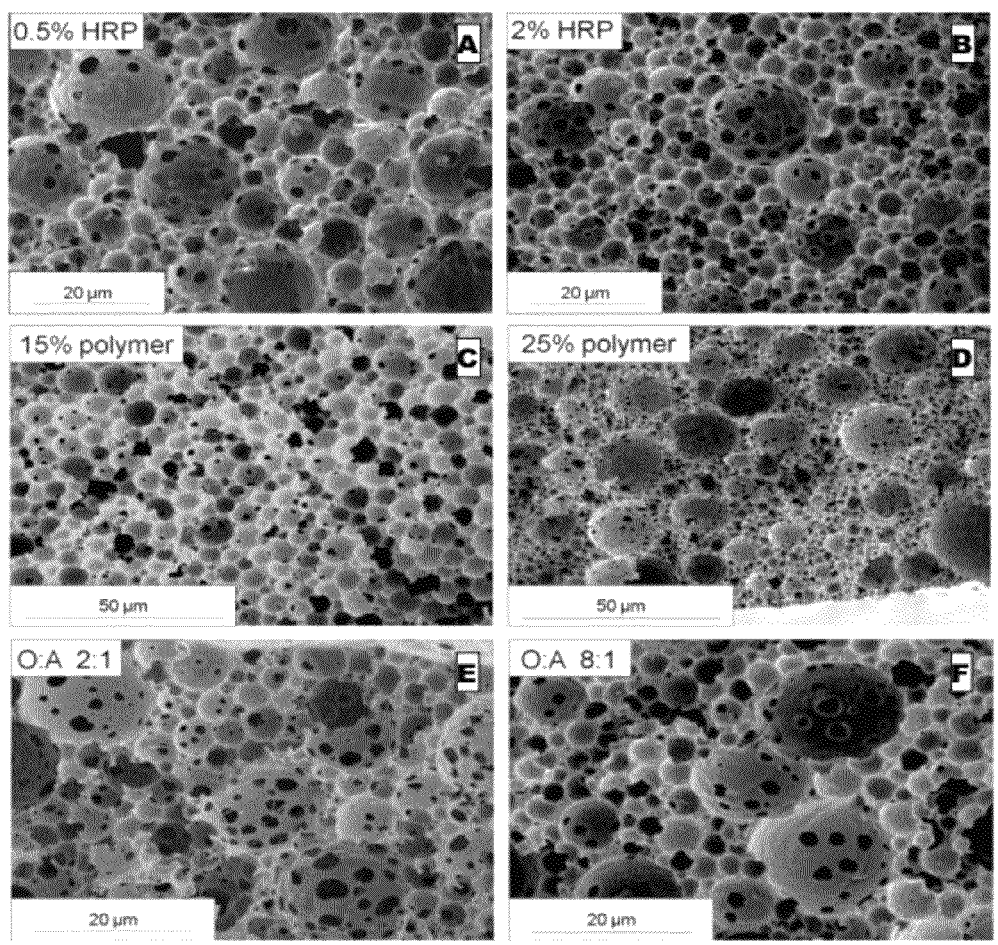
Figure 4:
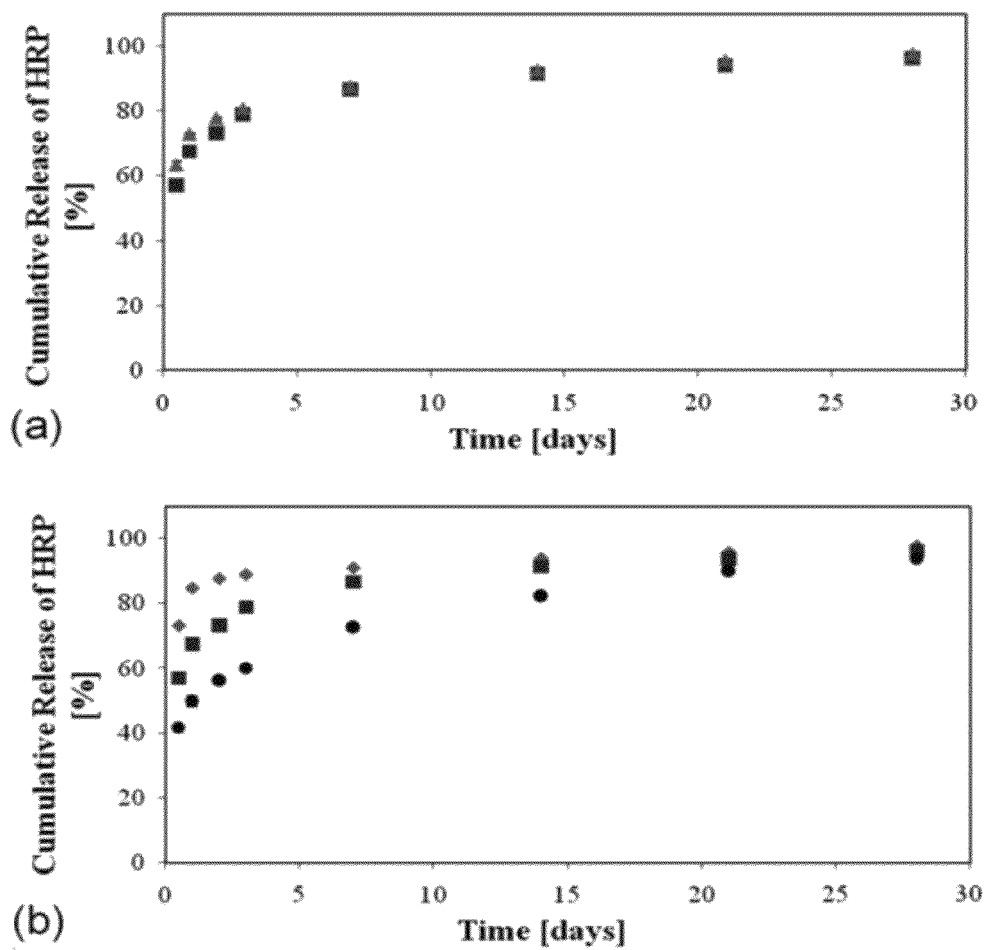
Figure 5:
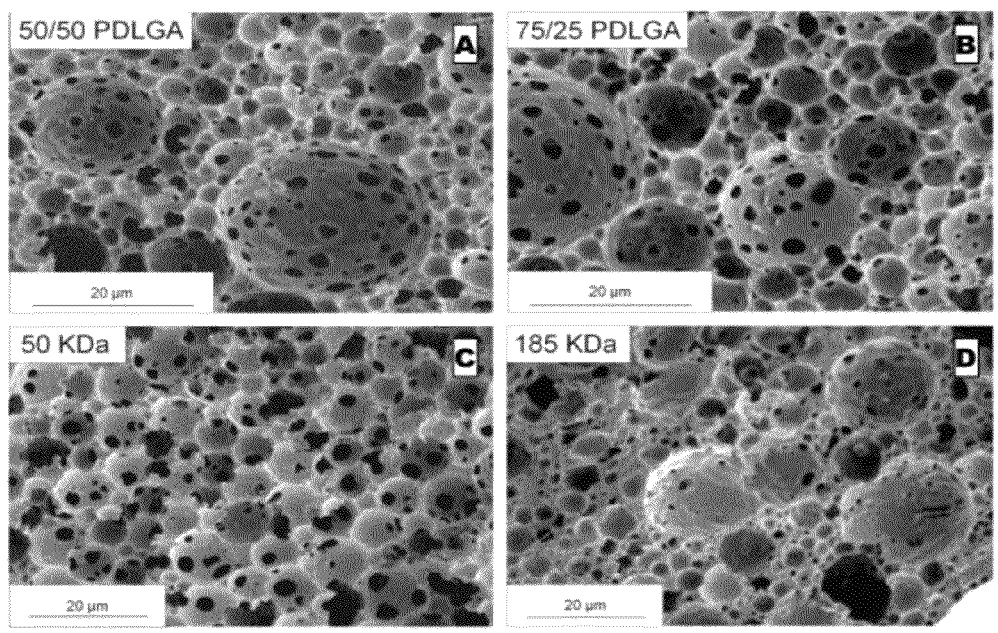
Figure 6:
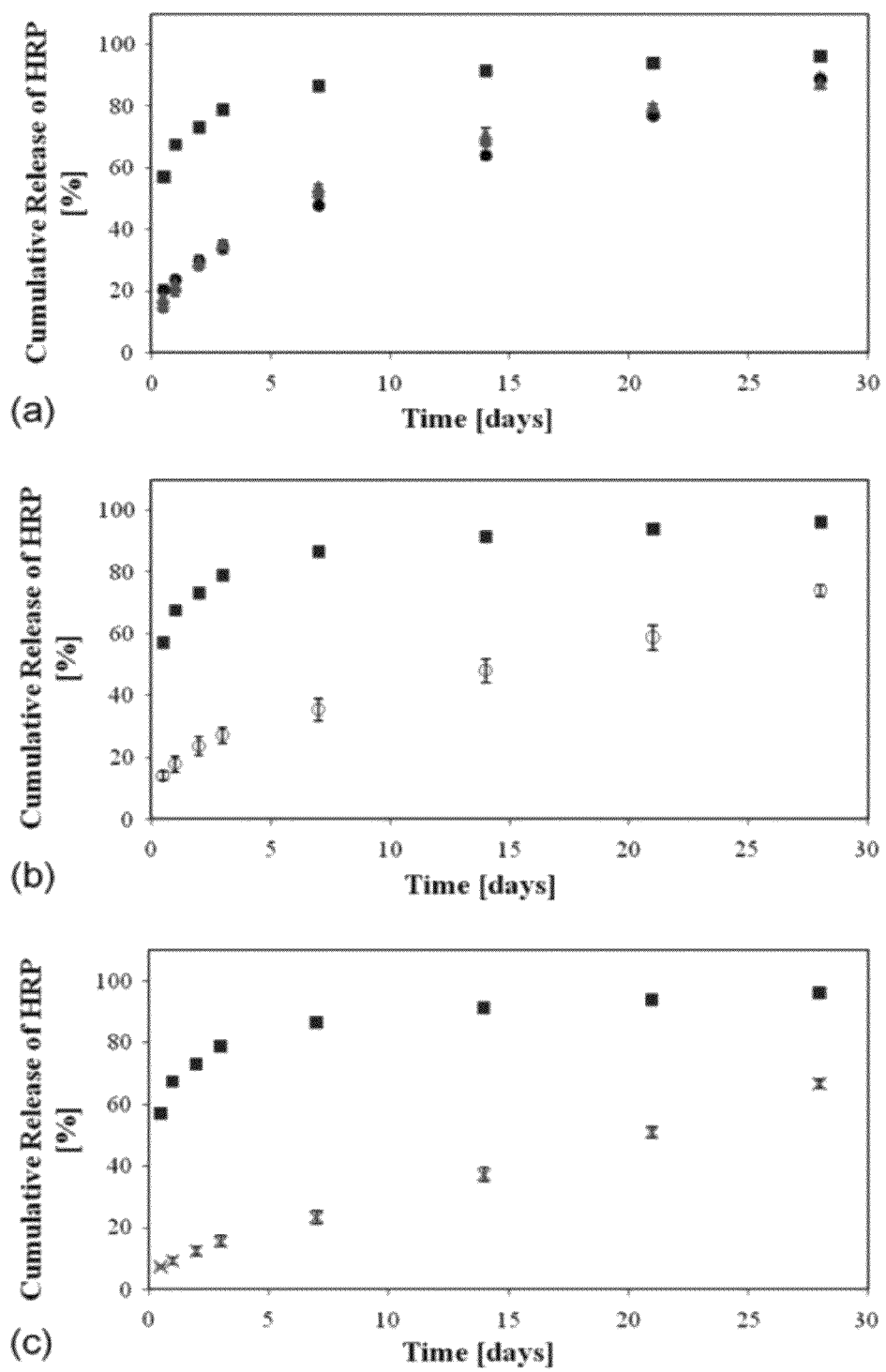
Figure 7:
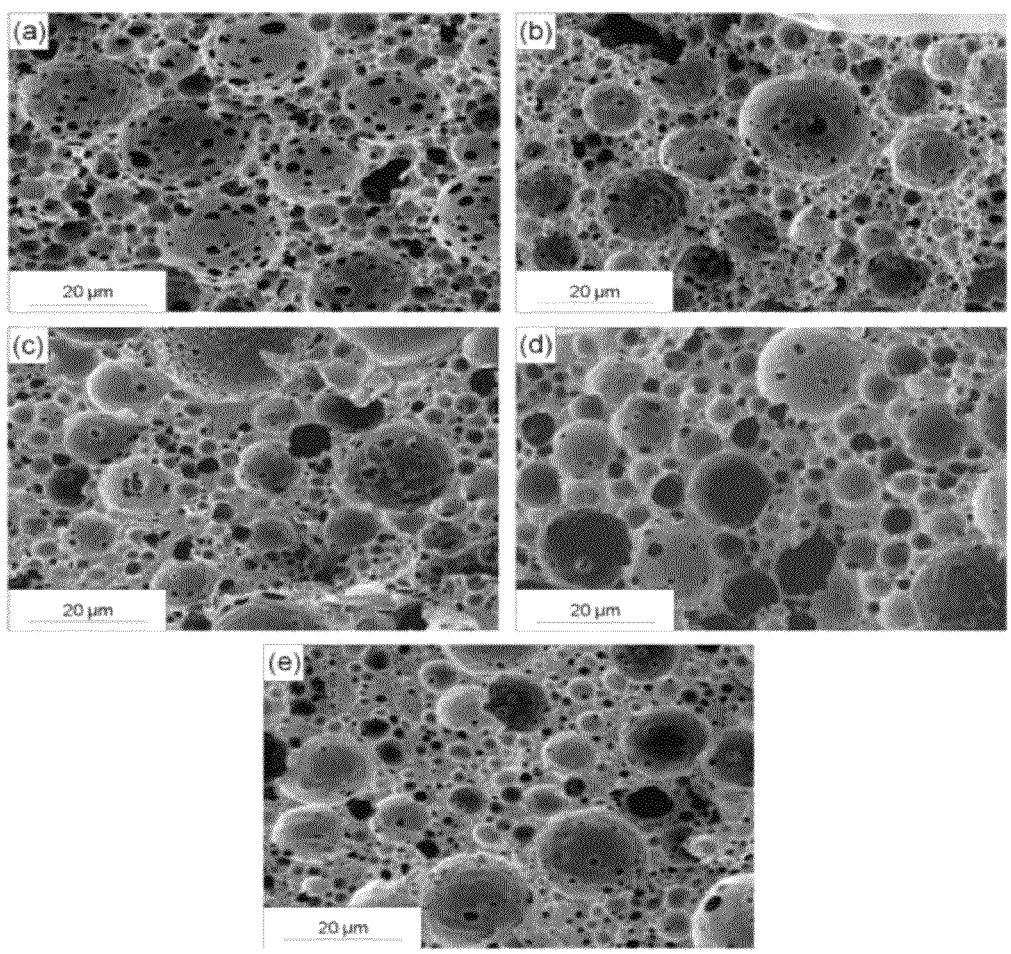
Figure 8:
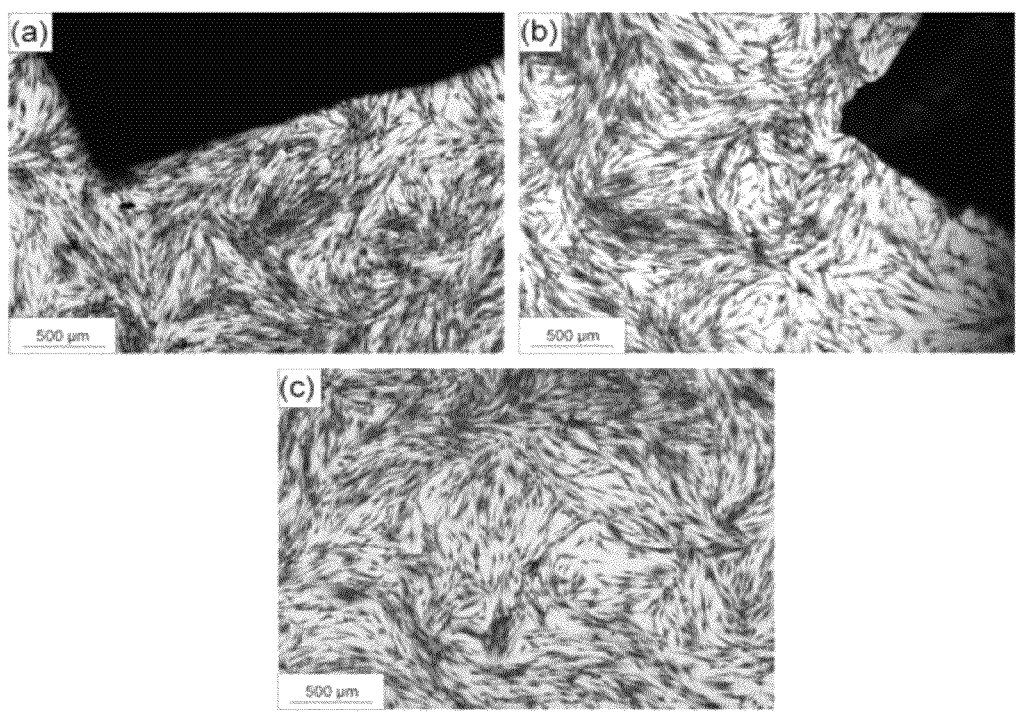
Figure 9:
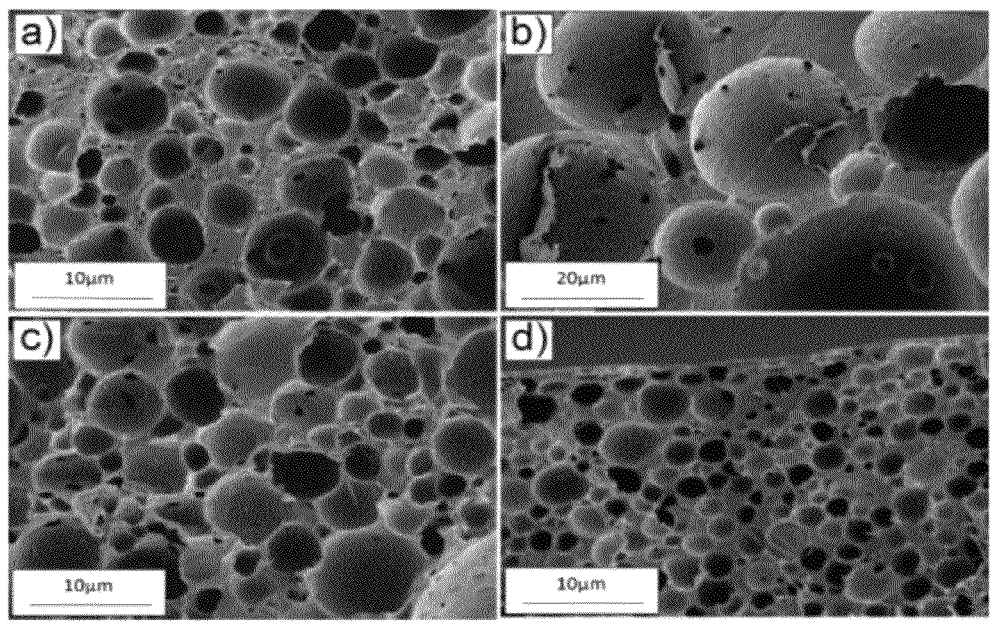
Figure 10:
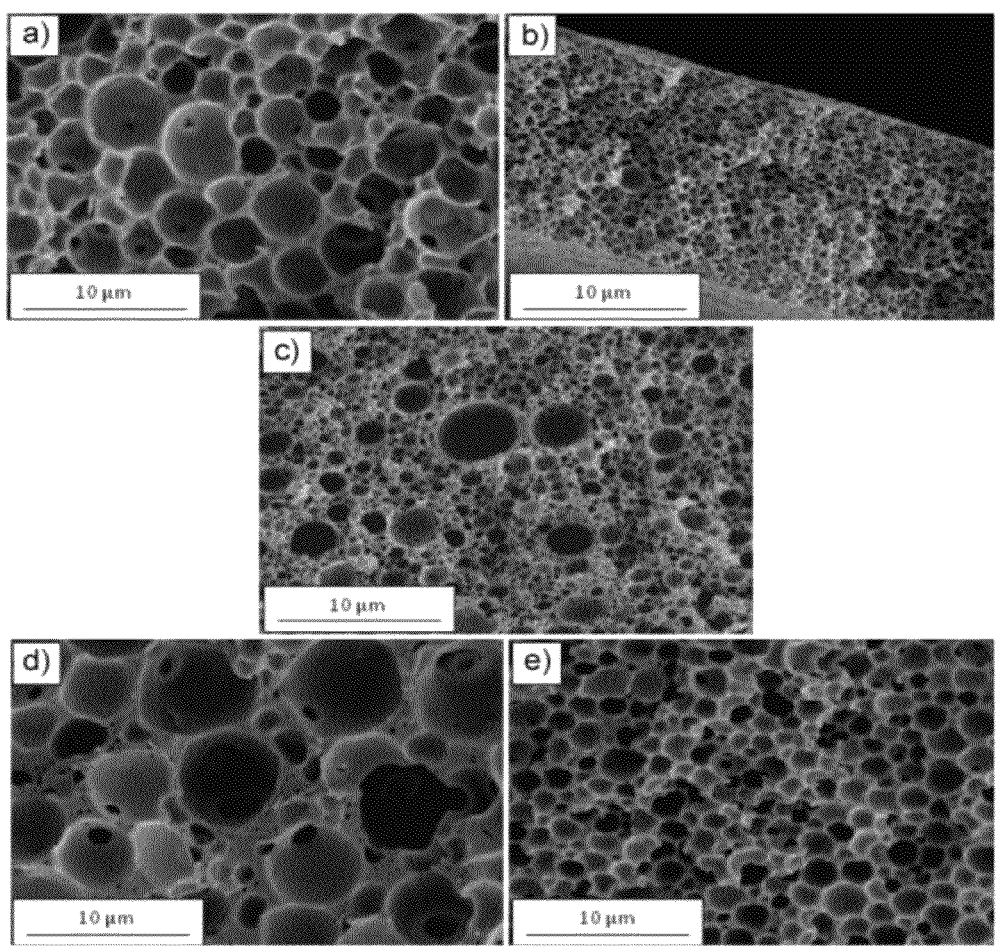
Figure 11:
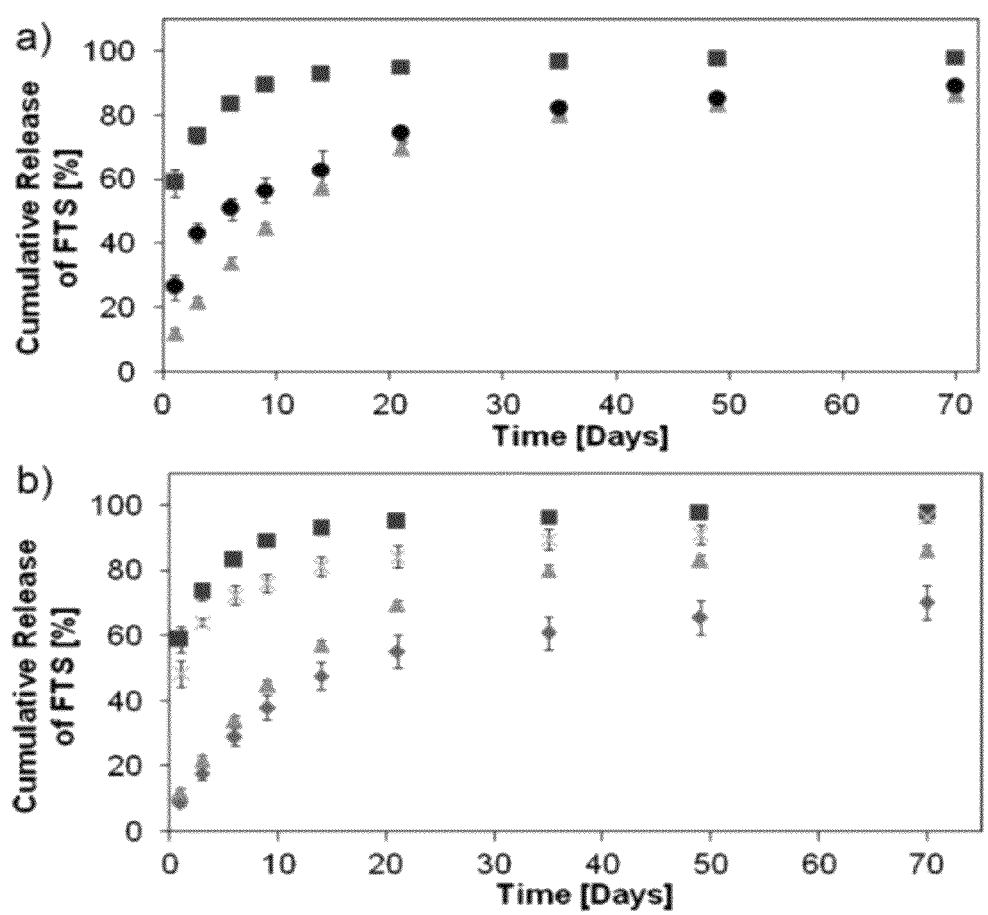
Figure 12:
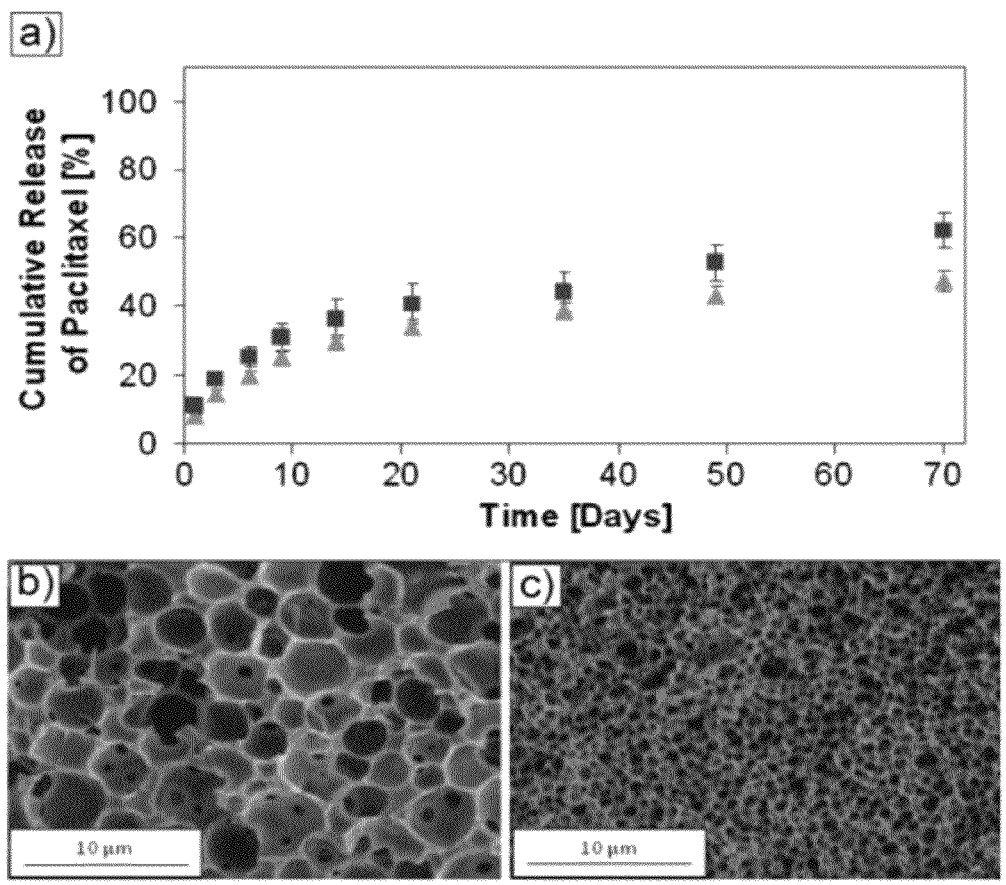

FIGS. 1A-B are SEM fractographs of a polymeric porous film, according to some embodiments of the present invention, showing a general view of a cross-section of a typical highly porous PDLGA film (low magnification, FIG. 1A), and the characteristic features of the porous structure (high magnification FIG. 1B);

FIGS. 2A-C present comparative plots of cumulative release of HRP by percents as a function of time (in days) as measured from exemplary polymeric porous films, according to some embodiments of the present invention, demonstrating the effect of a change in the emulsion's formulation parameters compared to reference formulation A, wherein FIG. 2A presents the effect of HRP concentration (solid diamonds denote 2% w/w, solid rectangles 1% w/w, and solid triangles 0.5% w/w); FIG. 2B presents the effect of polymer concentration (solid circles denote 15% w/v, solid rectangles 17.5 w/v, and green empty triangles 25% w/v); and FIG. 2C presents the effect of O:A phase ratio (empty rectangles denote 2:1 ratio, empty diamonds 6:1, and X-signs denote 8:1 ratio);

FIGS. 3A-F presents SEM fractographs of exemplary polymeric porous films, according to some embodiments of the present invention, showing the effect on the microstructure of the films as a function of a change in the emulsion formulation's parameters, wherein the effect of HRP concentration is shown in FIGS. 3A-B; the effect of polymer concentration is shown in FIGS. 3C-D; and the effect of O:A phase ratio is shown in FIGS. 3E-F, and all films are made with 17.5% w/v 50/50 PDLGA polymer having initial average MW of about 83 kDa containing 1% w/w HRP at a phase ratio of 4:1;

FIGS. 4A-B present comparative plots of cumulative release of HRP by percents as a function of time (in days) as measured from exemplary polymeric porous films, according to some embodiments of the present invention, demonstrating the effect of a change in the composition of the host copolymer compared to reference formulation A, wherein FIG. 4A presents the effect of the relative concentration of lactic and glycolic acid (solid rectangles denote 50/50 PDLGA, and solid triangles denote 75/25 PDLGA); and FIG. 4B presents the effect of the initial average molecular weight of the host polymer (solid diamonds denote 50 kDa, solid rectangles 83 kDa, and solid circles denotes 185 kDa);

FIGS. 5A-D presents SEM fractographs of exemplary polymeric porous films, according to some embodiments of the present invention, showing the effect on the microstructure of the films as a function of a change in the host copolymer composition parameters, wherein the effect of the relative content of lactic and glycolic acid is shown in FIGS. 5A-B; and the effect of the initial average molecular weight of the host polymer is shown in FIGS. 5C-D, and all films are made with 17.5% w/v containing 1% w/w HRP at a phase ratio of 4:1;

FIGS. 6A-C present comparative plots of cumulative release of HRP by percents as a function of time (in days) as measured from exemplary polymeric porous films, according to some embodiments of the present invention, demonstrating the effect of combined changes in the emulsion's formulation parameters compared to reference formulation A (marked by solid rectangles and having 17.5% w/v polymer, initial MW of 83 kDa, 1% w/w HRP and O:A=4:1), wherein FIG. 6A presents the effect of varying both the HRP concentration to 0.5% w/w HRP and varying the polymer concentration to 25% w/v (marked by solid diamonds), varying the initial MW to 185 kDa (marked by solid circles) and varying the O:A ratio to 8:1 (marked by solid triangles); FIG. 6B presents the effect of varying three parameters (0.5% w/w HRP, 25% w/v polymer, and O:A=8:1, marked by empty circles); and FIG. 6C presents the release profile from an exemplary composite "sandwich" film composed of a porous inner 50/50 PDLGA film (25% w/v polymer, MW of about 83 kDa, O:A=8:1 and 0.5% w/w HRP) and two external PDLLA layers (17.5% w/v polymer, MW of about 80 kDa, O:A=2:1, no HRP), marked by X-signs;

FIGS. 7A-E presents SEM fractographs of exemplary polymeric porous films, according to some embodiments of the present invention, showing the effect on the microstructure of the films as a function of a simultaneous change in several of the emulsion formulation's parameters, wherein FIG. 7A shown the microstructure of a film prepared from reference formulation A (50/50 PDLGA, 17.5% w/v polymer, MW=83 kDa, 1% w/w HRP, and O:A=4:1), FIG. 7B shown the microstructure of a formulation altered by 25% w/v polymer and 0.5% w/w HRP concentration, FIG. 7C shown the microstructure of a formulation altered by MW=185 kDa and 0.5% w/w HRP, FIG. 7D shown the microstructure of a formulation altered by O:A=8:1 and 0.5% w/w HRP, and FIG. 7E shown the microstructure of a formulation altered by 25% w/v polymer, O:A=8:1 and 0.5% w/w HRP;

FIGS. 8A-C present micrographs of human gingival fibroblasts in culture, showing environmental effects coffered by the presence of a polymeric porous film, according to some embodiments of the present invention, made from reference formulation A having 1% w/w HRP (FIG. 8A); (b) a film made from reference formulation A without HRP (FIG. 8B); and a control experiment with no film in the environment of the sample (FIG. 8C, films appear in FIGS. 8A-B as a shadow);

FIGS. 9A-D present SEM fractographs of polymeric porous films, according to some embodiments of the present invention, showing the effect of changes in certain formulation parameters on the structure, wherein FIG. 9A presents the film obtained from reference formulation B (17.5% w/v of 50:50 PDLGA copolymer, O:A phase ratio of 8:1 and homogenization rate of 16000 rpm), FIG. 9B presents the film obtained from copolymer modified to PDLLA, FIG. 9C presents the film obtained from a formulation modified to O:A ratio of 4:1, and FIG. 9D presents the film obtained from modified reference formulation B homogenized at a rate of 28000 rpm;

FIGS. 10A-E present SEM fractographs of FTS-loaded polymeric porous films, according to some embodiments of the present invention, showing the effect of surfactants on the structure, wherein FIG. 10A presents the film obtained from reference formulation B (17.5% w/v of 50:50 PDLGA copolymer, O:A phase ratio of 4:1 and homogenization rate of 28000 rpm) with 1.42% w/w FTS and no surfactant, FIG. 10B presents the film obtained from an emulsion similar to that presented in FIG. 10A but having 5% w/v BSA, FIG. 10C presents the film obtained from an emulsion similar to that presented in FIG. 10A but having 5% w/v HRP, FIG. 10D presents the film obtained from an emulsion similar to that presented in FIG. 10A but homogenized at a rate of 14000 rpm, and FIG. 10E presents the film obtained from an emulsion similar to that presented in FIG. 10A but having 5% w/v BSA and homogenized at a rate of 14000 rpm;

FIGS. 11A-B present comparative plots of cumulative release of FTS by percents as a function of time (in days) as measured from exemplary 50:50 PDLGA polymeric porous films, according to some embodiments of the present invention, demonstrating the effect of surfactant incorporation in the emulsion's formulation (FIG. 11A) and the effect of homogenization rate and BSA as surfactant (FIG. 11B), wherein triangles denote reference formulation B without surfactant and homogenized at 28000 rpm, rectangles denote the same with 5% w/v BSA, circles denote the same with 5% w/v HRP, diamonds denote the same without surfactant and homogenized at 14000 rpm, and X-signs denote the same with 5% w/v BSA and homogenized at 14000 rpm;

FIGS. 12A-C present a comparative plot of the release profile of paclitaxel polymeric porous films, wherein triangles denote films made from reference formulation B containing 1.42% w/w paclitaxel, and homogenized at 28000 rpm with no surfactant, and rectangles denote the same but with 5% w/v BSA (FIG. 12A), and present SEM fractographs of a film made from reference formulation B containing 1.42% w/w paclitaxel with no surfactant (FIG. 12B), and a SEM fractographs of the same but with 5% w/v BSA;

FIGS. 13A-B present comparative antibiotic drug-release plots, showing the effect of BSA as surfactant and homogenization rate on the release profile from polymeric porous films containing 17.5% w/v 50:50 PDLGA polymer, O:A=6:1, 2% w/v drug concentration, and homogenized at 28000 rpm, wherein results obtained for films loaded with mafenide acetate are shown in FIG. 13A, and results obtained for films loaded with ceftazidime pentahydrate are shown in FIG. 13B, whereas triangles denote a reference sample with no surfactant, diamonds denote the same homogenized at 14000 rpm, rectangles denote the same with 1% w/v BSA, and circles denote the same with 1% w/v BSA homogenized at 14000 rpm; and FIGS. 14A-D present SEM fractographs showing the effects of BSA as surfactant and homogenization rate on the microstructure of films made from an emulsion formulation containing 17.5% w/v 50:50 PDLGA polymer, O:A=6:1, 2% w/v mafenide acetate, and homogenized at 28000 rpm with no surfactant (FIG. 14A), the same with 1% w/v BSA (FIG.

14B), the same homogenized at 14000 rpm (FIG. 14C), and the same with 1% w/v BSA homogenized at 14000 rpm (FIG. 14D).

DESCRIPTION OF SPECIFIC EMBODIMENTS OF THE INVENTION

The present invention, in some embodiments thereof, relates to polymeric systems and, more particularly, but not exclusively, to polymeric systems loaded with a bioactive agent, which are designed so as to controllably release the bioactive agent.

As discussed supra, U.S. Patent Applications having Publication Nos. 20070134305 and 20110091515, by the present inventor, teach core structures (fibers and meshes) coated by a drug-eluding layer. The teachings of U.S. Patent Applications having Publication Nos. 20070134305 and 20110091515 are excluded from the scope of the present invention.

Most of the presently available drug-eluting medical devices lack in one or more of a list of desirable properties, which include: the capacity to encapsulate and release a (sensitive) drug, a capacity for a pre-determined and controllable drug-release, and the capacity to be bioresorbable or degradable, thereby avoiding the need to remove them from the sensitive treated site.

While conceiving the present invention, it was envisioned that a medical device which can be applied directly to a tissue (e.g., skin tissue) of a subject to occlude the treated area from the environment (e.g., for protection against infections and for moisture preservation), while at the same time elude a needed drug at a pre-determined release profile, and then biodegrade without the need to remove it from the (sensitive) treated tissue, would solve the problems still existing in presently available drug-eluting medical devices.

In an effort to improve presently available medical devices for local or systemic delivery of bioactive agents (drugs) and/or for topical treatment of a medical condition, the present inventor has developed highly porous polymeric films which can be produced by freeze-drying inverted emulsions. The technique of freeze-drying inverted emulsions is highly suitable for the preparation of films loaded with sensitive bioactive agents such as proteins, where loading is performed during the film preparation without losing the protein's activity.

The present inventor has surprisingly uncovered that by manipulating one or more of the emulsion's formulation parameters and host polymer's characteristics, the film's microstructure and the resulting drug-release profile can be finely controlled, even in a synergistic manner.

More specifically, while recognizing the deficiencies in using hydrophilic polymers for controlled release of drugs, which include excessive burst release of the drug load sequestered therein as discussed supra, and recognizing the deficiencies in using hydrophobic polymers for controlled release of drugs, which include insufficient release of the sequestered drug due to low wettability and insolubility thereof, and further recognizing the potential limitations in using highly porous hydrophobic polymers, which may yet again exhibit excessive burst release due to their enormous surface area, the present inventor has devised and practiced a systematic method for forming highly porous emulsion-born hydrophobic polymers which allow fine tuning of the drug release profile so as to provide high or low burst release suitable for any specific application, and particularly highly porous polymeric systems exhibiting low burst release which are especially suitable for applications which require sustained presence of the drug during a prolonged treatments.

The term "hydrophobic", as used herein, refers to a trait of a molecule or part of a molecule which is non-polar and is therefore immiscible with charged and polar molecules, and has a substantially higher dissolvability in non-polar solvents as compared with their dissolvability in water and other polar solvents. The phrase "dissolvability" refers to either complete dissolution of the substance in these solvents or to cases where the substance reaches its maximal saturation concentration in non-polar solvents, and the remainder of the substance is in the form of a suspension of small solid particles in the solvent. When in water, hydrophobic molecules often cluster together to form lumps, agglomerates, aggregates or layers on one of the water surfaces (such as bottom or top). Exemplary hydrophobic substances include, without limitation, substances comprising one or more alkyl groups, such as oils and fats, or one or more aromatic groups, such as polyaromatic compounds.

The term "hydrophilic", as used herein, describes a trait of a molecule or part of a molecule which renders the molecule dissolvable, at least in part, in water, aqueous solutions and/or other polar solvents. The phrase "at least in part" means that the substance is either completely dissolvable in such solvents or reaches its maximal saturation concentration in water, aqueous solutions and/or other polar solvents, while the remainder of the substance is in the form of a suspension of small solid particles in the solvent. Hydrophilic agents are therefore typically water-soluble agents, in which the dissolvability of the molecule in water, aqueous solutions and polar solvents is higher than its dissolvability in oils, organic solvents and other non-polar solvents. The term "hydrophilic", as used and defined herein, also encompasses amphiphilic or amphiphatic agents, which are characterized by a part of the molecule that is hydrophilic and hence renders the molecule dissolvable, at least to some extent, in water and aqueous solutions.

The terms "amphiphilic" or "amphiphatic", as used herein, refer to a trait of a molecule having both hydrophilic and hydrophobic nature, namely a polar region that can be either ionic, or non-ionic, and a non-polar region. Exemplary hydrophilic substances include, without limitation, compounds comprising one or more charged or polar groups such as one or more carboxyl groups (e.g., organic acids), one or more hydroxyl groups (e.g., alcohols), one or more amino groups (e.g., primary, secondary, tertiary and quaternary amines), and any combination thereof. Such groups are present, for example, in peptides and saccharides and in many other naturally occurring and synthetic substances. Amphiphilic substances also comprise, alongside with charged or polar groups, also non-polar moieties such as those exhibited in hydrophobic substances, as these are defined hereinbelow. Exemplary types of amphiphilic molecules include, without limitation, anionic molecules (such as sodium dodecyl sulfate), cationic molecules (such as benzalkonium chloride), zwitterionic molecules (such as cocamidopropyl betaine) and non-ionic molecules (such as octanol).

The present inventor has further devised and practiced highly porous polymers which are characterized by a mean pore size in the nano-scale, which exhibit exceptionally high surface area and thus exhibit high burst release, useful in applications which require high concentrations of the drug at the initial stage of the treatment.

As demonstrated in the Examples section that follows, highly porous poly(DL-lactic-co-glycolic acid) films with controlled release of horseradish peroxidase (HRP) as a model protein have been successfully prepared and studied.

These exemplary films, which can be designed for use in tissue-regeneration applications, were investigated for the effects of the emulsion's formulation and host polymer's characteristics on the film's microstructure and HRP release profile over 4 weeks. A dual pore size population has been found to be characteristic to some films, with large 12-18 μm pores and small 1.5-7 μm pores, and porosity in the range of 76-92%, determined as the area occupied by the pores divided by the total area. As further shown in the Examples section, an increase in the polymer concentration and its initial molecular weight, organic/aqueous (O:A) phase ratio and lactic acid content, or a decrease in the HRP concentration, all resulted in a decreased burst effect and a more moderate release profile. A simultaneous change in two or three of these formulation parameters (compared to a reference formulation) resulted in a synergistic effect on the HRP release profile. A constant HRP release rate was achieved when a composite film was used, and human gingival fibroblast adhesion to the films indicated good biocompatibility. Appropriate selection of the emulsion's parameters has been shown to yield highly porous films with the desired protein-release behavior which can serve as scaffolds for bioactive agents in various applications.

The present inventor has further devised and practiced systems in which a highly porous hydrophobic polymeric is applied onto another film, the latter being a hydrophilic and wettable polymer which improves the initial interaction between aqueous physiological media and the porous polymer.

The term "wettable", as used herein refers to an attribute of a substance, or a surface of a substance, which describes its interaction with water or other aqueous media such as physiological media and is known as "wetting". A wettable substance or surface may also be regarded as hydrophilic while a non-wettable substance or surface as hydrophobic. The term "wetting", as used herein refers to the ability of a liquid (water or other aqueous media) to maintain contact with a solid surface, resulting from intermolecular interactions when the two come in contact. The degree of wetting (wettability) is determined by a force balance between adhesive and cohesive forces, hence wetting plays a main role in the bonding or adherence of the two materials. Wetting and the surface forces that control wetting are also responsible for other related effects, including capillary effects, liquid penetrability and swelling of a substance.

Systems for Effecting Specific Drug Release Profiles:

A "drug release profile" is a general expression which describes the temporal concentration of a drug (a bioactive agent) as measured in a particular bodily site of interest as a function of time, while the slope of a concentration versus time represents the rate of release at any given time point. A drug release profile may be sectioned into rate dependent periods whereby the rate is rising or declining linearly or exponentially, or staying substantially constant. Some of the typically sought rates include the burst release rate and the sustained release rate.

The phase "burst release", as used herein, is consistent with a rapid release of a drug into the bodily site of interest, and is typically associated with an exponential increase of the drug's concentration, growing from zero to a high level at a relatively short time. Typically, the burst release section of the drug release profile ends briefly and then gradually changes to a plateau, or a sustained release section in the release profile.

The phrase "sustained release", as used herein, refers to the section of the drug release profile which comes after the burst release part, and is typically characterized by constant rate and relative long duration.

The main differences between the burst and the sustain parts of a release profile are therefore the rate (slope characteristics) and duration, being exponential and short for the burst release, and linear and long for the sustained release; and both play a significant role in drug administration regimes. In most cases, the presence of both a burst release section and a sustained release section is unavoidable and stems from chemical and thermodynamic properties of the drug delivery mechanism.

In the context of embodiments of the present invention, the phrase "high burst release" is an attribute of a drug-releasing system, as described herein, which refers to the amount of drug that is being released from the system during the initial stage of exposure of the system to the environment of its action (e.g., physiological environment), wherein the amount is in excess of 20% of the total amount contained in the system and the initial stage is be regarded as the first six hours from exposure.

In some embodiments of the present invention, "high burst release" describes an attribute of a drug-releasing system, as described herein, in which 30%, 40%, 50%, 60% and even higher percentages of the bioactive agent (drug) are released during the first 6 hours of exposing the system to a physiological medium. Any value between 20% and 100% of the bioactive agent (drug) are contemplated.

Accordingly, the phrase "low burst release" refers to drug-releasing systems wherein less than 20% of the contained drug is released within the first six hours of exposure.

In some embodiments of the present invention, "low burst release" describes an attribute of a drug-releasing system, as described herein, in which 15%, 10%, 5% and even lower percentages of the bioactive agent (drug) are released during the first 6 hours of exposing the system to a physiological medium. Any value between 20% and 1% of the bioactive agent (drug) are contemplated.

A typical drug delivery mechanism, relevant in the context of the present embodiments, consists of a reservoir containing a predetermined and exhaustible amount of the drug, and an interface between the drug's reservoir and the physiological environment. Typically, the drug release commences at the initial time point when the reservoir is exposed to the physiological environment, and follows typical diffusion-controlled kinetics.

In some medical applications it is desirable to deliver a large amount of a drug at a relatively short period of time, however, for most drug delivery application, the burst stage releases more drug than is necessary (and in some cases more than optimal, e.g., at a toxic level) while depleting the reservoir from the drug, leading to premature shortening of the therapeutic period. Such problems are common to most drug delivery devices based on hydrophilic/wettable polymers which tend to deploy their content, namely the encapsulated drug, too rapidly.

According to some embodiments of the present invention, the reservoir of the drug consists of a polymeric porous film, having encapsulated or otherwise entrapped therein and/or thereon a bioactive agent (e.g., a drug).

The term "film", as used herein, is a substantially two-dimensional body having a thickness which is at least 10 times smaller than any of its length or width, and typically having an overall shape of a thin sheet. According to some embodiments of the present invention, a film can be flexible and therefore can be shaped as desired when used. Alternatively, a film can be used, if desired, to form tubes, bags and the likes, and can also be used to wrap other objects. For example, a medical device which comprises a film according to some embodiments of the present invention, can be shaped into a sleeve (tube) and be wrapped around an elongated bodily organ (artery), or line the interior of a bodily organ (intestine).

The thickness of the film correlates to the drug-reservoir capacity, and can be tailored so as to suit any specific application for which the systems, according to some embodiments of the present invention, are used for. For example, for long-range temporal drug delivery, a large reservoir of the drug is required, and hence relatively thick films are useful and desired in many applications. A relatively thick film is also required to encapsulate large bioactive agents such as virus-shells and cells, while the entrapment of relatively small drug molecules which are needed in small locally-distributed amounts may suffice with a relatively thin film. Therefore, the thickness of the film, according to the present embodiments, can range from about 10 μm to about 2000 microns and in certain cases can be even up to 1 cm.

The thickness of the polymeric porous film depends on the viscosity of the emulsion used to make the films, hence, the more viscous the emulsion, the thicker the resulting film may be. Alternatively, thicker films may be a result of multiple layering, as discussed hereinbelow.

The release profile of a bioactive agent from the polymeric porous film, according to some embodiments of the present invention, correlates, at least in part, to diffusion controlled kinetics, and hence correlates to the surface area of the film (the interface between the drug's reservoir and the physiological environment), which is governed primarily by the microstructure of the film. The microstructure of the porous film is defined by the porosity (ratio of void volume/area to total volume/area), and the size of the pores, all of which are controlled by the composition and processing of the inverted emulsion used for making the film, according to some embodiments of the present invention.

The term "emulsion" as used herein, describes a mixture of two immiscible liquids, typically referred to as phases, such as water and oil. One liquid (typically referred to as the dispersed phase) is dispersed in the other (typically referred to as the continuous phase). The term "emulsifier" (also referred to herein as a surfactant or a surface active agent) as used herein, refers to a substance which stabilizes an emulsion. As used herein, the term "surfactant" describes a substance that is capable of modifying the interfacial tension of the liquid in which it is dissolved.

According to some embodiments, the emulsion used to form the polymeric porous film of the systems presented herein is a "water-in-oil" emulsion (also referred to herein and in the art as reversed or inverted emulsion, wherein droplets of the aqueous phase are dispersed in a continuous organic (oil) phase.

The emulsion, according to some embodiments of the present invention, is provided by preparing two solutions, one being the aqueous phase (water/aqueous-based phase) and another being the organic phase (oil/organic-based phase).

The organic phase is prepared by dissolving one or more polymers and/or copolymers in an organic solvent. The organic solvent is selected immiscible with an aqueous solution. Examples of such organic solvents include, without limitation, chloroform, dichloromethane, carbon tetrachloride, methylene chloride, xylene, benzene, toluene, hexane, cyclohexane, diethyl ether and carbon disulfide.

The organic phase may contain additional organic-soluble substances including an organic-soluble/hydrophobic bioactive agent, as detailed hereinbelow. The aqueous phase may contain solely water, or may contain additional water-soluble substances including a water-soluble/hydrophilic bioactive agent, as detailed hereinbelow.

According to some embodiments of the present invention, the polymer comprising the polymeric porous film can be either biodegradable or non-degradable.

The term "polymer", as used herein, encompasses organic and inorganic polymers and further encompasses one or more of a polymer, a copolymer or a mixture thereof (a blend).

As used herein, the term "non-degradable" describes a substance which does not undergo degradation under physiological and/or environmental conditions. This term typically refers to substances which decompose under these conditions such that more than 50 percents do not decompose within at least 1 year, within 2 years, 3 years, 4 years, and up to 10 years and even 20 or 50 years.

In such a case where the film is made from a stable non-degradable polymer, the drug will be released from the porous film according to diffusion controlled kinetics through the porous matrix, and in some cases swelling of the host polymer in water will further augment the drug-release profile although no degradation of the host polymer will be involved is that process.

Systems comprising non-degradable polymers are useful, for example, in applications which require at least part of the system to be tenable for extended periods of time, possibly extending after the drug has been exhausted from the film (reservoir).

While any polymer, copolymer or a mixture of polymers and/or copolymers can be used for producing the films described herein, according to some embodiments of the present invention, the film is made from a biodegradable polymer.

The term "biodegradable", "bioresorbable" and "bioabsorbable", as used interchangeably in the context of the present invention, describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The terms "bioresorbable" and "bioabsorbable" further describe a substance that decomposes under physiological conditions to break down to products that undergo bioresorption into the host-organism, namely, become metabolites of the biochemical systems of the host-organism. In the context of some embodiments of the present invention, bioresorbable relates to materials and objects that can be broken down by the body and that do not require mechanical removal.

It is noted herein that there are some biodegradable polymers that degrade very slowly in relative terms. For example, polycaprolactone-based structural elements exhibit noticeable degradation only after a period of 4-5 years. The terms "bioresorbable" and "bioabsorbable" therefore encompass substances the biodegrade within a time period that ranges from a few hours and a few years, including a few days and a few months.

Exemplary biodegradable polymers according to the present embodiments are non-toxic and benign polymers. Some biodegradable polymers are bioresorbable polymers which decompose into non-toxic and benign breakdown products that are absorbed in the biochemical systems of the subject.

In systems comprising a biodegradable polymeric porous film, the drug release profile is affected also from the rate of disintegration of the reservoir's matrix, namely the film. Such systems are advantageous in applications where degradation of thereof allows obviating its removal after the drug delivery system has served its purpose.

The biodegradation of the film made from a biodegradable polymer may further be controlled by the addition of agents which can control and modify the biodegradation rate of the polymer composing the film.

Hence, according to embodiments of the present invention, a biodegradable polymeric porous film further includes a biodegradation promoting agent.

A biodegradation promoting agent accelerates the chemical and/or biochemical degradation processes by providing the required chemical conditions such as pH, ionic-strength, highly-active and readily activated species and enzymatic co-factors. Non-limiting examples of biodegradation promoting agents include cellulose phosphates, starch phosphates, calcium secondary phosphates, calcium tertiary phosphates and calcium phosphate hydroxide.

Non-limiting examples of biodegradable polymers which are suitable for use forming the systems and films described herein, include homo-polymers and copolymers such as aliphatic polyesters made of glycolide (glycolic acid), lactide (lactic acid), caprolactone, p-dioxanone, trimethylene carbonate, hydroxybutyrate, hydroxyvalerate, polypeptide made of natural and modified amino acids, polyethers made of natural and modified saccharides, polydepsipeptide, biodegradable nylon co-polyamides, polydihydropyrans, polyphosphazenes, poly(ortho-esters), poly(cyano acrylates), polyanhydrides and any combination thereof.

According to an exemplary embodiment of the present invention, the biodegradable polymer is an aliphatic polyester such as, for example, poly(glycolic acid), poly(lactic acid), polydioxanone (PDS), poly(alkylene succinate), poly(hydroxybutyrate), poly(butylene diglycolate), poly(epsilon-caprolactone) and a co-polymer, a blend and a mixture thereof.

Exemplary aliphatic polyesters that were found suitable for use in the context of the present invention include poly(L-lactic acid), poly(glycolic acid) and/or copolymers thereof such as poly(DL-lactic-co-glycolic acid).

According to an embodiment of the present invention, the polymeric film is made of poly(DL-lactic-co-glycolic acid).

It is noted herein that some biodegradable polymers, such as biodegradable aliphatic polyesters, which are highly suitable for forming the systems and films described herein, are hydrophobic polymers. In the context of the present embodiments, the polymeric system, which can be used as an effective for drug-releasing system, is based on a water-in-oil emulsion which required an organic (oil) phase and an aqueous (water) phase. A hydrophobic polymer is therefore advantageous in forming the polymeric systems presented herein. The hydrophobicity of the polymer is further advantageous since it allows adjusting finely the rate of release of bioactive agents therefrom due to the limited wettability and attenuated swelling, dissolution and degradation at physiological conditions. As discussed herein, the porosity and mean pose size of a polymeric porous film made from such hydrophobic biodegradable polymers serves as means to achieve any desired drug release profile. Hydrophobic polymers are further advantageous since they are highly suitable for encapsulating or sequestering hydrophobic bioactive agents which are more soluble in organic solvents in which the polymer is also soluble.

As stated above, the release (elution) process of an encapsulated bioactive agent from a film made form a biodegradable polymer also depends on and is controlled by the degradation process, which may be effected enzymatically, chemically or via other metabolic reactions in the physiological environment both in vivo and in vitro.

While reducing the preset invention to practice, it was found that some factors and attributes of the inverted emulsion affect the release profile of the bioactive agent encapsulated in and/or on polymeric porous films. These factors include, but are not limited to:

the composition of the polymer/copolymer in the emulsion making the film, namely the nature of the polymeric constituents, or the nature and relative ratio between polymeric constituents in a copolymer;

the initial average molecular weight of the polymer or copolymer;

the concentration of the polymer or copolymer in the organic phase of the emulsion;

the organic phase to aqueous phase ratio of the inverted emulsion (O:A);

the optional use of specific surfactants and the nature of the surfactant;

the hydrophilic/hydrophobic nature of the bioactive agent; and the emulsion homogenization conditions.

The present inventor has surprisingly uncovered that by selecting particular sets of the above parameters, one can finely control the microstructure of the resulting films and thereby prepare drug-eluding films which can form a part of systems that are tailor-made for a specific medical application by virtue of the drug-release profile obtained therefrom.

Thus, the systems, according to some embodiments of the present invention, are characterized by several key attributes, which render them suitable for specific application in the medical field, which include the ability to release a wide scope of bioactive agents, including proteins, peptides and small hydrophobic or hydrophilic compounds, at predetermined drug release profile.

For example, a film possessing high porosity and very small pore size, is characterized by an exceptionally high surface area which translates to a capacity to exhibit high levels of drug release in the burst release stage of the drug release profile. Accordingly, a relatively lower surface area, typical to films characterized by large and/or fewer pores, would confer a lower burst release and a longer sustained release stage in the drug release profile.

According to an exemplary embodiment of the present invention, the film has a porous microstructure. As used herein, the term "porous" refers to the texture of a solid material being characterized by a multitude of randomly dispersed pores, voids and/or holes. Accordingly, "porosity" or void fraction is a measure of the void (i.e., "empty") spaces in a material, and is a fraction of the volume of voids over the total volume, between 0-1, or as a percentage between 0-100 percents.

According to some embodiments of the present invention, the polymeric porous film is characterized by an average pore diameter (pore size) that can range from 0.001 μm (1 nm) to 1000 μm (1 mm), including any pore size value within the above-indicated ranges.

According to some embodiments of the present invention, the polymeric porous film is characterized by a pore density (porosity) that can range from about 5% void volume per film volume to about 95% void volume per film volume, including any porosity value within the above-indicated ranges.

The following discusses in more detail each of the factors that were shown herein to affect the release profile of a bioactive agent from the described porous polymeric film, according to embodiments of the present invention, and thus were utilized while designing the systems described herein.

Polymer/Copolymer Composition:

As discussed hereinabove, one of the parameters which affect the drug release profile is the polymer (or copolymer)'s composition.

A polymer may be defined by its constituents who confer various macroscopic attributes thereto, such as chemical properties (hydrophobicity, solubility, wettability, degradability and the likes), mechanical properties (strength, hardness, elasticity, stickiness, springiness and the likes) and morphological/visual properties (transparency, color, softness, roughness and the likes).

In the context of embodiments of the present invention, it was found that the composition of the polymer can used as one of the parameters for finely controlling the polymer's hydrophobicity so as to control the morphology of the organic droplets in the emulsion and thus to control the microstructure of the porous polymer resulting therefrom.

According to some embodiments of the present invention, the polymer used to form the systems presented herein is poly(DL-lactic-co-glycolic acid), which is referred to herein as PDLGA or PLGA. This polymer, which is a copolymer of lactic acid and glycolic acid, is advantageously characterized by biodegradability and biocompatibility.

Among other parameters, the attributes of PDLGA are governed by the ratio of lactic-to-glycolic acid in the copolymer. The ratio of the PDLGA constituents can be denoted as a percent ratio of the two major components. For example, "50/50 PDLGA" is shorthand for poly(lactic-co-glycolic acid) wherein the content of lactic acid is substantially equal to that of glycolic acid, namely a 1:1 ratio. Accordingly, 75/25 PDLGA represents a 3:1 ratio of lactic acid to glycolic acid, and 25/75 PDLGA represents a 1:3 ratio of lactic acid to glycolic acid.

While reducing the present invention to practice, it was further found that manipulating the lactic acid to glycolic acid ratio in the copolymer can affect the chemical and physical properties of the emulsion containing PDLGA in the organic phase; hence it was found that the lactic acid to glycolic acid ratio affects the attributes of the polymeric porous film produced from the emulsion, according to some embodiments of the present invention.

As demonstrated in the Examples section that follows, in films made from emulsion formulations based on 75/25 PDLGA, which contains more lactic acid groups in the copolymer than the 50/50 PDLGA, the emulsion's organic phase is relatively more hydrophobic and the resulting emulsion's interfacial tension is higher, lowering the emulsion's stability and increasing the pore size in the resulting polymeric porous films.

According to some embodiments of the present invention, the lactic acid to glycolic acid ratio in the copolymer is selected so as to influence the drug release profile for higher or lower burst release, and can be any suitable ratio unlimited to 10/90, 20/80, 30/70, 40/60, 50/50, 60/40, 70/30, 80/20, 90/10 and any intermediate value therebetween, including a polymer made from 100% lactic acid or a polymer made from 100% glycolic acid.

Thus, for example, using polymers with a high content of glycolic acid (such as for example a 50/50 lactic acid:glycolic acid ratio or 25/75 lactic acid:glycolic acid ratio) results in a polymeric porous film with smaller pore size and thus higher burst release, while using polymers with high contents of lactic acid (such as for example, a 72/25 lactic acid:glycolic acid ratio poly(lactic acid) results in a polymeric porous film with larger pore size and thus lower burst release.

Hence, higher lactic acid content in the polymer leads to larger pores which correlate to an attenuated (lower) burst release.

Initial Polymer's Average Molecular Weight:

Another parameter that was found to have an effect of the microstructure of the film and thereby the release profile is the initial average molecular weight of the polymer. As demonstrated in the Examples section, an increase in the initial average MW of the host polymer results in a more hydrophobic polymer due to a smaller quantity of polar/charged end groups, rendering the polymer more hydrophobic. When the polymer is more hydrophobic, the water uptake rate of the resulting film is lowered, which is expected to result in a lower burst release; however, as demonstrated in the Examples section that follows, the other effect of polymer's hydrophobicity leads to smaller mean pore size and higher porosity, resulting in a higher burst release. These two seemingly opposite effects demonstrate that microstructure characteristics overpower chemical characteristics in this regard of initial molecular weight effect on burst release.

Hence, according to some embodiments of the present invention, systems more suitable for high burst release applications comprise films based on a relatively high initial average molecular weight of the polymer, and systems more suitable for low burst release and longer sustained release applications comprise films based on a relatively low initial average molecular weight of the polymer.

In films based on the copolymer PDLGA, a relatively low initial MW is lower than about 100 kDa, and a relatively high initial MW is higher than about 100 kDa. In some embodiments, a PDLGA copolymer having a relatively low initial MW has an initial MW lower than about 90 kDa, 80 kDa, 70 kDa, 60 kDa, 50 kDa, or 40 kDa. In some embodiments, a PDLGA copolymer having a relatively high initial MW has an initial MW higher than 110 kDa, 120 kDa, 130 kDa 140 kDa, 150 kDa, 160 kDa, 170 kDa, 180 kDa, 190 kDa, and even higher than 200 kDa.

Polymer's Concentration:

The inverted emulsion's organic (continuous) phase, according to some embodiments of the present invention, comprises an organic, water-immiscible solvent (such as chloroform or an equivalent) and a predetermined amount of the polymer.

While practicing the present invention, it was found that the higher concentration of a polymer in the emulsion, the higher the burst release is. Without being bound by a particular theory, it is assumed that the effect of increasing the polymer's concentration on the release profile is attributed to higher shear forces exerted on the aqueous dispersed phase, leading to a decrease in the size of the aqueous domains and leading to a smaller pore size and porosity.

As demonstrated in the Examples section, slower diffusion rates of the bioactive agent from a film, according to some embodiments of the present invention, is obtained when the polymer's concentration is lower than 17% and this probably also contributes to the decrease in the burst release for samples containing higher polymer concentrations.

Hence, according to some embodiments of the present invention, systems more suitable for high burst release applications comprise films based on a relatively high concentration the polymer, and systems more suitable for low burst release and longer sustained release applications comprise films based on relatively low polymer concentration.

In films based on the copolymer PDLGA, a relatively low concentration is lower than about 17% weight per volume (w/v) relative to the solution of the organic phase, and a relatively high concentration is higher than about 17% w/v. In some embodiments, a concentration of PDLGA is 17%, 16%, 15%, 14%, 13%, 12%, 10%, by weight, and even lower.

In some embodiments, the concentration of the PDLGA is 18%, 19%, 20%, 21%, 22%, 23%, 24%, 25%, 26%, 27%, 28%, 29%, 30%, 35%, 40%, 50%, by weight, and even higher.

Oil-in-Water Ratio:

As demonstrated in the Examples section that follows, when the organic-to-aqueous phase ratio is increased a decrease in pore size is observed, accompanied with a reduction in porosity. It has been further observed that such an increase in the organic-to-aqueous phase ratio leads to a reduction in the burst release levels.

The reduction in the pore size is attributed to the increase in the emulsion's viscosity, which enables the higher emulsion shear forces to reduce the size of the dispersed phase and therefore also the resulting pore size. A decrease in porosity effects diffusion kinetics inversely with respect to the decrease in pose size. The combined effects are assumed to lead to the observed reduction in the burst release levels.

Hence, according to some embodiments of the present invention, systems more suitable for high burst release applications comprise films based on a relatively low organic-to-aqueous ratio, and systems more suitable for low burst release and longer sustained release applications comprise films based on relatively high organic-to-aqueous ratio.

In films based on the copolymer PDLGA, a relatively high organic-to-aqueous ratio is higher than 5:1 O:A (e.g., from 5:1 to 10:1, or from 5:1 to 8:1), and a relatively low organic-to-aqueous ratio is lower than 5:1 O:A (e.g., from 4.5:1 to 1:1, or from 4:1 to 2:1).

Surfactant Effect:

The contribution of surfactants (surface active agents) to the final microstructure of the film is demonstrated in the examples section that follows. The addition of a surfactant at the preparation stage of the emulsion, as well as the nature of the surfactant was shown to affect the release profile of the bioactive agent from the film.

In general, it has been demonstrated herein that the surfactant nature and concentration affects the porosity and the pore size. It has also been shown that the requirement and effect of a surfactant is associated with the hydrophobic/hydrophilic nature of the bioactive agent, wherein a hydrophobic bioactive agent and a hydrophilic bioactive agent may not contribute to the stability of the emulsion, while an amphiphilic bioactive agent, which may act as a surfactant by itself, will obviate the use of an additional surface active agent at least to some extent.

Surfactants by nature are substantially amphiphilic, however they can be divided into more hydrophobic and more hydrophilic surfactants. In addition, surfactants can be characterized by their size, or high and low molecular weight, wherein polymeric and protein-based surfactants are regarded as being high molecular weight surfactants and small-molecule surfactants are regarded as low molecular weight surfactants.

Suitable surfactants include, without limitations, proteins and peptides, glycols and polyglycols, glycerides and polyglycerides, sorbates and polysorbates, sorbitan isostearate, sorbitan oleate, sorbitan sesquioleate, sorbitan trioleate, alkyl-amines and alkyl-amides, and esters, salts and mixtures thereof.

As demonstrated in the Examples section, incorporating more hydrophobic surfactants, such as Pluronic L-121 and Span 80, resulted in some decrease in mean pore size, but the stability of the emulsion has decreased. In contrast, incorporation of high molecular weight and more hydrophilic surfactants, such as the protein-based surfactants bovine serum albumin (BSA, a 66 kDa protein), horseradish peroxidase (HRP, a 44 kDa protein) and the polymeric surfactant poly (vinyl alcohol) (PVA, a 13-23 kDa polymer), had stabilizing effects, and the protein-based surfactants HRP and BSA were the most effective in reducing pore size.

Hence, according to some embodiments of the present invention, systems more suitable for high burst release applications comprise films prepared with a high molecular weight amphiphilic or hydrophilic surfactants, and systems more suitable for low burst release and longer sustained release applications comprise films prepared with no surfactants, low surfactant levels or more hydrophobic surfactants.

The surfactant concentration is given in weight per volume percentage (w/v %) relative to the volume of the aqueous phase or organic phase it is mixed into, wherein more hydrophobic surfactants are mixed into the organic phase, and amphiphilic or hydrophilic surfactants are mixed into the aqueous phase.

For example, the use of a high molecular weight amphiphilic or hydrophilic surfactant at a concentration of more than 2% will affect the resulting film so as to have a high burst release; and the use of a low molecular weight hydrophobic surfactant at a concentration of less than 2% will affect the resulting film so as to have a low burst release.

Hydrophilic/Hydrophobic Bioactive Agent:

As used herein, the phrase "bioactive agent" describes a molecule, compound, complex, adduct and/or composite that exerts one or more biological and/or pharmaceutical activities. The bioactive agent can thus be used, for example, to promote wound healing, tissue regeneration, tumor eradication, and/or to prevent, ameliorate or treat various medical conditions.

"Bioactive agents", "pharmaceutically active agents", "pharmaceutically active materials", "therapeutic active agents", "biologically active agents", "therapeutic agents", "drugs" and other related terms are used interchangeably herein and include, for example, genetic therapeutic agents, non-genetic therapeutic agents, small molecules and cells. Bioactive agents useful in accordance with the present invention may be used singly or in combination. The term "bioactive agent" in the context of the present invention also includes radioactive materials which can serve for radiotherapy, where such materials are utilized for destroying harmful tissues such as tumors in the local area, or to inhibit growth of healthy tissues, such as in current stent applications; or as biomarkers for use in nuclear medicine and radioimaging.

The bioactive agent can be a hydrophilic bioactive agent or a hydrophobic bioactive agent.

Representative examples of hydrophilic and/or of amphiphilic bioactive agents that can be beneficially incorporated in the films described herein include, without limitation, amino acids and peptide- and protein-based substances such as cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells, as well as hydrophilic or amphipatic radioisotopes, radiopharmaceuticals, steroids, vitamins, angiogenesis-promoters, drugs, anti histamines, antibiotics, antidepressants, anti-hypertensive agents, anti-inflammatory agents, antioxidants, anti-proliferative agents, anti-viral agents, chemotherapeutic agents, co-factors, cholesterol, fatty acids, bile acids, saponins, hormones, inhibitors and ligands, and any combination thereof.

Representative examples of hydrophobic bioactive agents that can be beneficially incorporated in the films described herein include, without limitation drugs, anti-coagulants, statins, hormones, steroids, lipids, antibiotics, antigens, anti-depressants, anti-hypertensive agents, anti-inflammatory agents, antioxidants, anti-proliferative agents, anti-viral agents, chemotherapeutic agents, haptens, inhibitors, ligands, radioisotopes, radiopharmaceuticals, toxins and any combination thereof.

Each of the hydrophilic and hydrophobic bioactive agents described herein can be a macro-biomolecule or a small, organic molecule.

The term "macro-biomolecules" as used herein, refers to a polymeric biochemical substance, or biopolymers, that occur naturally in living organisms. Polymeric macro-biomolecules are primarily organic compounds, namely they consist primarily of carbon and hydrogen, along with nitrogen, oxygen, phosphorus and sulfur, while other elements can be incorporated therein but at a lower rate of occurrence. Amino and nucleic acids are some of the most important building blocks of polymeric macro-biomolecules, therefore macro-biomolecules are typically comprised of one or more chains of polymerized amino acids, polymerized nucleic acids, polymerized saccharides, polymerized lipids and combinations thereof. Macromolecules may comprise a complex of several macromolecular subunits which may be covalently or non-covalently attached to one another. Hence, a ribosome, a cell organelle and even an intact virus can be regarded as a macro-biomolecule.

A macro-biomolecule, as used herein, has a molecular weight higher than 1000 dalton (Da), and can be higher than 3000 Da, higher than 5000 Da, higher than 10 kDa and even higher than 50 KDa.

Representative examples of macro-biomolecules, which can be beneficially incorporated in the films described herein include, without limitation, peptides, polypeptides, proteins, enzymes, antibodies, oligonucleotides and labeled oligonucleotides, nucleic acid constructs, DNA, RNA, antisense, polysaccharides, viruses and any combination thereof, as well as cells, including intact cells or other sub-cellular components and cell fragments.

As used herein, the phrase "small organic molecule" or "small organic compound" refers to small compounds which consist primarily of carbon and hydrogen, along with nitrogen, oxygen, phosphorus and sulfur and other elements at a lower rate of occurrence. Organic molecules constitute the entire living world and all synthetically made organic compounds, therefore they include all natural metabolites and man-made drugs. In the context of the present invention, the term "small" with respect to a compound, agent or molecule, refers to a molecular weight lower than about 1000 grams per mole. Hence, a small organic molecule has a molecular weight lower than 1000 Da, lower than 500 Da, lower than 300 Da, or lower than 100 Da.

Representative examples of small organic molecules, that can be beneficially incorporated in the films described herein include, without limitation, angiogenesis-promoters, cytokines, chemokines, chemo-attractants, chemo-repellants, drugs, agonists, amino acids, antagonists, anti histamines, antibiotics, antigens, antidepressants, anti-hypertensive agents, anti-inflammatory agents, antioxidants, anti-proliferative agents, anti-viral agents, chemotherapeutic agents, co-factors, fatty acids, growth factors, haptens, hormones, inhibitors, ligands, saccharides, radioisotopes, radiopharmaceuticals, steroids, toxins, vitamins and any combination thereof.

One class of bioactive agents is the class of therapeutic agents that promote angiogenesis, which can be encapsulated in the film comprising the systems presented herein, are useful for tissue regeneration and wound dressings. The successful regeneration of new tissue requires the establishment of a vascular network. The induction of angiogenesis is mediated by a variety of factors, any of which may be used in conjunction with the present invention (Folkman and Klagsbrun, 1987, and references cited therein, each incorporated herein in their entirety by reference).

Another class of bioactive agents which can be incorporated into the film comprising the systems presented herein, especially in certain embodiments which involve tissue regeneration and healing are cytokines, chemokines and related factors. Control over these agents can translate into a successful medical procedure when the immune system plays a key role.

Bioactive agents which can be beneficially incorporated into the film comprising the systems presented herein also include both natural or synthetic polymeric (macro-biomolecules, for example, proteins, enzymes) and non-polymeric (small molecule therapeutics) natural or synthetic agents.

Additional bioactive agents which can be beneficially incorporated into the film comprising the systems presented herein include anti-proliferative agents, cytotoxic factors or cell cycle inhibitors, including CD inhibitors, such as p53, thymidine kinase ("TK") and other agents useful for interfering with cell proliferation.

Bioactive agents that inhibit cell proliferation and/or angiogenesis (antiproliferative drugs) are particularly useful in drug-eluting systems designed for anticancer treatment, and include paclitaxel (TAXOL®), sirolimus (rapamycin) and farnesylthiosalicylate (FTS, salirasib), fluoro-FTS, everolimus (RAD-001) and zotarolimus. The encapsulation of two exemplary antiproliferative drugs, farnesylthiosalicylate and paclitaxel, in a porous film, is demonstrated in the Examples section that follows.

Additional bioactive agents that may be encapsulated beneficially into the film comprising the systems presented herein include FTS-methyl ester (FTS-ME), FTS-methoxymethylene ester (FTS-MOME), and FTS-amide (FTS-A) [Goldberg, L. et al., *J. Med. Chem.* (2009), 52(1), pp. 197-205], or 5-fluoro-FTS [Marciano, D. et al., *J. Med. Chem.*, (1995), 38(8), pp. 1267-1272]. These antiproliferative agents can be encapsulated in the porous film comprising the systems presented herein which can serve as medical devices such as, for examples, tumor targeting and destruction devices, and topical devices such as would dressings and skin patches. These devices, which can elute one or more antiproliferative agents and drugs, can be placed near or on a topical tumor site, or near or on a tumor site post its surgical removal.

Additional bioactive agents which can be beneficially incorporated into the film comprising the systems presented herein include gene delivery agents, which may be either endogenously or exogenously controlled, the family of bone morphogenic proteins ("BMP's"), cell survival molecules such as Akt, insulin-like growth factor 1, NF-kB decoys, 1-kB, Madh6, Smad6 and Apo A-1, viral and non-viral vectors and chemotherapeutic agents. Non-limiting examples of chemotherapeutic agents include amino containing chemotherapeutic agents such as daunorubicin, doxorubicin, N-(5, 5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2- dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents.

Additional bioactive agents which can be beneficially incorporated into the film comprising the systems presented herein include antibiotic agents. Non-limiting examples of antibiotic agents include gentamicin, ceftazidime, mafenide benzoyl peroxide, octopirox, erythromycin, zinc, silver, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; polydiallyldimethylammonium chloride and bile salts such as scymnol sulfate and its derivatives, deoxycholate and cholate. Three exemplary antibiotic agents, gentamicin, ceftazidime and mafenide, were used to demonstrate the efficiency of the systems presented herein, as presented in the Examples section that follows.

In the case of antibiotics used in treating acute infection in exposed living tissue, a typical requirement is to administer the antibiotic agent at such a level that would destroy the existing pathogenic bacterial population before it can develop resistance to that antibiotic agent. Typically, such an effect requires a high burst release followed by a moderate sustained release; and such a release profile can be achieved by a system according to some embodiments of the present invention, comprising a film with very high porosity and small pose size.

In the case of antibiotics used in prophylactic treatment, a typical requirement is to administer the antibiotic agent at moderate level for an extended period of time so as to prevent the sporadic development of an infection. Typically, such an effect requires a low burst release followed by a prolonged sustained release; and such a release profile can be achieved by a system according to some embodiments of the present invention, comprising a film with relatively low porosity and/or relatively large pose size.

Additional bioactive agents which can be beneficially incorporated into the film comprising the systems presented herein include analgesic agents, anaesthetic agents, pain-killers, pain-reducers and the likes. These include NSAIDs, COX-2 inhibitors, K+ channel openers, opiates and morphinomimetics.

Additional bioactive agents which can be beneficially incorporated into the film comprising the systems presented herein include hemostatic agents and antihemorrhagic (anti-haemorrhagic) agents.

Additional bioactive agents which can be beneficially incorporated into the film comprising the systems presented herein include cells of human origin (autologous or allogeneic), including stem cells, or from an animal source (xenogeneic), which can be genetically engineered if desired to deliver proteins of interest.

The film can further include, in addition to the bioactive agent, additional agents that may improve the performance of the bioactive agent. These include, for example, penetration enhancers, humectants, chelating agents, preservatives, occlusive agents, emollients, permeation enhancers, and anti-irritants. These agents can be encapsulated within the pores of a porous film or can be doped within the polymer forming the film.

The amount of the bioactive agents that is loaded in the film comprising the systems presented herein is selected sufficient to exert the desired therapeutic or biological effect. The effective amount of a bioactive agent therefore depends on the particular agent being used and can further depend on the desired application of the system. Thus, for example, in cases where the bioactive agent is a growth hormone, minute amounts of the agent are required so as to exert effective therapy. In cases where the bioactive agent is a protein or a peptide, medium range amounts of the agent are required. In cases where the bioactive agent is a metabolite having a high metabolic turnover rate or a chemical drugs, larger amounts of the bioactive agent are typically required.

Therefore, the amount of the bioactive agent in the film comprising the systems presented herein can range from about 0.00001 weight percentage to about 50 weight percentages of the amount of the total weight of the film, and ranges from about 0.1 weight percentage to about 30 weight percentages of the amount of the total weight of the film, or from about 1 weight percentage to about 20 weight percentages or from about 1 weight percentage to about 10 weight percentages of the total weight of the film, in cases where the bioactive agent is a biomolecules such as a peptide.

As indicated hereinabove, for bioactive agents such as growth factors, an amount in the system ranging from about 0.00001 to about 0.0001 percents of the total weight of the film is sufficient to exert the desired activity, whereby for bioactive agents such as, for example, synthetic drugs, an amount in the system ranging from about 1 to about 30 percents of the total weight of the film is useful.

The amount of the bioactive agent further affects the rate of release thereof, particularly in cases where the bioactive agent is encapsulated within the pore voids (a hydrophilic/amphiphatic agent), due to diffusion-related factors. Hence, the amount of the bioactive agent can be further manipulated in accordance with the desired release rate thereof.

The systems, according to the present embodiments, are designed such that the encapsulation of the bioactive agent is performed while retaining at least a part, most or all of the activity of the bioactive agent(s). Thus, these agents can exert their biological activity and/or therapeutic effect once the bioactive agent(s) is released to the physiological environment, as a result of the biodegradation of the film.

In general, since the systems presented herein are designed to be capable of incorporating any type of bioactive agent, hence the nature of the bioactive agent is not regarded as a parameter for its controlled release. The nature of the bioactive agent is taken as a given condition while some or all of the other parameters discussed hereinabove are adjusted so as to confer the desired release profile, depending on the intended use of the system (e.g., the medical condition to be treated by releasing the bioactive agent from the system).

For example, when designing a system for the high burst release of a hydrophobic bioactive agent which is found to increase pore size in the resulting film, one can use a (higher concentration of a) suitable surfactant so as to effect a decrease in pore size which has been shown to increase the burst release of the bioactive agent. Alternatively, when designing a system for the low burst release of a hydrophilic bioactive agent which was found to have a high burst release, one can use low molecular weight polymer so as to effect a low burst release of the bioactive agent.

As demonstrated in the Examples section that follows, films containing either hydrophilic or hydrophobic bioactive agents can be obtained so as to exhibit enhanced burst release and shorter sustained release, or exhibit an attenuated burst release and prolonged sustained release; thus the drug release profile can be designed for any desired application by tuning the aforementioned composition parameters, and emulsion processing parameters such as homogenization rates.

Homogenization Rate:

Emulsions are typically formed by intense mixing and stirring of two substantially immiscible liquids, referred to as phase homogenizing. The rate and duration of homogenization correlates to the amount of energy spent on breaking the domains of the dispersed phase into smaller droplets.

According to some embodiments of the present invention, systems suitable for high burst release applications comprise films based on emulsions which underwent high-energy homogenization, and systems more suitable for low burst release and longer sustained release applications comprise films based on emulsions which underwent low-energy homogenization.

In films based on the copolymer PDLGA, a relatively low-energy homogenization is achieved by homogenization at less than about 20000 rounds per minute (rpm) of the homogenizer's blade, and a relatively high-energy homogenization is achieved by homogenization at more than about 20000 rpm. Alternatively, a relatively low-energy homogenization is achieved by homogenization of the homogenizer's blade at less than about 30000 rounds per minute (rpm), less than 25000 rpm, less than 20000 rpm, less than 15000 rpm, less than 10000 rpm and any value therebetween, and a relatively high-energy homogenization is achieved by homogenization of the homogenizer's blade at more than about 5000 rounds per minute (rpm), more than 10000 rpm, more than 15000 rpm, more than 20000 rpm, more than 30000 rpm and any value therebetween.

Synergistic Effect:

While further studying the effects of emulsion's parameters on the release profile, it was surprisingly found that when adjusting simultaneously more than one parameter of the emulsion, the resulting film exhibits a change in the release rate that is greater than would be expected by adding the effects of each parameter as exhibited by itself. It is therefore taken that simultaneous alterations in more than one of the emulsion's parameters affect the release profile synergistically.

As demonstrated in the Examples section, in all the studied combinations of the parameters such as the initial molecular weight, the polymer's concentration, the O:A ratio and the concentration of the surfactant, the effect of a simultaneous change in two parameters resulted in a decrease in the burst release (e.g., from 57% to 15-20%), which is more effective than the sum of the single effects.

Composite Multilayered "Sandwich" Systems:

As discussed hereinabove, the thickness of the drug-eluding polymeric porous film, according to some embodiments of the present invention, is associated with the total amount of drug in the reservoir which is available for delivery. According to some embodiments of the present invention, the film can be formed in multiple layers as a result of freeze-drying additional layers of identical emulsion formulation onto a preformed and finished initial layer made from that emulsion formulation, and repeating that process for the number of desired layers/thickness.

In addition to forming layers using an identical emulsion for each layer, it is also possible to add a layer made from an emulsion formulation onto a preformed film made from a different emulsion formulation, thereby obtaining layers with different drug release profile and possibly a different drug altogether.

According to embodiments of the present invention, the film can be constructed with more than one layer, each having different composition and thus exhibit different properties such as biodegradability, density, porosity and other mechanical characteristics, and contain a different bioactive agent. Thus, each of the systems of the present embodiments can further comprise one or more bioactive agents.

In systems comprising films made from biodegradable polymers, first to degrade would be the layer which is close to the interface with the physiological media. As that layer is degraded and consumed and the pores are gradually exposed to the physiological environment, the bioactive agent(s) encapsulated in that layer is released. The process made involve release of the bioactive agent(s)_encapsulated in the other layer(s) simultaneously in cases the physiological medium penetrates deeper into the system through the first layer, and start eluding the agent encapsulated in deeper layers.

A release process of bioactive agents from a multiple-layered composite system can therefore be controlled by manipulating the composition of the biodegradable polymer composing each layer (film), the size, length and diameter of each layer (film), the thickness of each layer (film), the size and density of the pores, the amount and physicochemical properties of the bioactive agent(s) encapsulated within each layer (film) during the preparation process of the composite system.

According to some embodiments of the present invention, the system is a multilayer system having one or more films (layers) which contain active agent(s) and one or more films (layers) which does not contain any active agent. A layer that does not contain a bioactive agent, referred to herein as a "blank film", is useful for augmenting the drug release profile from adjacent drug-loaded film(s) and obtain more suitable characteristics for any given application.

A blank biodegradable film may also provide a temporary matrix for cell growth by virtue of having large pores which can accommodate cells. Since cell growth requires relatively large pores, and since relatively large pores may not be adequate for a desired drug release profile, a system which contains at least two different layers, each providing highly desired attributes, will be able to serve the goals sought in tissue regeneration treatments.

Tissue-System Interface:

The systems provided herein may be used as a medical device or form a part thereof, which is applied directly on a tissue for delivering a bioactive agent and as well as serving other purposes, as discussed hereinbelow. In some cases where the polymeric porous film is limited in its capacity to form tight and effective contact with the tissue, such as a wound or damaged and burnt skin tissue, a multilayer system would be constructed such that the layer that comes in direct contact with the treated tissue (e.g., a skin tissue) is selected and designed such that it can act as a mediating layer between the tissue and the film which incorporates the bioactive agent according to some embodiments of the present invention, or any other polymeric porous film of a multi-layered composite structure system according to some embodiments of the present invention. By mediating it is meant that the mediating layer allows the physiological medium to diffuse therethrough and reach the drug-loaded porous film which will release the bioactive agent thereto and allow it to diffuse back into the tissue.

According to some embodiments of the present invention, a multi-layered system having a polymeric porous film and a mediating layer (also referred to herein as composite structure system), is produced such that the two layers are in optimal contact therebetween. This goal can be achieved by, for example, pouring an emulsion formulation for forming the porous film onto a preformed mediating layer, or vice versa, pouring a formulation for forming a mediating layer onto a preformed polymeric porous film, according to some embodiments of the present invention.

The mediating layer's material is selected such that it is more wettable than the polymer forming the polymeric porous film, thus the composite system is capable of forming a tighter and more effective contact with the tissue. In the context of embodiments of the present invention, the phrase "more wettable substance or surface" refers to the higher capacity of the substance or surface to form tight contact and adhere to physiological media compared to that of the polymeric porous film made from a hydrophobic polymer.

The material making the mediating layer may also be biodegradable; hence such a composite system will have all the advantages of an all-biodegradable system, as discusses hereinabove. Exemplary biodegradable/bioresorbable materials, suitable for forming a mediating layer include, without limitation, collagen, chitosan, cellulosic-base polymers, gelatin, alginate, hyaluronic acid, soy protein, polyethylene glycols and the likes.

According to some embodiments of the present invention, the system presented herein is a composite system comprising at least one bioresorbable polymeric porous film encapsulating a bioactive agent, and a mediating layer comprising collagen.

Systems Defined by Specific Sets of Characteristics:

The polymeric systems presented herein may be characterized by one or more sets of attributes which define their release profile and structure.

Hence, according to an aspect of embodiments of the present invention, there is provided a polymeric system which includes a first polymeric porous film having incorporated therein a bioactive agent. The system, according to some embodiments of the present invention, is characterized by at least one of the following:

(a) the first polymeric porous film is prepared by freeze-drying a water-in-oil emulsion in which a polymer's composition, a polymer's concentration, a polymer's initial molecular weight, a concentration and/or a type of a surfactant, a homogenization rate and/or an oil phase to aqueous phase ratio (O:A) are selected such that at least 20% of the bioactive agent are released within 6 hours of contacting the system with a physiological medium and the remaining of the bioactive agent are released over a time period of at least 2 days;

(b) the first polymeric porous film is prepared by freeze-drying a water-in-oil emulsion in which a polymer's composition, a polymer's concentration, a polymer's initial molecular weight, a concentration and/or type of a surfactant, a homogenization rate and/or an oil phase to aqueous phase ratio (O:A) are selected such that no more than 20% of the bioactive agent are released within 6 hours of contacting the system with a physiological medium and the remaining of the bioactive agent are released over a time period of at least 7 days;

(c) a composite structure which comprises the first polymeric porous film and which further comprises a second polymeric film onto which the first polymeric porous film is applied; and (d) a mean pore diameter of the polymeric film lower than 1 micron.

A feature which may be common to all groups of systems is the polymer comprising the film. According to some embodiments of the present invention, that polymer is a hydrophobic biodegradable polymer, as described and discussed herein.

According to some embodiments of the present invention, the polymer is PDLGA, as described herein.

According to some embodiments of the present invention, the polymeric system of group (a) is being characterized by a high burst release which can be afforded by manipulating the parameters of the water-in-oil emulsion that is used to form a first polymeric porous film prepared by freeze-drying the emulsion, which include the polymer's composition, the polymer's concentration, the polymer's initial molecular weight, the concentration and/or the type of a surfactant, the homogenization rate and/or the oil phase to aqueous phase ratio (O:A). These parameters are selected such that at least 20% of the bioactive agent are released within 6 hours of contacting the system with a physiological medium.

In some embodiments, the remaining (percentage) of the bioactive agent is released over a time period of 2 days.

In some embodiments, the remaining bioactive drug is released over a time period of 1 day, 2 days, 7 days and up to 30 days or more.

According to some embodiments of the present invention, a high burst release is such that more than 20 percents of the bioactive agent are released within 6 hours or less of contacting the system with a physiological medium and the remaining of the bioactive agent are released over a time period of more than 2 days. Alternatively, more 30 percents of the bioactive agent are released within 6 hours or less, more 40% or more 50% of the bioactive agent are released within 6 hours or less. According to these embodiments, at least 20%, at least 30%, at least 40%, at least 50% and even more than 50% are released in the burst release phase. In some embodiments of such a release profile, the entire amount of the bioactive agent is released during a time period of 1-2 days, and the release profile is characterized by a high burst release.

High burst release is beneficial in, for example, treating an infected wound, targeted delivery of a drug, acute pain relief, hemostatic treatment, pulsatile release of a drug, encapsulation of flavors in processed food items and the likes.

For example, the treatment of an infected would require the delivery of a high concentration of an antibiotic agent so as to kill the pathogenic microorganisms without allowing any of the species to develop resistance thereto. Hence, according to some embodiments of the present invention, the parameters of the emulsion are selected so as to confer a high burst release of the bioactive agent in the form of an antibiotic agent.

In some embodiments, a polymer's composition is selected such that the hydrophobic nature of the polymer is decreased by using a polymer wherein the lactic acid to glycolic acid ratio is lower than, for example, 60/40. Hence, in some embodiments, the polymer's composition of the PDLGA is such that a lactic acid to glycolic acid ratio is lower than 60/40, and can be, for example, 55/45, 50/50, 45/55, 40/60 and 35/65. In some embodiments, that a lactic acid to glycolic acid ratio is 50:50.

In some embodiments, a polymer's composition is selected such that the shear forces exerted on the aqueous dispersed phase are increased by using a polymer concentration higher than, for example, 17% by weight of the total volume (w/v) of the organic phase. Hence, in some embodiments, the polymer's concentration in the organic phase is equal or higher than 17%, and can be, for example, 18%, 19%, 20%, 21%, 22%, 23%, 24%, 25%, 26%, 27%, 28%, 30% or even higher. In some embodiments, the polymer's concentration ranges from 15% to 40% w/v, or from 20 to 30% w/v, including any value therebetween. In some embodiments, the polymer's concentration is 25% w/v.

In some embodiments, the polymer's initial molecular weight is selected such that the mean pore size of the resulting film is decreased by using a polymer with an initial MW higher than, for example, 100 kDa. Hence, in some embodiments, the polymer's initial MW is 110 kDa, 120 kDa, 130 kDa, 140 kDa, 150 kDa, 160 kDa, 170 kDa, 180 kDa, 185 kDa, 190 kDa, 195 kDa, 200 kDa, or even higher. In some embodiments, the polymer's initial MW ranges from 100 kDa to 300 kDa, or from 120 kDa to 150 kDa, or from 150 to 200 kDa, with any intermediate values are also contemplated. In some embodiments, the polymer's initial MW is 185 kDa.

In some embodiments, the organic-to-aqueous phase ratio (O:A ratio) of the inverted emulsion is selected lower than, for example 5:1, leading to a decrease in the mean pore size of the resulting film. Hence, in some embodiments, the O:A ratio of the inverted emulsion is 4:1, 3:1, 2:1, and can be also 1:1. Any intermediate ratio is also contemplated. In some embodiments, the O:A ratio is 4:1.

In some embodiments, the emulsion may include a surfactant, which can stabilize the emulsion and therefore lead to a decrease in the mean pose size of the resulting film. Hence, in some embodiments, the emulsion includes a surfactant at a concentration of, for example, from 1 to 10% w/v, or from 2 to 8% w/v, or from 3 to 7% w/v, relative to the organic or aqueous phase or higher, including any intermediate value. In some embodiments, the surfactant's concentration is 5% w/v. In some embodiments, as the surfactant is a high molecular weight amphiphilic or hydrophilic surfactant, as described herein.

In some embodiments, the surfactant is a protein, as described herein.

In some embodiments, the emulsion is prepared using high-energy mixing so as to decrease the mean pose size of the resulting film by using at a homogenization rate of more than, for example 20000 rpm. Hence, in some embodiments, the emulsion is homogenized at a rate of 20000 rpm, 25000 rpm, 30000 rpm or higher. In some embodiments, the homogenization rate ranges from 25000 to 30000 rpm. Any intermediate values are also contemplated. In some embodiments, the homogenization rate is 28000 rpm.

Group (a) can further be characterized by selecting any one of the above-described parameters for effecting a high burst release. Group (a) can further be characterized by selecting any two, three or more of the above-described parameters simultaneously for effecting a high burst release.

Any one of the parameters and conditions listed above under group (a) affords a system capable of exhibiting a high burst release, and in addition exhibiting a porosity higher than 86% and/or a mean pore diameter lower than 5 μm, and in some cases group (a) is characterized by nano-scale pores, namely a mean pore diameter lower than 1 μm.

An exemplary system, according to some embodiments of the present invention, that belongs to group (a), can be described as a system comprising a polymeric porous film which is prepared from an emulsion in which:
 the polymer is PDLGA;
 the lactic acid to glycolic acid ratio of the PDLGA is 50:50;
 the concentration of the PDLGA is about 25% w/v;
 the initial molecular weight of the PDLGA is about 185 kDa;
 the emulsion comprises a protein-type surfactant;
 the concentration of the surfactant is about 5%;
 the emulsion is prepared at a homogenization rate of 28000 rpm; and/or
 the O:A ratio in the emulsion is 4:1.

According to some embodiments of the present invention, the polymeric system of group (b) is being characterized by a low burst release which can be afforded by manipulating the parameters of the water-in-oil emulsion that is used to form a first polymeric porous film prepared by freeze-drying the emulsion, which includes the polymer's composition, the polymer's concentration, the polymer's initial molecular weight, the concentration and/or type of a surfactant, the homogenization rate and/or the oil phase to aqueous phase ratio (O:A). These parameters are selected such that less than 20% of the bioactive agent are released within 6 hours of contacting the system with a physiological medium.

In some embodiments, the remaining (percentage) of the bioactive agent is released over a time period of at least 7 days.

In some embodiments, the remaining bioactive drug is released over a time period of 7, 8, 9, 10 and even 20 days or more.

According to other embodiments of the present invention, a low burst release is such that less than 30% of the bioactive agent are released within 6 hours of contacting the system with a physiological medium. According to these embodiments, less than 30%, less than 20%, less than 10% and even lower percentage of the bioactive agent are released within the first 6 hours, in a burst release phase In some embodiments of such a release profile, the entire amount of the bioactive agent is released during a time period of 7-30 days, and the release profile is characterized by a reduced burst release and thus by an enhanced sustained release phase.

Low burst release is beneficial in, for example, a prophylactic treatment of exposed tissue against infections, and in systems wherein the bioactive agent is an analgesic drug, a vitamin, a hormone, a proliferative agent, an antiproliferative agent, an analgesic agent and an anticancer agent.

For example, the treatment of a topical tumor would require the delivery of a constant concentration of an anti-cancerous agent so as to suppress the growth and eradicate the tumor over an extended period of time while not exerting a toxic effect on the entire body or healthy neighboring cells. Hence, according to some embodiments of the present invention, the parameters of the emulsion are selected so as to confer a low burst release of the bioactive agent in the form of an anti-cancerous agent.

According to some embodiments of the present invention, the bioactive agent incorporated in the systems of group (b) is a biomolecule.

According to some embodiments of the present invention, the systems of group (b) are suitable for use in tissue engineering.

In some embodiments, a polymer's composition is selected such that the hydrophobic nature of the polymer is increased by using a polymer wherein the lactic acid to glycolic acid ratio is higher than, for example, 50:50. Hence, in some embodiments, the polymer's composition of the PDLGA is such that a lactic acid to glycolic acid ratio is 55/45, 60/40, 65/35, 70/30 and 75/25.

In some embodiments, a polymer's composition is selected such that the shear forces exerted on the aqueous dispersed phase are decreased by using a polymer concentration lower than, for example, 17% by weight of the total volume (w/v) of the organic phase. Hence, in some embodiments, the polymer's concentration in the organic phase is equal or lower than 16%, 15%, 14%, 13%, 12%, 11% and can be, for example, 10% or lower. In some embodiments, the polymer's concentration is 15%.

In some embodiments, the polymer's initial molecular weight is selected such that the mean pore size of the resulting film is increased by using a polymer with an initial MW lower than, for example, 100 kDa. Hence, in some embodiments, the polymer's initial MW is 90 kDa, 80 kDa, 70 kDa, 60 kDa, 50 kDa, 50 kDa, 40 kDa, 30 kDa, 20 kDa, 10 kDa or lower. In some embodiments, the polymer's initial MW ranges from 20 kDa to 80 kDa, or from 30 kDa to 70 kDa, or from 40 kDa to 60 kDa, including any value therebetween. In some embodiments, the polymer's initial MW is 50 kDa.

In some embodiments, the organic-to-aqueous phase ratio (O:A ratio) of the inverted emulsion is selected higher than, for example 5:1, leading to a increase in the mean pore size of the resulting film. Hence, in some embodiments, the O:A ratio of the inverted emulsion is, 6:1, 7:1, 8:1, 9:1, 10:1, 11:1, 12:1 or higher. In some embodiments, the O:A ratio ranges from 5:1 to 10:1, or from 6:1 to 10:1, or from 7:1 to 9:1, including any values therebetween. In some embodiments, the O:A ratio is 8:1.

In some embodiments, the emulsion may include a surfactant; however, since a surfactant typically stabilizes the emulsion, use of a surfactant may lead to a decrease in the mean pose size of the resulting film. Hence, in some embodiments, the emulsion does not include a surfactant, or include a surfactant at a concentration of less than 5%, 3%, 2% and 1% w/v relative to the organic or aqueous phase or higher, and be selected as a low molecular weight hydrophobic surfactant.

In some embodiments, the emulsion is prepared using relatively low-energy mixing so as to not decrease the mean pose size of the resulting film, by using at a homogenization rate of less than, for example 20000 rpm. Hence, in some embodiments, the emulsion is homogenized at a rate of less than 20000 rpm or less than 10000 rpm. In some embodiments, the homogenization rate is 15000 rpm.

Group (b) can further characterized by selecting any one of the above-described parameters for effecting a low burst release. Group (b) can further characterized by selecting any two, three or more of the above-described parameters simultaneously for effecting a low burst release.

Any one of the parameters and conditions listed above under group (b) affords a system capable of exhibiting a low burst release and a prolonged sustained release, and in addition exhibiting a porosity lower than 86% and/or a mean pore diameter higher than 1 µm.

As exemplary system, according to some embodiments of the present invention, that belongs to group (b) can be described as a system comprising the polymeric porous film which is prepared from an emulsion in which:
  the polymer is PDLGA;
  the lactic acid to glycolic acid ratio of the PDLGA is 75:25;
  the concentration of the PDLGA is 15% w/v;
  the initial molecular weight of the PDLGA is 50 kDa;
  the emulsion is prepared at a homogenization rate of 14000 rpm; and/or
  the oil phase to aqueous phase ratio (O:A) in the emulsion is 8:1.

As discussed hereinabove, when adjusting more than one of the aforementioned parameters characterizing the systems, according to some embodiments of the present invention, a synergistic effect on the release profile is obtained.

Hence, according to some embodiments of the present invention, the polymeric system of group (b) is being characterized by a polymeric film prepared by freeze-drying an emulsion in which at least two of a polymer's concentration, a polymer's initial molecular weight, a concentration of a surfactant and/or an oil phase to aqueous phase ratio (O:A) are selected such that less than 20% of the bioactive agent are released within 6 hours of contacting the system with a physiological medium and the remaining of the bioactive agent are released over a time period of at least 7 days.

The synergistic effect is even more pronounced in cases wherein the polymer is hydrophobic and the surfactant is a protein-type surfactant.

For example, a group (b) system is achievable when the concentration of the PDLGA in the emulsion is higher than 17% w/v and the concentration of the surfactant is less than 1%, as described herein.

Alternatively, a group (b) system is achievable when the initial molecular weight of the PDLGA is lower than 100 kDa and the concentration of the surfactant is less than 1%, as described herein.

Further alternatively, a group (b) system is achievable when the oil phase to aqueous phase ratio (O:A) is higher than 5:1 and the concentration of the surfactant is less than 1%, as described herein.

Further alternatively, a group (b) system is achievable when the concentration of the PDLGA in the emulsion is higher than 17% w/v, the oil phase to aqueous phase ratio (O:A) is higher than 5:1 and the concentration of the surfactant is less than 1%.

According to some embodiments of the present invention, the polymeric system of group (d) is being characterized by a first polymeric porous film having a mean pore diameter lower than 1 µm, also referred to herein as nanostructure films.

As discussed and demonstrated herein, systems comprising nanostructure films are typically characterized by a high burst release due to their increased surface area. As such, systems comprising nanostructure films are suitably designed for high burst applications, as discussed herein, wherein at least 20% of the bioactive agent are released within 6 hours of contacting the system with a physiological medium and the remaining of the bioactive agent are released over a time period of no more than 2 days, as described herein.

Systems belonging to group (d) may further be characterized by a porosity higher than 80%.

In some embodiments, the first polymeric porous film of a system belonging to group (d) is prepared by freeze-drying a water-in-oil emulsion which comprises a polymer, a bioactive agent and a surfactant. As discussed hereinabove, the use of surfactants increases the stability of the inverted emulsion and decreases the mean pore size of the resulting polymeric porous film. As demonstrated hereinbelow, high molecular weight amphiphilic and hydrophilic surfactants, such as proteins, used at a concentration ranging from 1% to 10% weight by volume of the phase they are mixed in, are highly suitable for obtaining nanostructure films for high burst release applications.

In some embodiments, systems of group (d) are formed from an emulsion which is prepared by using high-energy mixing so as to decrease the mean pose size of the resulting film. The homogenization is performed at a rate of more than, for example 20000 rpm. Hence, in some embodiments, systems of group (d) are form from an emulsion which is homogenized at a rate that ranges from 20000 rpm to 30000 rpm, as described herein.

Group (d) may further be characterized by any one of the aforementioned parameters and attributes. As exemplary system, according to some embodiments of the present invention, which belongs to group (d) can be described as a system comprising the polymeric porous film which is prepared from an emulsion in which:
  the polymer is PDLGA;
  the lactic acid to glycolic acid ratio of the PDLGA is 50:50;
  the concentration of the PDLGA is 17% w/v;
  the initial molecular weight of the PDLGA is 83 kDa;
  the emulsion comprises a protein-type surfactant;
  the concentration of the surfactant is 5%;
  the emulsion is prepared at a homogenization rate of 28000 rpm; and/or the oil phase to aqueous phase ratio (O:A) in the emulsion is 4:1.

According to some embodiments of the present invention, the polymeric system of group (c) is being characterized by a composite structure of more than one film, wherein each film may be designed to exhibit a high burst release or a low burst release, by manipulating various parameters thereof as presented hereinabove. Hence, systems belonging to group (c) are composite/multilayered systems, wherein each of the films constituting the system can be selected from any polymeric porous film described under group (a), group (b) and group (d), which is discussed hereinabove.

The systems of group (c) include a second polymeric film onto which the first polymeric porous film is applied. Alternatively these systems may include more than two polymeric porous films. According to some embodiments, the exterior layers of such a composite system may not include a bioactive agent and act as a mean for augmenting the drug release profile or serve matrices for other purposes, such as cell growth.

According to some embodiments of the present invention, a polymeric system of group (c) is a system which includes the first polymeric porous film and a second polymeric film, wherein the second polymeric film comprises a wettable polymer, as discussed hereinabove. According to some embodiments of the present invention, the wettable polymer is biodegradable, which may be selected from the group consisting of collagen, chitosan, cellulosic-base polymer and a polyethylene glycol.

An exemplary composite structure system, according to some embodiments of the present invention, consists of the polymeric porous film having the bioactive agent incorporated therein, and an additional polymeric film made of a wettable and biodegradable polymer. Such a composite structure system is highly suitable for use in topical applications, such as in a form of a wound dressing and/or a skin patch, which require no removal once the bioactive agent it delivers has been depleted.

According to some embodiments of the present invention, a polymeric system of group (c) is a composite structure or multilayered system (also referred to herein as a composite multilayered system), having a second polymeric porous film, wherein the first polymeric porous film is characterized by a mean pore diameter lower than 1 µm and the second polymeric porous film is characterized by a mean pore diameter higher than 10 µm. Alternatively, the composite multilayered systems are characterized by having more than two additional polymeric porous films, wherein the first polymeric porous film is characterized by a mean pore diameter lower than 1 µm and the other additional polymeric porous films are characterized by a mean pore diameter higher than 10 µm. As discussed hereinabove, such composite multilayered systems are highly suitable for tissue engineering since the exterior polymeric porous films can be designed to have poses which are suitably sized to host living cells.

In some embodiments, each of the systems of any of groups (a), (b) and (d) may further include a second polymeric film onto which the first polymeric porous film is applied, as described herein. Alternatively these systems may include more than two polymeric porous films, and according to some embodiments of the present invention, each of the additional polymeric porous films may be applied on either sides of the first film, forming a composite "sandwich" system.

A feature which may also be common to systems of any of groups (a), (b) and (d), according to some embodiments of the present invention, involves a system which includes the first polymeric porous film and a second polymeric film, wherein the second polymeric film comprising a wettable polymer, as discussed hereinabove.

Other features which may be common to all systems of any of groups (a), (b) and (d), according to some embodiments of the present invention, involve composite multilayered systems having a second polymeric porous film, wherein the first polymeric porous film is characterized by a mean pore diameter lower than 1 µm and the second polymeric porous film is characterized by a mean pore diameter higher than 10 µm. Alternatively, the composite multilayered systems are characterized by having more than two additional polymeric porous films, wherein the first polymeric porous film is characterized by a mean pore diameter lower than 1 µm and the other additional polymeric porous films are characterized by a mean pore diameter higher than 10 µm.

Preparation:

In order to produce the systems described herein, and particularly such films which combine morphologic properties with the capacity to encapsulate bioactive agents while retaining their activity and to controllably release these agents, there is provided a process of preparing the systems described herein. The process is effected by providing an emulsion containing an aqueous solution and an organic solution which comprises a polymer; forming a layer from the emulsion; and freeze-drying that layer to thereby obtain a polymeric porous film.

As mentioned hereinabove, in some embodiments of the present invention, the film is biodegradable, comprising a biodegradable polymer encapsulating one or more bioactive agents. As mentioned hereinabove, in addition to bioactive agent(s), additional ingredients, such as biodegradation promoting agents and other agents, can be added to the emulsion formulation in the process of preparing the film.

The film can be formed as a flat thin structure by means of applying a layer of an emulsion onto a flat surface. Alternatively the film can form by dipping a flat object into a vessel containing the emulsion, and the dried and cured film may be peeled off the object at the end of the process. Discrete pieces of film of any shape and form can be achieved by, for example, spraying, sputtering or brushing the emulsion on a flat surface or into shallow inward curved feature acting as molds, and large sheets of a formed film can be cut into any desired shape and form.

As discussed hereinabove, in case of a composite multilayered system, one film can serve as a flat surface for forming the next layer, or alternatively it can be dipped into an emulsion for forming additional layers thereon. As demonstrated in the Examples section that follows, such a composite "sandwich" film has been prepared and tested successfully.

The bioactive agent can be introduced to either the organic or the aqueous phase, depending on its nature, namely a hydrophobic bioactive agent, which is miscible in the solvent of the organic phase is dissolved or otherwise introduced into the organic phase, while a hydrophilic/amphiphilic bioactive agent which is water-soluble, is introduced into the aqueous phase.

The presence of the bioactive agent in either one of the phases of the emulsion determines many factors of its release profile, as discussed hereinabove and in the Examples section below. Without being bound by any theory, it is assumed that a hydrophilic/amphiphilic agent which is dissolved in the aqueous phase will be found in the droplets of the dispersed phase and subsequently will be incorporated to the film on the inner walls of the pores. Accordingly, a hydrophobic agent which is dissolved in the organic phase is assumed to be found in the continuous phase and subsequently will be incorporated to the solid material of the film surrounding the pores.

The organic or the aqueous phase may further include additional agents such as, for example, emulsifying agents (emulsifiers) which may be required to stabilize the emulsion, anti-static agents, chelating agents, preservatives, solubilizers, viscosity modifying agents, biodegradation promoting agents, penetration enhancers and other additional agents as described hereinabove.

Buffer salts which are suitable for use in the preparation of the emulsion according to embodiments of the present invention include, but are not limited, to citrate buffers, acetic acid/sodium acetate buffers and phosphoric acid/sodium phosphate buffers.

Emulsifiers which are suitable for use in the preparation of the emulsion according to embodiments of the present invention include, but are not limited, to vegetable derivatives, for example, acacia, tragacanth, agar, pectin, carrageenan and lecithin; animal derivatives, for example, gelatin, lanolin and cholesterol; semi-synthetic agents, for example, methylcellulose and carboxymethylcellulose; and synthetic agents, for example, Carbopols®.

As mentioned hereinabove, a bioactive agent(s) can be introduced to either the organic phase and/or the aqueous phase, depending on its solubility, stability and other characteristics, and the desired properties of the resulting film. Thus, for example, water-soluble bioactive agents such as proteins, peptides, growth factors and the like are dissolved in the aqueous phase. In these cases, water-in-oil emulsions would result in polymeric porous films in which the bioactive agent is assumed encapsulated within the pores of the film. As mentioned hereinabove, large discrete pores are desired so as to affect prolonged release of the bioactive agent.

Water-insoluble bioactive agents such as, for example, cytotoxic drugs and anti-proliferative agents, are dissolved in the organic phase. In these cases, water-in-oil emulsions would result in polymeric porous films in which the bioactive agent is assumed encapsulated within the polymer composing the film. As mentioned hereinabove, numerous and relatively small and interconnected pores are desired so as to affect efficient burst release of the bioactive agent.

A combination of water-soluble bioactive agents that are encapsulated in the pores and water-insoluble bioactive agents that are encapsulated in the polymer composing the film is also within the scope of the present invention.

When containing a bioactive agent, the aqueous phase is prepared at a temperature which would not adversely affect the bioactive agent, or otherwise adversely affect its activity. Typically the temperature of the aqueous phase is kept under 37° C. Similarly, other parameters of the preparation of the aqueous solution, such as pH, salinity and other chemical and physical parameters are kept at such levels as to preserve the activity of the bioactive agent(s).

The organic phase, when containing the bioactive agent, is prepared by selecting a solvent that would not affect the activity of the agent adversely.

Once the two solutions, i.e., the organic solution/phase and the aqueous solution/phase are prepared or otherwise provided, the two solutions are mixed at a predetermined ratio (O:A ratio) to thereby obtain a mixture thereof.

As discussed hereinabove and demonstrated in the Examples section that follows, the ratio between the aqueous and the organic phase in the emulsion may affect the properties of the resulting structure, and hence affect the drug release profile of the encapsulated bioactive agent.

According to some embodiments of the present invention, the ratio of the aqueous solution and the organic solution in the mixture may range from about 1 parts of the organic solution to 1 part the aqueous solution to about 20 parts of the organic solution to 1 part the aqueous solution. The ratio of organic solution to aqueous solution depends on the specific requirements from the final product and its intended use, and is selected per the guidelines provided hereinabove.

Once the mixture is obtained, the process of emulsification is effected to thereby obtain the emulsion. The process of emulsification, which is well known to any artisan skill in the art, is effected by a mechanical stirrer, mixer or homogenizer until the desired consistency is achieved.

As discussed hereinabove, the rate (energy input) and the time of emulsification mixing determine the size of the resulting pores in the film to a large extent. Rapid mixing for extended periods of time (typically using a homogenizer) will result in very fine pores in the porous film. Such rapid mixing is typical in cases where the bioactive agent is dissolved in the organic phase and nano-sized pores and/or high burst release, are desired, as is detailed hereinabove and demonstrated below in the Examples section.

As mentioned hereinabove, in cases where the bioactive agent has a limited solubility in water or is not soluble in water, the phase which will contain this bioactive agent is the organic (continuous) phase. In such cases, the aqueous phase may be used in order to introduce additional components such as buffers, emulsifying agents, anti-static agents, chelating agents, solubilizers, viscosity modifying agents, biodegradation promoting agents and penetration enhancers. In these cases the pores formed by the water droplets in the polymer may be very small and will accelerate the biodegradation process by increasing the surface area of the biodegradable polymeric film, leading to a high burst release.

When containing a bioactive agent, the homogenization is effected at a temperature which would not affect the bioactive agent adversely, or otherwise adversely affect its activity. Typically the homogenization is effected at temperature lower than 37° C. Similarly, other mechanical parameters of the homogenization process are kept at such levels as to retain the activity of the bioactive agent(s).

As presented hereinabove, the resulting emulsion is applied onto a substantially flat surface or shallow mold so as to form a layer of the emulsion thereon or therein, and thereafter the emulsion is flash-frozen and subsequently subjected to freeze-drying so as to solidify the emulsion and obtain the final films according to some embodiments of the present invention.

The phrase "freeze drying" (also known as lyophilization) as used herein is a dehydration process typically effected by deep-freezing the material, typically by flash-freezing in liquid nitrogen, and then reducing the surrounding pressure to allow the frozen solvent, typically water and organic solvents in the material to sublimate directly from the solid phase to gas, and solidify on a condenser or cold-trap.

If a freeze-dried substance is sealed to prevent the re-absorption of moisture, the substance may be stored at room temperature without refrigeration, and be protected against spoilage for extended periods of time. Freeze-drying tends to be less damaging to biomolecules compared to other dehydration methods, which involve higher temperatures or chemical desiccation.

According to some embodiments of the present invention, the process of freeze-drying, which is well known to any artisan skill in the art, is carried out at reduced temperature and pressure using conventional methods and tools. A porous film is therefore the product of a freeze-dried water-in-oil emulsion wherein the droplets of the dispersed aqueous phase turn to voids or pores in the solidified continuous organic phase of the polymer. In cases where the aqueous phase contains at least one bioactive agent, the droplets of the dispersed aqueous phase become microscopic capsules containing the bioactive agent(s) which are encapsulated, entrapped and embedded in a solid polymer once the emulsion is freeze-dried.

The process can provide means to encapsulate/incorporate a wide range of bioactive agents into the film of the systems described herein. The preparation of the film does not involve harsh conditions which otherwise abolish the activity of many bioactive agents. The preparation of the film via the formation of an emulsion comprising an aqueous phase and an organic phase enables the incorporation of bioactive agents having a hydrophilic/amphiphilic nature or a hydrophobic nature, and of a small organic molecule or a complex macro-biomolecule. The incorporation of a bioactive agent having a more pronounced solubility trait, such as a small and predominantly hydrophobic drug molecule, requires a different treatment in order to be incorporated successfully in a system as presented herein. A hydrophobic drug molecule is intuitively added to the organic phase where it is more soluble, and the use of surfactants may be required in order to stabilize the emulsion.

Medical Devices:

As discussed hereinabove, the system comprising polymeric porous films, according to some embodiments of the present invention, is designed suitable for use as, or form a part of medical devices and/or drug delivery systems in many medical procedures.

Hence, according to a further aspect of the present invention there is provided a medical device which is based on the system described herein.

In some embodiments of the present invention, the medical device is a biodegradable device. Generally, the main motivation to have a biodegradable medical device is to have a device that can be used while obviating the need to remove it at a later stage. In its simplest form, a biodegradable device having a bioactive agent delivery capacity consists of a dispersion of the bioactive agent in a polymeric film. The bioactive agent is typically released as the biodegradable polymeric film biodegrades in vivo into soluble products that can be absorbed and/or metabolized and eventually excreted from the body over a period of time which depends on the polymer and the physical dimensions of the device.

The term "delivering" or "delivery" as used in the context of the present embodiments refers to the act of enabling the transport of a substance to a specific location, and more specifically, to a desired bodily target, whereby the target can be, for example, an organ, a tissue, a cell, and a cellular compartment such as the nucleus, the mitochondria, the cytoplasm, etc.

Exemplary medical devices include, without limitation, devices for topical applications and implantable devices.

According to some embodiments of the present invention, the medical device is adapted for transdermal and/or topical applications in a subject, or otherwise placed on an external part of the body. It is particularly important that such medical device would cause minimal tissue irritation when used to treat a given tissue.

Exemplary devices which can be used for topical application include, without limitation, an adhesive strip, a bandage, an adhesive plaster, a wound dressing, a skin patch, guided tissue matrices, tissue regeneration devices, tumor targeting and destruction devices, a drug delivery patch and occlusive burn bandage device.

Implantable medical devices based on or comprising the systems described herein, are adapted for surgical applications in a subject, or otherwise placed on, in or near an internal bodily site, organ or tissue which is made accessibly during the surgical procedure, thereby eluding the bioactive agent at that internal bodily site at the desired high or low burst release. Since such systems can be made entirely from bioresorbable materials, their surgical removal is not required.

Exemplary implantable devices which can be used in surgical applications include, without limitation, a sleeve, a tube, a strip, a sheet and a patch, a plate, dental implants, orthopedic implants, guided tissue matrices, tissue regeneration devices, tumor targeting and destruction devices and periodontal devices.

According to some embodiments of the present invention, the medical device may be based on systems belonging to any one of the aforementioned group (a), and systems belonging to group (c) and/or group (d) which further exhibit a high burst release. Exemplary medical devices suitable for high burst release include, without limitation, wound dressings and skin patches. The bioactive agent incorporated in such high burst release devices is selected useful to serve the intended use of the device.

According to some embodiments of the present invention, the medical device may be based on systems belonging to any one of the aforementioned group (b) and/or group (c) which further exhibit a low burst release and prolonged sustained release. Exemplary medical devices suitable for low burst release include, without limitation, wound dressing and a skin patch, a tissue regeneration device and a directed antitumor device. The bioactive agent incorporated in such low burst release devices is selected useful to serve the intended use of the device.

The device is shaped and sized according to the intended use thereof. For example, a wound dressing is typically a flat and thin rectangular or round object which is laid upon the treated part of the skin such that the treated area is covered thereby. The wound dressing can be cut to any shape so as to cover any shape wound or skin area. For example, in the case of a wound dressing for treating an infected wound, the device would comprise a film designed for high burst release and the bioactive agent would be an antibiotic agent.

In another example, the implantable device is a thin sheet that is being shaped as an elongated sleeve or tube and then placed inside and against the inner walls of an artery or another medically treated blood vessel. For example, in the case of a sleeve for a port-surgery proliferative treatment inside an artery, the device would comprise a film designed for low burst release and the bioactive agent would be a hemostatic agent.

Methods of Treatment:

The systems and/or devices containing same described herein can be utilized in the treatment of various medical conditions in which release of the incorporated bioactive agent is desirable, whereby the polymeric film is designed so as to exhibit a release profile that suits the condition being treated.

Thus, for example, in cases of medical conditions that involve acute infections, the bioactive agent is an antibiotic agent and the film is characterized by a high burst release of the antibiotic agent upon contact with the infected tissue. In some embodiments, a mediating layer is used so as to facilitate the wetting of the film and improve the contact between the film and the infected tissue. For such medical conditions, a device containing the system can be designed as an adhesive strip, a bandage, an adhesive plaster, a wound dressing, a skin patch and an occlusive burn bandage device. The device is placed on the infected area so as to cover it and its immediate surroundings, and in case the system is made entirely from biodegradable materials, its removal is obviated.

In cases of medical conditions in which prevention of infection is desired (prophylactic treatment against infections), such as in case of burns and other medical conditions that involve exposed tissues, the bioactive agent is an antibiotic agent and the film is characterized by a low burst release of the antibiotic agent upon contact with the infected tissue. In some embodiments, a mediating layer is used so as to facilitate the wetting of the film and improve the contact between the film and the infected tissue. For such medical conditions, a device containing the system can be designed as an adhesive strip, a bandage, an adhesive plaster, a wound dressing, a skin patch and an occlusive burn bandage device. The device is placed on the exposed or otherwise treated area so as to cover it and its immediate surroundings, and in case the system is made entirely from biodegradable materials, its removal is obviated.

In cases of medical conditions in which require a rapid or prolonged release of a hormone, such as in case of some endocrinological medical conditions, the bioactive agent is a hormone and the film is characterized by a high or low burst release of the hormone upon contact with the infected tissue, respectively. The system can be an implantable system or a system for topical use. In some embodiments for topical use of a hormone-releasing system, a mediating layer is used so as to facilitate the wetting of the film and improve the contact between the film and the skin. For implantable applications, a device containing the system can be designed as a sleeve, a tube, a strip, a sheet and a patch and a plate. For medical conditions which can be treated topically, a device containing the system can be designed as an adhesive strip, a bandage, an adhesive plaster and a skin patch. In case the application is topical, the device is placed on an area of the skin which is close to the bodily site to be treated (e.g., a subcutaneous gland). In case the application is internal, the device is placed on or near the bodily site to be treated (e.g., a gland). In case the system is made entirely from biodegradable materials, its removal is obviated.

In cases of medical conditions in which require a prolonged release of an anti-cancerous agent, such as in cases of local anti-tumor treatment applications, the bioactive agent can be an anti-proliferative agent and the film is characterized by a low burst release of the anti-proliferative agent upon contact with the infected tissue. The system can be an implantable system or a system for topical use. In some embodiments for topical use of an anti-proliferative agent-releasing system, a mediating layer is used so as to facilitate the wetting of the film and improve the contact between the film and the skin. For implantable applications, a device containing the system can be designed as a sleeve, a tube, a strip, a sheet and a patch and a plate. For medical conditions which can be treated topically, a device containing the system can be designed as an adhesive strip, a bandage, an adhesive plaster and a skin patch. In case the tumor is a skin tumor, the device is placed on the tumor. In case the tumor is internal, the device is placed on or near the tumor. In case the system is made entirely from biodegradable materials, its removal is obviated.

In cases of medical conditions which require tissue regeneration, such as in cases of internal loss of soft or bony tissue or topical loss of soft tissue or skin, the bioactive agent can be a proliferative agent, a growth factor or a cytokine, or cells, and the film is characterized by a low burst release of the a proliferative upon contact with the infected tissue. The system can be an implantable system or a system for topical use. In some embodiments for use of a proliferative agent-releasing system, a composite structure system comprising additional films or layers suitable for serving as tissue growth matrices is used, and in addition a mediating layer can be used so as to facilitate the wetting of the film and improve the contact between the film and the tissue. For implantable or topical applications, a device containing the system can be designed in the shape of the damaged tissue or the shape of the missing tissue, and can therefore take any suitable form. In case the tissue to be grown is topical, the device is placed on the surrounding skin. In case the tissue to be grown is internal, the device is placed on the surrounding tissue. In case the system is made entirely from biodegradable materials, its removal is obviated.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Bioresorbable porous films were made of poly(DL-lactic-co-glycolic acid) (PDLGA), which is a co-polymer of DL-lactic acid and glycolic acid. For example, the denotation "50/50 PDLGA" refers to 50% DL-lactic acid and 50% glycolic acid co-polymer. The denotation "75/25 PDLGA" refers to 75% DL-lactic acid and 25% glycolic acid co-polymer. Co-polymeric compositions used included:

50/50 PDLGA, inherent viscosity 0.56 dL/g in $CHCl_3$ at 30° C., heaving initial average molecular weight of about 83 kDa;

50/50 PDLGA, inherent viscosity 0.4 dL/g (in $CHCl_3$ at 30° C., heaving initial average molecular weight of about 50 kDa);

50/50 PDLGA, inherent viscosity 1.13 dL/g (in $CHCl_3$ at 30° C., heaving initial average molecular weight of about 185 kDa);

75/25 PDLGA, inherent viscosity 0.65 dL/g (in $CHCl_3$ at 30° C., heaving initial average molecular weight of about 103 kDa);

Poly(DL-lactic acid) (PDLLA) inherent viscosity 0.55 dL/g (in $CHCl_3$ at 30° C., heaving initial average molecular weight of about 80 kDa);

All polymers were purchased from Lake-shore Biomaterials, Inc., AL, USA.

A BCA™ Protein Assay Kit (Pierce) was used for measuring the protein concentration of solutions with a relatively high (20-2000 μg/ml) protein concentration, and a Micro BCA™ Protein Assay Kit (Pierce) was used for measuring the protein concentration of solutions with a relatively low (0.5-40 μg/ml) protein concentration.

Drugs included: Farnesylthiosalicylate (FTS, Salirasib), lot 12894-A-01-002, was received from Concordia Pharmaceuticals (Ft. Lauderdale, Fla., USA); Paclitaxel (Genexol™) was purchased from Sam Yang Corp. (Seoul, Korea); Gentamicin sulfate (cell-culture tested) was obtained from Sigma-Aldrich (cat. G-1264); 4-Aminomethylbenzenesulfonamide acetate salt (mafenide acetate) (Sigma A-3305); and ceftazidime hydrate, 90-105% (Sigma C-3809).

Surface-active agents (surfactant): Bovine serum albumin (BSA), fraction V Cohn, 66 kDa (Sigma A-4503); Poly(vinyl alcohol) (PVA), 87-89% hydrolyzed, 13-23 kDa (Aldrich 36, 317-0); Horseradish peroxidase (HRP) with an initial enzymatic activity of 150-250 U/mg, 44 kDa (Sigma P-8250), served as a surfactant and a protein-type biomolecule model; Oxirane, methyl, polymer with oxirane (Pluronic® L-121™), 4000 g/mol (BASF, USA); and Sorbitan monooleate (Span 80), 428.608 g/mol (Sigma 85548).

Reference emulsion formulations contained 17.5% w/v 50/50 PDLGA polymer having initial average molecular weight of about 83 kDa in the organic solution, 5% w/w drug in the aqueous medium (relative to the polymer concentration), 1% albumin in the aqueous medium, and an organic to aqueous (O:A) phase ratio of 4:1 or 8:1 v/v.

Preparation of Polymeric Porous Films—General Procedure:

Pre-measured amounts of PDLGA, an organic-soluble drug and an optional organic-soluble surfactant are dissolved in chloroform to form an organic solution. Pre-measured amounts of an aqueous-soluble drug and an optional aqueous-soluble surfactant are dissolved in double-distilled water and then poured into the organic phase in a test tube. Homogenization of the inverted emulsion is performed using a Kinematica PT-3100 Polytron homogenizer operating at 5,000-18,000 rpm for 2-5 minutes. The inverted emulsion is poured into an aluminum dish and then flash-frozen (rapid immersion) in a liquid nitrogen bath to thereby form a film. Frozen films are placed in a pre-cooled (−105° C.) freeze-dryer (Virtis 101 equipped with a nitrogen trap) suitable for organic solvents, and freeze-dried in order to remove aqueous and other volatile solvents and preserve the microstructure of the inverted emulsion-based films. Drying is performed in two stages: (i) the freeze-dryer chamber pressure is reduced to 100 mTorr while the temperature remained at −100° C.; (ii) the condenser is then turned off after 5 hours and its plate temperature gradually increased to room temperature while the pressure is monitored between 100 and 700 mTorr. During this step the liquid nitrogen trap condensed excess water and solvent vapors. The films are stored in desiccators until use.

Composite ("Sandwich") Film Preparation:

An exemplary composite film, which was composed of three layers, contained an exemplary inner layer of porous 50/50 PDLGA film sandwiched between two exemplary PDLLA layers. The parameters of the exemplary 50/50 PDLGA inner layer were 25% w/v polymer, initial MW of about 83 kDa, O:A=8:1 and 0.5% w/w HRP concentration. The parameters of the exemplary PDLLA outer layers were 17.5% w/v polymer concentration, initial MW of about 80 kDa and O:A=2:1. The outer film layers did not contain HRP. The composite film preparation was performed by preparing an inner layer in the form of a film of 50/50 PDLGA, prepared as described hereinabove, and then immersing this film in the PDLLA emulsion, flash-freezing this coated film in liquid nitrogen and freeze-drying the composite outcome as described hereinabove.

In Vitro HRP Release Studies:

Small 1.5 cm by 2.0 cm films (four samples) were immersed in phosphate-buffered saline (PBS) at 37° C. for 28 days in order to determine the HRP release kinetics from these structures. The release studies were conducted in closed glass tubes containing 2.0 ml PBS medium. The medium was removed (completely) periodically, at each sampling time, and fresh medium was introduced. Sampling was carried out at 0.5, 1, 2, 3, 7, 14, 21 and 28 days.

The HRP concentration of each medium sample was determined using the micro BCA assay method, by measuring absorbance at 562 nm, using a SpectraMax 340 PC[384] plate reader spectrophotometer. Cumulative HRP release profiles were determined relative to the initial amount of HRP in the composite fibers (HRP released during the incubation period+the residue remaining in the fibers). Four repetitions were performed for each sample, and the results are presented as means±one standard deviation.

Residual HRP Recovery from the Films:

Briefly, residual HRP recovery from the films used for in vitro release experiments was conducted by placing the films in 1 ml sodium dodecyl sulfate (SDS)/NaOH 5%/0.1 M solution for 48 hours at 37° C. Following extraction, the HRP concentration was estimated using a micro BCA assay method as described above.

In Vitro Drug Release Studies:

Small films of 1.5 cm by 0.5 cm, were immersed in phosphate buffered saline (PBS) at 37° C. for 70 days in order to determine the various drug release kinetics therefrom in four repetitions. The release studies were conducted in closed glass tubes containing 3.0 ml PBS medium. The medium was removed completely at various time points, and at each sampling time fresh medium was introduced.

The medium's drug concentration was determined using Jasco High Performance Liquid Chromatography (HPLC) with a UV 2075 plus detector and a reverse phase column kept at 25° C. The operating HPLC conditions used for each of the four studied drugs are presented in Table 1.

for 30 minutes in order to achieve sterilization of the films. The alcohol was decanted and replaced by three washes of sterile PBS and left to dry in the lamina flow, blowing sterile air. Human gingival fibroblasts (HGFs, 3 or 4 subcultures of human gingival explants) were seeded at $10^5$ cells per dish in 2 ml growth medium covering the films. The cells were cultured in minimal essential medium (MEM) supplemented with 10% newborn bovine serum (NBS). The medium was replaced every 3 days. After 4-6 days, sub-confluent cultures were observed under a phase-contrast microscope. The medium was then decanted, the cells were washed with PBS and fixed with 5% formalin in PBS. Two hours later the formalin was removed, the cells were washed in PBS and stained with Coomassie blue stain to expose the cytoskeleton F-actin. Cells were detected on the films and on the culture dish exhibiting normal fibroblastic morphological features. Cultures without the presence of PDLGA films served as controls.

Example 1

Emulsion's Chemical Parameters for Controlling Drag-Release Profile

The technique of film preparation by freeze-drying inverted emulsions has been shown to preserve the temporal state of the emulsion in solid form. Proteins such as HRP, which contain hydrophobic/hydrophilic regions and transient electrostatic charges, have a natural tendency to adsorb to the

TABLE 1

| Drug | Method (mobile phase) | λ [nm] | Injected volume | Column | Retention time |
|---|---|---|---|---|---|
| Paclitaxel | 45% acetonitrile 55% DDW | 227 | 100 | RP Zorbax ODS 5 mm, inner diameter 4.6 mm, length 150 mm | about 4.5 |
| FTS | 80% acetonitrile 20% PBS | 322 | 100 | RP Ace 5 C18 5 mm, inner diameter 4.6 mm, length 250 mm | about 12 |
| | 70% acetonitrile 30% PBS | | | | about 14 |
| Mafenide acetate | Gradient: t = 0 min 0% acetonitrile 100% PBS t = 1.5 min 10% acetonitrile 90% PBS t = 4 min 0% acetonitrile 100% PBS | 267 | 30 | Inertsil ODS-3V 5 mm, inner diameter 4.6 mm, length 250 mm | about 5.5 |
| Ceftazidime hydrate | 5% acetonitrile 95% PBS | 254 | 50 | RP Zorbax ODS 5 mm, inner diameter 4.6 mm, length 150 mm | about 5.5 |

Morphological Characterization:

The morphology of the porous films (cryogenically fractured surfaces) was observed by scanning electron microscopy (SEM) using a JEOL JSM-6300 microscope at an accelerating voltage of 5 kV. The SEM samples were Au-sputtered prior to observation. The mean pore diameter (n=100 small pores or 50 large pores) and porosity of the observed morphologies were analyzed using the Sigma Scan Pro software, and statistics were calculated using SPSS 10 software. Statistical significance was determined based on ANOVA (Tukey-Kramer). The area occupied by the pores was calculated for each SEM fractograph using Sigma Scan Pro software in order to evaluate the porosity of the samples. Porosity was determined as the area occupied by the pores divided by the total area.

In Vitro Biocompatability Experiment:

Films of the reference sample (5 by 5 mm) composed of PDLGA only or PDLGA loaded with HRP were placed in 35 mm cell culture dishes and covered with 70% alcohol solution organic/aqueous interface in the inverted emulsion. Proteins thus act similarly to block-co-polymer surfactants, which are widely used as emulsifiers. The model protein HRP thus acts as a surfactant and the inverted emulsions are relatively stable in the range of formulation parameters used in this study.

The effects of the inverted emulsion's formulation parameters, i.e. HRP concentration, polymer concentration and O:A phase ratio, and also the host polymer's parameters, i.e. copolymer composition and initial molecular weight have been investigated. The study enabled the elucidation of the process-structure-release profile effects of these protein-eluting films. Another part of the study focused on the combined effect of at least two formulation/polymer parameters on the film's microstructure and on the resulting HRP release profile.

An emulsion formulation containing 17.5% w/v 50/50 PDLGA (initial MW 83 kDa) in the organic solution, 1% w/w HRP in the aqueous medium (relative to the polymer load), and an O:A phase ratio of 4:1 v/v, was used as the reference formulation, denoted reference formulation A. An example of the microstructure of a freeze-fractured surface of film derived from this formulation is presented in FIGS. 1A-B.

FIGS. 1A-B are SEM fractographs of a highly porous PDLGA film made from reference formulation A, showing a general view of a cross-section of a typical polymeric porous film according to some embodiments of the present invention (low magnification, FIG. 1A), and the characteristic features of the porous structure (high magnification FIG. 1B).

As can be seen in FIGS. 1A-B, a dual pore size population is observed for this sample, which was found to be typical for most the studied samples, i.e. the films usually contain two types of pores: large 12-18 μm pores and small 1.5-7 μm pores, with porosity in the range of 76-92%. The large pores probably result from coalescence of the smaller pores during the homogenization step and are partially interconnected by the smaller pores. The structural characteristics of some of the studied films and their formulation parameters are presented as means±one standard deviation in Table 2.

TABLE 2

| Emulsion parameters | Amount | Mean large pore diameter (μm) | Mean small pore diameter (μm) | Porosity |
|---|---|---|---|---|
| HRP concentration (% w/w) | 0.5 | 16.0 ± 1.6 | 4.5 ± 1.3 | 88.6 ± 1.4 |
| | 1.0 | 17.1 ± 2.7 | 4.3 ± 0.8 | 86.9 ± 2.6 |
| | 2.0 | 16.0 ± 1.4 | 3.9 ± 0.4 | 85.4 ± 2.2 |
| Polymer concentration (% w/v) | 15 | — | 5.5 ± 1.1 | 88.2 ± 2.9 |
| | 17.5 | 17.1 ± 2.7 | 4.3 ± 0.8 | 86.9 ± 2.6 |
| | 20 | 16.1 ± 2.3 | 3.2 ± 0.5 | 85.8 ± 2.9 |
| | 25 | 17.1 ± 1.9 | 1.5 ± 0.2 | 82.2 ± 3.3 |
| Organic/aqueous phase ratio (v/v) | 2:1 | 17.3 ± 3.3 | 4.7 ± 1.0 | 92.5 ± 1.0 |
| | 4:1 | 17.1 ± 2.7 | 4.3 ± 0.8 | 86.9 ± 2.6 |
| | 6:1 | 18.0 ± 3.8 | 3.0 ± 0.6 | 82.1 ± 1.6 |
| | 8:1 | 17.2 ± 2.1 | 2.3 ± 0.4 | 76.7 ± 2.5 |
| Copolymer composition | 50/50 | 17.1 ± 2.7 | 4.3 ± 0.8 | 86.9 ± 2.6 |
| | 75/25 | 16.6 ± 3.6 | 5.9 ± 0.8 | 89.2 ± 0.8 |
| Polymer's initial molecular weight (kDa) | 50 | — | 7.1 ± 1.4 | 87.7 ± 2.0 |
| | 83 | 17.1 ± 2.7 | 4.3 ± 0.8 | 86.9 ± 2.6 |
| | 185 | 16.4 ± 2.8 | 2.5 ± 0.6 | 85.3 ± 1.2 |

Effect of the Emulsion's Formulation Parameters on the Microstructure and HRP Release Profile:

The effects of the emulsion's formulation parameters (i.e. HRP concentration, polymer concentration in the organic phase and O:A phase ratio) on the HRP release profile were studied in light of the film's morphology, and the results of the HRP-release profile studies are summarized in FIGS. 2A-C.

FIGS. 2A-C present comparative plots of cumulative release of HRP by percents as a function of time (in days) as measured from exemplary polymeric porous films, according to some embodiments of the present invention, demonstrating the effect of a change in the emulsion's formulation parameters compared to reference formulation A, wherein FIG. 2A presents the effect of HRP concentration (solid diamonds denote 2% w/w, solid rectangles 1% w/w, and solid triangles 0.5% w/w); FIG. 2B presents the effect of polymer concentration (solid circles denote 15% w/v, solid rectangles 17.5 w/v, and empty triangles 25% w/v); and FIG. 2C presents the effect of O:A phase ratio (empty rectangles denote 2:1 ratio, empty diamonds 6:1, and X-signs denote 8:1 ratio).

FIGS. 3A-F presents SEM fractographs of exemplary polymeric porous films, according to some embodiments of the present invention, showing the effect on the microstructure of the films as a function of a change in the emulsion formulation's parameters, wherein the effect of HRP concentration is shown in FIGS. 3A-B; the effect of polymer concentration is shown in FIGS. 3C-D; and the effect of O:A phase ratio is shown in FIGS. 3E-F, and all films are made with 17.5% w/v 50/50 PDLGA polymer having initial average MW of about 83 kDa containing 1% w/w HRP at a phase ratio of 4:1.

All polymeric porous films exhibited HRP release profiles characterized by an initial burst effect followed by a decreased and sustained release rate over time. After 3 weeks, all samples released at least 80% of the encapsulated HRP.

Effect of HRP Concentration

As can be seen in FIG. 2A, showing the effect of the HRP concentration on its release profile, an increase in the enzyme concentration from 0.5% to 2% resulted in a notable increase in the burst release from 37% to 74% and also in the release rate (indicated by the higher slope), due to a higher driving force for diffusion.

As can be seen in FIGS. 3A-F and Table 2, SEM observations show almost no change in the porosity and pore size of both large and small pore populations with the increase in HRP concentration, however, films loaded with 2% HRP demonstrated a smaller pore size distribution than films loaded with 0.5% HRP. The small pore population is more uniform. This increase in the observed homogeneity indicates an improvement in emulsion stability, and serves as an indication that HRP also acts as an effective surfactant which tends to be located at the interface between the aqueous and the organic phases, thus reducing their interfacial tension. Therefore, when the HRP concentration is increased, the coalescence of the aqueous domains (droplets) is slowed and results in a more homogenous pore population. Since these exemplary films are highly porous, having porosity of 85.4-88.6%, small microstructural changes may have a small effect on the HRP release profile.

Effect of the Polymer Concentration

As can be seen in FIG. 2B, showing the effect of the polymer concentration of the emulsion's organic phase on the HRP release profile, the burst release effect is attenuated from 65% to 47% when the polymer concentration is increased from 15% to 25% w/v. The increase in the polymer concentration of the organic phase results in a more hydrophobic polymeric porous film and therefore its water uptake rate is lowered, resulting in a lower burst release rate.

Other observed structural changes resulted from the increased polymer concentration, due to changes in the inverted emulsion properties. For example, when a relatively low polymer concentration of 15% w/v was used, only the small pore population was obtained in the resulting film, whereas all other studied formulations with higher polymer concentration exhibited dual pore size populations (see, FIGS. 3C-D and Table 2). As can be seen in FIGS. 3A-F and Table 2, the large pore size did not change to a great extent with the increase in the polymer concentration, while the small pore size decreased from 5.5 to 1.5 μm with the increase in polymer concentration from 15% to 25% w/v.

It is assumed that when the polymer concentration of the continuous organic phase is increased, the aqueous dispersed phase is actually exposed to higher shear forces and this decreases the size of the small aqueous domains and results in a smaller pore size and porosity. As a result, slower diffusion of the protein from the film is obtained and this probably also contributes to the decrease in the burst release for samples containing higher polymer concentrations.

Effect of the O:A Phase Ratio

As can be seen in FIG. 2C, showing the effect of the O:A phase ratio on the HRP release profile from the polymeric porous films, when the O:A phase ratio was increased from 2:1 to 8:1, the HRP burst release decreased from 58% to 48%. The release profile of all studied films in the O:A series exhibited very similar release profiles. As can be seen in FIGS. 3E-F and Table 2, a dual pore size population was observed for the studied samples, wherein the large pore population did not change and a decrease in the diameter of the small pores from 4.7 to 2.3 μm was obtained due to the increase in the O:A phase ratio. The reduction in the small pore size is attributed to the increase in the emulsion's viscosity, which enables the higher emulsion shear forces to reduce the size of the dispersed phase and therefore also the resulting pore size. It should be noted that accordingly, the porosity decreased from 92.5% to 76.7% when the O:A phase ratio increased from 2:1 to 8:1.

It is assumed that the combination of the relatively high porosity of the films (even at O:A=8:1) and the hydrophilic nature of HRP, contributed to the effective diffusion of HRP from the films in all studied formulations of this series.

Encapsulation Efficiency

The encapsulation efficiency values for all studied samples were measured and were found to be in the range of 83-90%. For example, for the series with a change in HRP concentration, samples loaded with 0.5, 1 and 2 w/w HRP exhibited encapsulation efficiency values of 89%, 87% and 86%, respectively. For the series with change in polymer concentration, samples loaded with 15.5%, 17.5% and 25% w/v polymer exhibited encapsulation efficiency values of 90%, 87% and 85%, respectively.

Hence, it is assumed that the differences in the release profiles of the various samples in each series correlate to changes in the relevant formulation parameter and not to differences in HRP concentration.

Effect of the Host Polymer on the Microstructure and HRP Release Profile:

The host polymer's parameters that were studied included the copolymer composition, namely the relative quantities of lactic and glycolic acid, and the initial average molecular weight. The effect of these parameters on the HRP release profile are presented in FIGS. 4A-B, and their effect on the film's microstructure are presented in FIGS. 5A-D and Table 2.

FIGS. 4A-B present comparative plots of cumulative release of HRP by percents as a function of time (in days) as measured from exemplary polymeric porous films, according to some embodiments of the present invention, demonstrating the effect of a change in the composition of the host copolymer compared to reference formulation A, wherein FIG. 4A presents the effect of the relative content of lactic and glycolic acid (solid rectangles denote 50/50 PDLGA, and solid triangles denote 75/25 PDLGA); and FIG. 4B presents the effect of the initial average molecular weight of the host polymer (solid diamonds denote 50 kDa, solid rectangles 83 kDa, and solid circles denotes 185 kDa).

FIGS. 5A-D presents SEM fractographs of exemplary polymeric porous films, according to some embodiments of the present invention, showing the effect on the microstructure of the films as a function of a change in the host copolymer composition parameters, wherein the effect of the relative content of lactic and glycolic acid is shown in FIGS. 5A-B; and the effect of the initial average molecular weight of the host polymer is shown in FIGS. 5C-D, and all films are made with 17.5% w/v containing 1% w/w HRP at a phase ratio of 4:1.

Effect of the Relative Content of Lactic and Glycolic Acid

As can be seen in FIGS. 5A-B and Table 2, when the copolymer composition was changed from 50/50 PDLGA to 75/25 PDLGA, an increase in the pore diameter of the small pore population was observed. The 75/25 PDLGA formulation contains more lactic acid groups in the copolymer than the 50/50 PDLGA, hence its emulsion's organic phase is therefore more hydrophobic and the resulting emulsion's interfacial tension is higher, lowering the emulsion's stability and increasing the pore size in the resulting polymeric porous films.

As can be seen in FIG. 4A, the change in microstructure due to the relative content of lactic and glycolic acid had a rather small effect on the HRP release profile. It is also noted that there is little difference in the burst release rates measured for the 75/25 PDLGA as compared to that of the 50/50 PDLGA based films, and after 3 days they exhibit the same sustained release profile.

Effect of the Initial Average Molecular Weight

The change in the initial average molecular weight of the 50/50 PDLGA porous films exhibited a notable effect on the HRP release profile as well as on the film's microstructure.

As can be seen in FIG. 4B, when the polymer's initial molecular weight was increased from 50 kDa o 183 kDa, the burst release decreased from 73% to 42% and the release rate increased, as discerned from the slope of the release curves.

The increase in the initial MW of the host polymer actually results in a more hydrophobic polymer due to a smaller quantity of end groups, therefore the water uptake rate of the resulting film is lowered, which is assumed to be the reason for the lower burst release.

As can be seen in (FIGS. 5C-D and Table 2, when a relatively low MW was used, the resulting film contained primarily small pore population, whereas the studied formulations with a higher MW exhibited dual pore size populations. In the latter, the large pore size did not change with the increase in the polymer concentration, while the small pore size decreased from 7.1 to 2.5 μm with the increase in the polymer's MW from 50 to 185 kDa.

When the polymer's MW is increased, the viscosity of the organic phase is also increased and the aqueous dispersed phase is actually exposed to higher shear forces. This outcome decreases the size of the aqueous small domains and results in a smaller pore size, resulting in slower diffusion of HRP from the film. This probably also contributes to the decrease in the burst release rates for film samples containing a higher MW.

Interestingly, when either the polymer concentration or the polymer's MW was increased, a transformation from a single to a dual pore size population was observed (seem FIG. 2B and FIG. 4B), which may be explained by the increase in the viscosity of the organic phase (due to a higher polymer concentration or higher MW) leading to slower heat transfer and therefore to a lower freezing rate of the inverted emulsion. As a result, some coalescence of small aqueous phase domains occurred during the flash-freeze and freeze-drying steps, ultimately leading to a dual pore size population.

Combined Effect of Parameters and Composite Film:

As demonstrated hereinabove, the HRP release profile from the exemplary polymeric porous films, according to some embodiments of the present invention, exhibited medium-to-high burst release rates followed by relatively high and sustained release rates, wherein most of the encapsulated HRP was released within 3 weeks.

Such profiles are suitable for various biomedical applications, however, in certain cases relatively low burst effects and lower release rates are needed, such as in prophylactic and chronic treatments. It is demonstrated herein that a decrease in the HRP concentration or increase in the host polymer's MW and concentration, and an increase in the O:A phase ratio, result in a decreased burst release and a more moderate sustained release profile (see, FIGS. 2A-C and FIGS. 4A-B).

Based on these findings, the combined effects of changes in two or three parameters on the HRP release profile and on the film's microstructure were investigated and the results are presented in FIGS. 6A-C and FIG. 7, respectively.

FIGS. 6A-C present comparative plots of cumulative release of HRP by percents as a function of time (in days) as measured from exemplary polymeric porous films, according to some embodiments of the present invention, demonstrating the effect of combined changes in the emulsion's formulation parameters compared to reference formulation A (marked by solid rectangles and having 17.5% w/v polymer, initial MW of 83 kDa, 1% w/w HRP and O:A=4:1), wherein FIG. 6A presents the effect of varying both the HRP concentration to 0.5% w/w HRP and varying the polymer concentration to 25% w/v (marked by solid diamonds), varying the initial MW to 185 kDa (marked by solid circles) and varying the O:A ratio to 8:1 (marked by solid triangles); FIG. 6B presents the effect of varying three parameters (0.5% w/w HRP, 25% w/v polymer, and O:A=8:1, marked by empty circles); and FIG. 6C presents the release profile from an exemplary composite "sandwich" film composed of a porous inner 50/50 PDLGA film (25% w/v polymer, MW of about 83 kDa, O:A=8:1 and 0.5% w/w HRP) and two external PDLLA layers (17.5% w/v polymer, MW of about 80 kDa, O:A=2:1, no HRP), marked by X-signs.

FIGS. 7A-E presents SEM fractographs of exemplary polymeric porous films, according to some embodiments of the present invention, showing the effect on the microstructure of the films as a function of a simultaneous change in several of the emulsion formulation's parameters, wherein FIG. 7A shown the microstructure of a film prepared from reference formulation A (50/50 PDLGA, 17.5% w/v polymer, MW=83 kDa, 1% w/w HRP, and O:A=4:1), FIG. 7B shown the microstructure of a formulation altered by 25% w/v polymer and 0.5% w/w HRP concentration, FIG. 7C shown the microstructure of a formulation altered by MW=185 kDa and 0.5% w/w HRP, FIG. 7D shown the microstructure of a formulation altered by O:A=8:1 and 0.5% w/w HRP, and FIG. 7E shown the microstructure of a formulation altered by 25% w/v polymer, O:A=8:1 and 0.5% w/w HRP.

In the three studied samples, having a simultaneous alteration of two emulsion parameters, the HRP concentration was reduced from 1% to 0.5% w/w (compared to reference sample A), and the second parameter was changed as follows:

Sample A: The polymer concentration of the organic phase was increased from 17.5% w/v (reference formulation A) to 25% w/v;

Sample B: The initial MW was increased from 83 kDa (reference formulation A) to 185 kDa; and Sample C: The O:A phase ratio was increased from 4:1 (reference formulation A) to 8:1.

As can be seen in FIG. 6A, all three exemplary films with a simultaneous change in two parameters exhibited a relatively low burst release of 15-20% and a prolonged sustained release which decreased with time. All three release profiles are similar and approximately 90% of the encapsulated HRP, serving as a model released drug, was released within 4 weeks.

The effect of the various parameters on the burst release rate was affected as follows:

(i) a decrease in the HRP concentration from 1% w/w to 0.5% w/w decreased the burst release from 57% to 37%;

(ii) an increase in the polymer concentration from 17.5% to 25% w/v decreased the burst release from 57% to 47%;

(iii) an increase in the initial MW from 83 to 185 kDa decreased the burst release from 57% to 42%; and (iv) an increase in the O:A phase ratio from 4:1 to 8:1 resulted in a decrease in the burst release from 57% to 48%.

In all the studied combinations, the effect of a simultaneous change in two parameters resulted in a decrease in the burst release (from 57% to 15-20%), which is more effective than the sum of the single effects. It is therefore suggested that these parameters have a synergistic effect on the release profile.

FIG. 6D presents the HRP release profile results obtained for a film made from an additional type of sample, Sample D, having a simultaneous change in three parameters (0.5% w/w HRP, 25% w/v polymer and O:A=8:1), compared to the HRP release profile obtained for a film made from reference formulation A.

Table 3 summarized the results obtained in the studies of the structural features of films with simultaneous changes in two or three parameters of the emulsion formulation.

TABLE 3

| Process parameters | Mean large pore diameter (μm) | Mean small pore diameter (μm) | Porosity |
|---|---|---|---|
| Reference formulation A | | | |
| 1% w/w HRP 50/50 PDLGA MW = 83 kDa 17.5% w/v polymer, O:A = 4:1 | 17.1 ± 2.7 | 4.3 ± 0.8 | 86.9 ± 2.6 |
| Sample A | | | |
| 0.5% w/w HRP 25% w/v polymer | 12.5 ± 1.8 | 2.1 ± 0.6 | 81.0 ± 1.7 |
| Sample B | | | |
| 0.5% w/w HRP MW = 185 kDa | 18.6 ± 3.4 | 2.8 ± 0.8 | 82.9 ± 1.1 |
| Sample C | | | |
| 0.5% w/w HRP O:A = 8:1 | 16.4 ± 2.2 | 3.6 ± 1.5 | 85.1 ± 1.3 |
| Sample D | | | |
| 0.5% w/w HRP 25% w/v polymer O:A = 8:1 | 12.4 ± 2.0 | 1.8 ± 0.7 | 76.9 ± 3.3 |

As can be seen in FIG. 6B, the HRP release profile from the film prepared with the emulsion formulation Sample D, exhibiting a change in three parameters, namely 0.5% w/w HRP, 25% w/v polymer and O:A=8:1 with respect to reference formulation A, is similar to that obtained for the film prepared with the emulsion formulation Sample B, exhibiting a change in two parameters, namely 0.5% w/w HRP and 25% w/v polymer with respect to reference formulation A, shown in FIG. 6A. The release profile of the film prepared with the emulsion formulation Sample D exhibited a burst release of 14% and a sustained release rate which decreases with time, but at a slower rate than that obtained for the film after a change in two parameters. After 4 weeks of incubation this film released 73% of the encapsulated HRP.

As can be seen in FIGS. 7A-E and Table 3, all samples with a change in two or three parameters exhibited a dual pore size population, with large pores in the range of 12.4-18.6 μm and small pores in the range of 1.8-3.6 μm, and porosity in the range of 81-85%, except for the film with a change in three parameters which exhibited a relatively low porosity of 76.9%. Although the small pore diameters of the films with a change in two and three parameters are smaller than that of the film made from reference formulation A (4.3 μm) and their porosities are lower than that of the film made from reference formulation A (86.9%), these changes in microstructure are probably not the main reason for the significant change in the HRP release profile.

It is suggested that the changes in the HRP burst release and continuous profile are attributed mainly to differences in the driving force for diffusion (which depend on the HRP concentration), hydrophilicity/hydrophobicity of the host polymer and its water uptake rate during the first period of exposure to the aqueous medium. It is further suggested that water uptake rates during the first period of exposure to the aqueous medium of the polymeric porous films, according to some embodiments of the present invention, are determined primarily by the initial MW of the host polymer and the polymer concentration in the organic phase of the inverted emulsion.

Composite "Sandwich" Film

The rationale for developing a composite "sandwich" film was the wish to combine the desired release profile with cell growth into the polymeric porous composite film. Since cell growth requires relatively large pores, and since relatively large pores typically do not achieve the desired HRP release profile, it was postulated that a film which contains at least two different layers, each providing highly desired attributes, will be able to serve the goals sought in tissue regeneration treatments.

The exemplary composite "sandwich" film, composed of three layers of polymeric porous films, is described hereinabove. The outer film layers contained pores of approximately 100 μm and did not contain any HRP.

As can be seen in FIG. 6C, a unique HRP release profile was obtained for this exemplary composite film, which exhibited a very low burst release (approximately 8%) and a constant release rate of 65% of the encapsulated HRP during the 4 weeks of the in vitro study, with a projected full release after 6 weeks of incubation. The outer layers served as barriers for HRP release which decreased the release rate and enabled a constant rate of sustained release. Furthermore, the relatively large pore-size of these layers is taken as suitable for tissue growth, providing diverse solutions for tissue-regeneration applications.

Biocompatibility of Polymeric Porous Films:

FIGS. 8A-C present micrographs of human gingival fibroblasts in culture, showing environmental effects coffered by the presence of a polymeric porous film, according to some embodiments of the present invention, made from reference formulation A having 1% w/w HRP (FIG. 8A); (b) a film made from reference formulation A without HRP (FIG. 8B); and a control experiment with no film in the environment of the sample (FIG. 8C, films appear in FIGS. 8A-B as a shadow).

As can be seen in FIG. 8C, human gingival fibroblasts (HGFs) reached confluence after 6-8 days in the absence of PDLGA films, and revealed a fibroblastic pattern. The gingival fibroblasts consist of elongated cells running as groups in different directions. No differences in cell shape or number were observed between the HRP-eluting films, as can be seen in FIG. 8A, and the non-eluting films, as seen in FIG. 8B.

As can be seen in FIGS. 8A-C, no significant differences in cell characteristics were observed between cells growing in the presence films eluding or not eluding HRP, and those growing with no film. Phase-contrast microscopy revealed viable fibroblasts attached to the upper surface of the films. Cells were also observed in close proximity to the outer borders of the films, and no specific orientation of the cells toward the surface of the films was observed. These results indicate that the films are biocompatible with HGFs.

Since most of HRP-release occurs during the first 3 days, no deterioration of the films or floating cells was observed during this time period. No changes in the HGF were observed even after 6-8 days.

Conclusions:

The effects of the emulsion's formulation and host polymer's characteristics on the film's microstructure and HRP release profile over 4 weeks were investigated. HGF adhesion to the films was also studied. Most films exhibited a HRP release profile of an initial burst release accompanied by a slowly-decreasing sustain release rate. A dual pore size population is characteristic of most films, with large 12-18 microns pores and small 1.5-7 microns pores, and porosity in the range of 76-92%.

An increase in the polymer concentration and its initial molecular weight, O:A phase ratio and lactic acid content, or a decrease in the HRP concentration, all resulted in a decreased burst effect and a more moderate sustained release profile. The HRP concentration significantly affected the HRP release profile, through the driving force for diffusion.

A decrease in the burst release and continuous release rate can also be achieved through the higher hydrophobic nature of the host polymer, i.e. by increasing the initial MW of the host polymer and its concentration in the organic phase of the emulsion. The former exhibited greater effectiveness than the latter.

The O:A phase ratio and copolymer composition only slightly affected the release profile. An increase in the polymer concentration and initial MW resulted in a smaller diameter of the small pores, due to the emulsion's higher viscosity and shear forces. However, these changes in microstructure only slightly affected the HRP release profile from the film.

A simultaneous change in two formulation parameters (compared to the reference formulation) resulted in a synergistic effect on the HRP release profile. Further decreases in the burst release and continuous release rate can be achieved when three formulation parameters are changed. A very low burst release and continuous release at a constant rate can also be achieved when a composite film is used.

The HGFs exhibited a typical growth and shape pattern in the presence of both HRP-eluting and non-eluting PDLGA films. The studied films are thus biocompatible and can be used in a controlled-release system as bioactive agents for tissue-regeneration applications.

It has been demonstrated that appropriate selection of the formulation's parameters can yield unique, highly porous films with adjustable protein-release behavior which can serve as scaffolds for bioactive agents in tissue-regeneration applications.

Example 2

Emulsion's Physical and Chemical Parameters for Controlling Drag-Release Profile The example focuses on the nanostructure of drug-eluting polymeric porous films, according to some embodiments of the present invention, and its effect on the drug release profile of both hydrophilic and hydrophobic drugs. Fine controlled nanostructuring was obtained using both the dispersion and the condensation methods of emulsion processing. Dispersion nanostructuring was achieved through homogenization rate, whereas condensation nanostructuring was achieved mainly by using different stabilizing surfactants, but also through changes in the emulsion formulations parameters, such as the organic/aqueous (O:A) phase ratio and copolymer composition.

Drug-eluting nanostructured polymeric porous films, according to some embodiments of the present invention, loaded with water-insoluble drugs as well as films loaded with water-soluble drugs were studied.

The water-insoluble drugs used in the example presented herein were the antiproliferative agents paclitaxel and Farnesylthiosalicylate (FTS). Paclitaxel is a lipophilic molecule derived from the Pacific yew tree *Taxus brevifolia*. Paclitaxel inhibits cell division and the development of new blood vessels, and is therefore effective for the treatment of cancer as well as for preventing restenosis; however, this drug is potentially cytotoxic and can therefore be delivered only in relatively small doses. FTS (Salirasib) is a specific nontoxic drug that acts as a Ras antagonist and has a mild hydrophobic nature. The nanostructured films described herein, loaded with antiproliferative agents, can thus be used for local cancer treatment as well as in stent coatings for inhibition of in-stent restenosis.

The water-soluble drugs employed in the example presented herein were the antibiotics ceftazidime hydrate and mafenide acetate. The nanostructured films loaded with antibiotic drugs can thus be used, among others, as coatings for fracture fixation devices, treatment of periodontal diseases, as well as wound and burn dressings.

Water-soluble drugs (antibiotic agents) were incorporated into the aqueous phase, whereas water-insoluble drugs (antiproliferative agents) were incorporated into the organic phase.

An emulsion formulation characterized by a polymer concentration of 17.5% w/v 50:50 PDLGA in the organic solution, an initial MW of about 83 kDa, and an organic to aqueous (O:A) phase ratio of 8:1 v/v, homogenized at a rate of 16000 rpm, was used as a reference formulation, denoted reference formulation B. Other formulations included variations in polymer concentration, homogenization rate, O:A phase ratio, and copolymer composition, as well as various surfactants.

This example enables the elucidation of the process-structure effects of the drug-eluting systems, according to some embodiments of the present invention, as well as how a finer structure can be obtained and converted from microstructured to nanostructured porous films. Other aspects focused on the effect of structuring on the release profile of both water-soluble and water-insoluble drugs.

Effect of the Emulsion's Preparation Parameters on the Polymeric Porous Film

An emulsion homogenization (mixing) duration of 120 seconds was chosen for all samples. Other emulsion formulation parameters included lactic acid contents in the copolymer in the range of 50-100%, O:A phase ratio in the range of 4:1-8:1, and homogenization rate in the range of 16000-28000 rpm. These values enabled obtaining stable emulsions in all studied formulations. The resulting films' thickness were in the range of 100-300 µm and the porous structure contained round-shaped pores in all films, usually within the 0.4-20 µm range, with a porosity of 65-90%. The structure was uniform in all samples, probably due to rapid quenching of the emulsion, which enabled preservation of the microstructure.

Examples for the effects of the above-mentioned emulsion parameters on the film microstructure are presented in FIG. 1.

FIGS. 9A-D present SEM fractographs of polymeric porous films, according to some embodiments of the present invention, showing the effect of changes in certain formulation parameters on the structure, wherein FIG. 9A presents the film obtained from reference formulation B (17.5% w/v of 50:50 PDLGA copolymer, O:A phase ratio of 8:1 and homogenization rate of 16000 rpm), FIG. 9B presents the film obtained from copolymer modified to PDLLA, FIG. 9C presents the film obtained from a formulation modified to O:A ratio of 4:1, and FIG. 9D presents the film obtained from modified reference formulation B homogenized at a rate of 28000 rpm.

As can be seen in FIGS. 9A and 9B, an increase in the lactic acid content of the PDLGA copolymer from 50% to 100% resulted in a notable increase in the pore size, from 3.1±1.5 µm to 18.4±9.9 µm respectively. Lactic acid is more hydrophobic than glycolic acid, hence, a higher lactic acid content in the emulsion's organic phase changes the emulsion's hydrophobic-hydrophilic balance. Higher lactic acid content in the host polymer decreases the surface tension of the organic phase, i.e., increases the interfacial tension between the water and the organic phase, resulting in lower emulsion stability. The dispersed droplets tend to either aggregate irreversibly or accumulate at an interface in order to reduce the interfacial energy. Higher lactic acid content, therefore, results in the creation of larger pores.

As can be seen in FIGS. 9A and 9C, modifications of the emulsion's O:A phase ratio affected the porosity, but had almost no effect on the pore size. Relatively low O:A phase ratios, such as 4:1, are associated with a higher volume fraction of pores, as seen in FIG. 9C, and connectivity between pores, whereas higher O:A phase ratios are associated with thicker polymer walls (between pores) and a larger portion of pores that become isolated, as seen in FIG. 9A.

Figure 2:
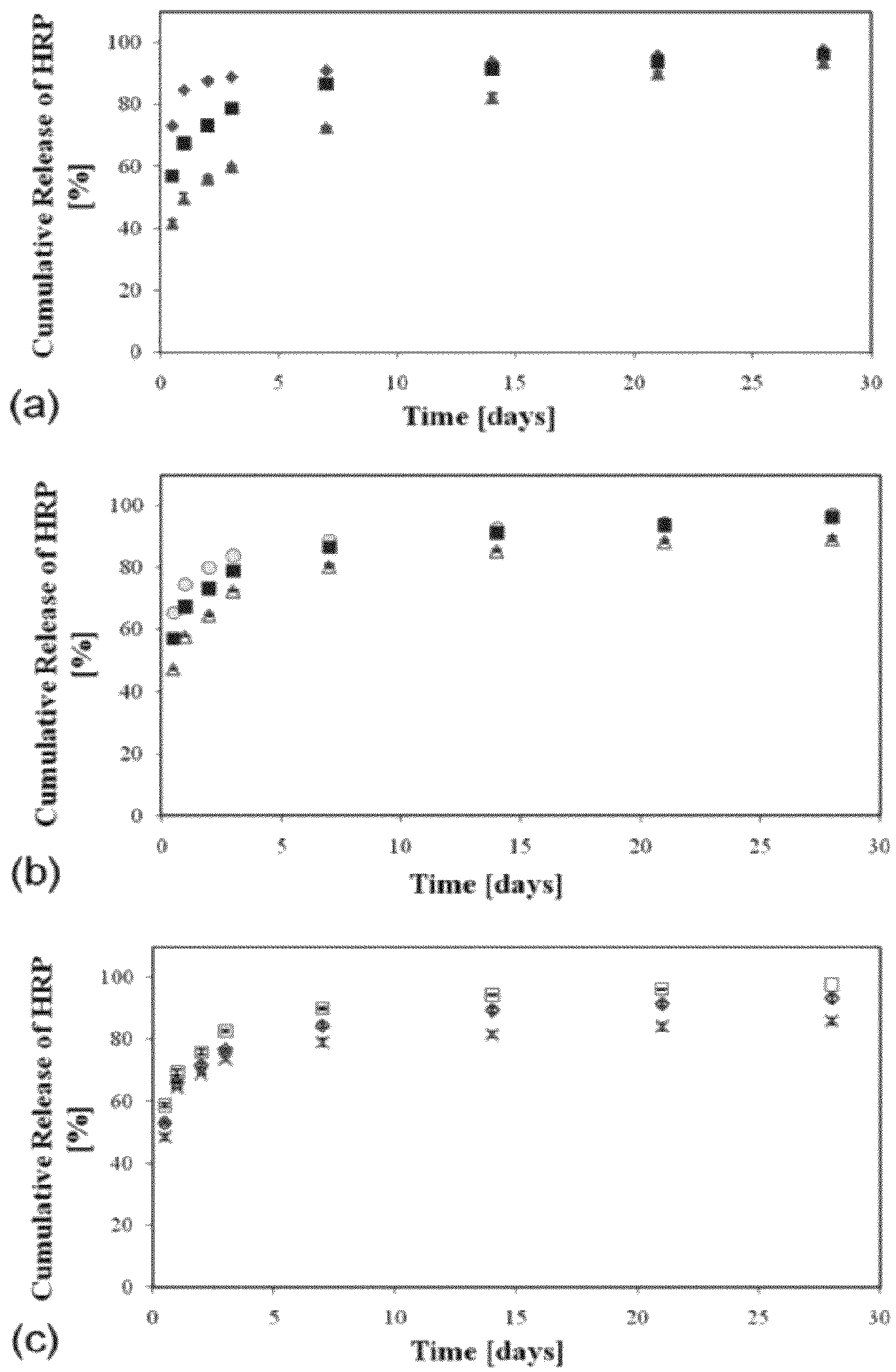

As can be seen in FIGS. 9A and 9D, the homogenization rate affects the mean pore diameter; an increase in the homogenization rate from 16000 to 28000 rpm resulted in a decrease in pore size from 3.1±1.5 µm, as seen in FIG. 9A, to 2.1±0.6 µm, as seen in FIG. 9D, due to higher fragmentation energy which increases the shearing rate, producing finely dispersed water droplets.

It is noted herein that the polymer's concentration in the organic phase did not exhibit a considerable effect on the film's structure, although it was generally limited to the range of 12.5-22.5% w/v.

Effect of the Surfactant on the Polymeric Porous Film

According to Bancroft's rule, which states that "The phase in which an emulsifier is more soluble constitutes the continuous phase", a direct O:A emulsion becomes stabilized with a water-soluble surfactant, whereas an inverted A:O emulsion is more easily obtained with an oil-soluble surfactant.

Various surface-active materials (surfactants) with different chemical properties were tested in order to reduce the pore diameter to a nanoscale and elucidate the effects of nanostructuring on the drug release profile from the films. Surfactants generally tend to be located between the aqueous and organic phases of the emulsion, which decreases the interfacial tension and thus enhances the thermodynamic stability of the emulsion. More hydrophobic surfactants were added to the organic phase prior to emulsification, whereas more hydrophilic surfactants were added to the aqueous phase.

The effect of surfactant incorporation on the pore size and distribution of the films obtained by reference formulation B, homogenized at a rate of 28000 rpm for 120 seconds, is summarized in Table 4.

Table 4 presents the effect of the surfactant on the film's mean pore diameter.

TABLE 4

| Surfactant (5%) | Mean pore diameter ± SD (μm) |
|---|---|
| Pluronic L-121 (Hydrophobic) | 2.1 ± 0.7 |
| Span 80 (Hydrophobic) | 1.5 ± 0.4 |
| BSA (Hydrophilic) | 0.6 ± 0.2 |
| PVA (Hydrophilic) | 1.8 ± 0.7 |
| HRP (Hydrophilic) | 0.4 ± 0.1 |

As can be seen in Table 4, although incorporation of more hydrophobic surfactants, such as Pluronic L-121 and Span 80, resulted in some decrease in mean pore size, from 2.4 μm to 2.1 μm and 1.5 μm, respectively, the stability of the emulsion has decreased. In contrast, incorporation of the high molecular weight and more hydrophilic surfactants (BSA, HRP, and PVA) had stabilizing effects, and the protein surfactants HRP and BSA were the most effective in reducing pore size. Both HRP and BSA yielded nanoscale pore diameters of less than 1 μm. Incorporating HRP resulted in an emulsion with two pore sizes, whereas BSA produced a very homogeneous structure with a single pore size population. When smaller concentrations of these surfactants were added, their effectiveness was reduced, indicating dose response behavior.

Controlled Release of Hydrophobic and Hydrophilic Bioactive Agents:

Two hydrophobic and two hydrophilic drugs were chosen for investigating the effect of the porous nanostructure on their controlled release. The antiproliferative agents paclitaxel and FTS were chosen as the hydrophobic drugs and mafenide acetate and ceftazidime pentahydrate as the hydrophilic drugs. All specimens were comprised of a 50:50 PDLGA, 17.5% w/v polymer concentration and stirring duration of 120 seconds. A phase ratio O:A of 4:1 was used for the hydrophobic drugs, whereas a 6:1 O:A phase ratio was used for the hydrophilic drugs.

Small drug concentrations (1.42% in case of hydrophobic drugs and 2% in case of hydrophilic drugs) were chosen to be incorporated in the film to suite the quantities that are needed for specific applications, namely the treatment of cancer and preventing restenosis using antiproliferative agents, and combat infections using antibiotic drugs.

Structuring effects were created by changing the homogenization rate (the "dispersion" method) or by using surfactants (the "condensation" method) and the effect of the structure on the drug release profile was studied. The characteristic structural features (mean pore diameter and porosity) as well as the drug encapsulation efficiency of all studied samples are presented in Table 5.

TABLE 5

| Drug loaded [% w/w] | Surfactant [% w/v] | Homogenization rate [rpm] | Mean pore diameter [μm] | Porosity [%] | Encapsulation efficiency [%] |
|---|---|---|---|---|---|
| FTS [1.42% w/w] | — | 28 000 | 2.4 ± 0.8 | 88.9 ± 1.9 | 83.1 ± 4.0 |
| | BSA (5%) | 28 000 | 0.6 ± 0.2 | 81.4 ± 2.5 | 80.0 ± 6.0 |
| | HRP (5%) | 28 000 | 0.4 ± 0.1 | 69.5 ± 2.1 | 78.3 ± 2.8 |
| | — | 14 000 | 3.9 ± 1.7 | 81.1 ± 2.0 | 65.5 ± 2.1 |
| | BSA (5%) | 14 000 | 1.3 ± 0.3 | 78.9 ± 3.3 | 60.7 ± 2.4 |
| Paclitaxel [1.42%] | — | 28 000 | 2.6 ± 0.8 | 81.5 ± 3.8 | 52.8 ± 0.6 |
| | BSA (5%) | 28 000 | 0.6 ± 0.1 | 74.8 ± 3.2 | 35.6 ± 2.9 |
| Mafenide acetate [2%] | — | 28 000 | 1.1 ± 0.3 | 88.1 ± 1.2 | 71.3 ± 0.5 |
| | BSA (1%) | 28 000 | 0.8 ± 0.2 | 81.7 ± 2.5 | 78.1 ± 2.1 |
| | — | 14 000 | 2.2 ± 0.9 | 81.9 ± 2.6 | 69.6 ± 1.0 |
| | BSA (1%) | 14 000 | 1.9 ± 0.5 | 83.7 ± 2.4 | 74.6 ± 4.2 |
| Ceftazidime hydrate [2 | — | 28 000 | 1.1 ± 0.4 | 77.6 ± 2.2 | 37.0 ± 1.9 |
| | BSA (1%) | 28 000 | 0.7 ± 0.2 | 75.6 ± 0.5 | 50.7 ± 0.5 |
| | — | 14 000 | 1.8 ± 0.7 | 80.5 ± 3.0 | 41.7 ± 1.6 |
| | BSA (1%) | 14 000 | 1.5 ± 0.5 | 75.4 ± 0.5 | 58.4 ± 2.3 |

The structures of the FTS-loaded polymeric porous films are presented in FIGS. 10A-E and the corresponding FTS-release profiles are presented in FIGS. 11A-B.

FIGS. 10A-E present SEM fractographs of FTS-loaded polymeric porous films, according to some embodiments of the present invention, showing the effect of surfactants on the structure, wherein FIG. 10A presents the film obtained from reference formulation B (17.5% w/v of 50:50 PDLGA copolymer, O:A phase ratio of 4:1 and homogenization rate of 28000 rpm) with 1.42% w/w FTS and no surfactant, FIG. 10B presents the film obtained from an emulsion similar to that presented in FIG. 10A but having 5% w/v BSA, FIG. 10C presents the film obtained from an emulsion similar to that presented in FIG. 10A but having 5% w/v HRP, FIG. 10D presents the film obtained from an emulsion similar to that presented in FIG. 10A but homogenized at a rate of 14000 rpm, and FIG. 10E presents the film obtained from an emulsion similar to that presented in FIG. 10A but having 5% w/v BSA and homogenized at a rate of 14000 rpm.

As can be seen in FIGS. 10A-E and Table 5, both an increase in the stirring rate and incorporation of an effective surfactant (BSA or HRP) resulted in a finer microstructure. A combination of both changes resulted in pores with a very small diameter of less than 1 μm, whereas incorporation of BSA resulted in a uniform fine structure with pores of 0.6 μm, and incorporation of HRP also resulted in a fine structure (mean pore size of 0.4 μm), however some of the droplets coalesced to form large pores.

FIGS. 11A-B present comparative plots of cumulative release of FTS by percents as a function of time (in days) as measured from exemplary 50:50 PDLGA polymeric porous films, according to some embodiments of the present invention, demonstrating the effect of surfactant incorporation in the emulsion's formulation (FIG. 11A) and the effect of homogenization rate and BSA as surfactant (FIG. 11B), wherein triangles denote reference formulation B without surfactant and homogenized at 28000 rpm, rectangles denote the same with 5% w/v BSA, circles denote the same with 5% w/v HRP, diamonds denote the same without surfactant and homogenized at 14000 rpm, and X-signs denote the same with 5% w/v BSA and homogenized at 14000 rpm.

As can be seen in FIGS. 11A-B, the nanostructuring resulted in a significant effect on the FTS-release profile, whereas films containing BSA, which yielded homogeneous nanometric pore diameters, presented a significant increase in burst release from 12% to 59% and the rate of sustained release during the first 3 weeks increased to a small extent. These results can be explained by the fact that the decrease in pore size increases the surface area for diffusion, causing faster release of the drug from the device. The burst release and release rate of FTS from films containing HRP were higher than from the films with no surfactants but lower than from films containing BSA. This may be explained by the fact that HRP produced two pore size populations (see, FIG. 10C). A relatively large surface area for diffusion is thus an effective tool for increasing the rate of a hydrophobic drug's diffusion from our porous systems.

The effect of the homogenization rate on the FTS-release profile for both types of films, with and without BSA as surfactant, is presented in FIG. 11B. In both cases, a decrease in the homogenization rate resulted in some decrease in the burst release and drug release rate, mainly due to the larger pore size obtained when a low homogenization rate was used (see, FIG. 10 and Table 5). The lower encapsulation efficiency, seen in Table 5, may have also contributed to the lower burst release and lower rate of FTS release from the porous films.

It is noted that versatile FTS-release profiles of the hydrophobic FTS molecules from highly porous bioresorbable polymeric films, according to some embodiments of the present invention, can be achieved using structuring effects, by choosing the appropriate homogenization rate and surfactants. Relatively low burst release rates and relatively low sustained release rates can be achieved with a coarse microstructure, obtained when a low homogenization rate is used during the emulsion processing step. Such drug-release profiles are desirable for local treatments of diseases such as cancer.

In contrast, higher burst release values and higher sustained release rates can be achieved with a fine nanostructure, obtained when a high homogenization rate is used and surfactants are incorporated into the emulsion. Such release kinetics suitable for topical applications to fight acute infections.

The release profiles of the antiproliferative agent paclitaxel from the polymeric porous films and their microstructure are presented in FIGS. 12A-C.

FIGS. 12A-C present a comparative plot of the release profile of paclitaxel polymeric porous films, wherein triangles denote films made from reference formulation B containing 1.42% w/w paclitaxel, and homogenized at 28000 rpm with no surfactant, and rectangles denote the same but with 5% w/v BSA (FIG. 12A), and present SEM fractographs of a film made from reference formulation B containing 1.42% w/w paclitaxel with no surfactant (FIG. 12B), and a SEM fractographs of the same but with 5% w/v BSA.

As can be seen in FIGS. 12A-C, the results show that although a fine nanostructure was obtained for BSA-containing films (0.6 μm, see FIG. 12C), it yielded only a slight increase in the paclitaxel release rate and did not significantly affect the burst effect (see, FIG. 12A). The relatively low paclitaxel release rate is due to its highly hydrophobic nature, and it may also form specific interactions with the PDLGA matrix. It should also be noted that the encapsulation efficiency of BSA-containing films (35%) was lower than that of the reference film (53%). If the encapsulation efficiency of both films were similar, paclitaxel's release rate from BSA-containing samples would probably be even higher.

Films loaded with the antibiotic drugs mafenide acetate and ceftazidime pentahydrate were also studied in order to elucidate the effects of microstructure on the release profile of hydrophilic drugs from our systems. The antibiotic drug-release profiles are presented in FIGS. 13A-B and the microstructures of mafenide-loaded films are presented in FIGS. 14A-D.

FIGS. 13A-B present comparative antibiotic drug-release plots, showing the effect of BSA as surfactant and homogenization rate on the release profile from polymeric porous films containing 17.5% w/v 50:50 PDLGA polymer, O:A=6:1, 2% w/v drug concentration, and homogenized at 28000 rpm, wherein results obtained for films loaded with mafenide acetate are shown in FIG. 13A, and results obtained for films loaded with ceftazidime pentahydrate are shown in FIG. 13B, whereas triangles denote a reference sample with no surfactant, diamonds denote the same homogenized at 14000 rpm, rectangles denote the same with 1% w/v BSA, and circles denote the same with 1% w/v BSA homogenized at 14000 rpm.

FIGS. 14A-D present SEM fractographs showing the effects of BSA as surfactant and homogenization rate on the microstructure of films made from an emulsion formulation containing 17.5% w/v 50:50 PDLGA polymer, O:A=6:1, 2% w/v mafenide acetate, and homogenized at 28000 rpm with no surfactant (FIG. 14A), the same with 1% w/v BSA (FIG. 14B), the same homogenized at 14000 rpm (FIG. 14C), and the same with 1% w/v BSA homogenized at 14000 rpm (FIG. 14D).

Figure 13:
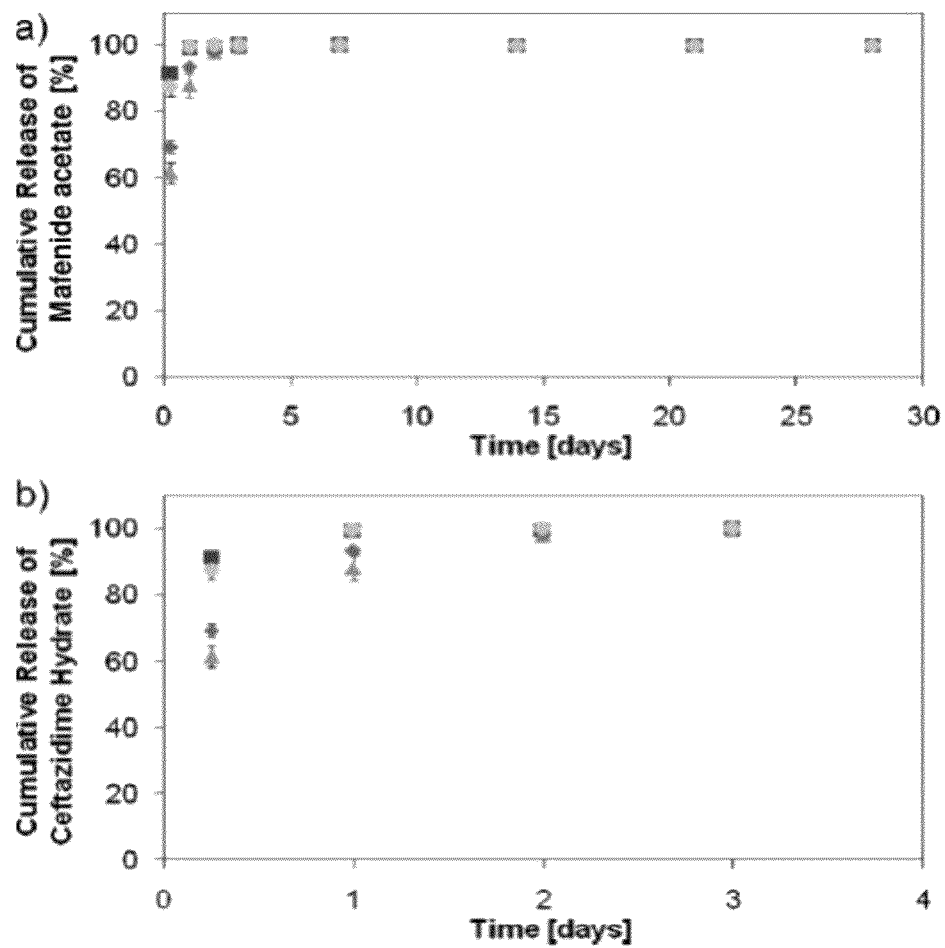
Figure 14:
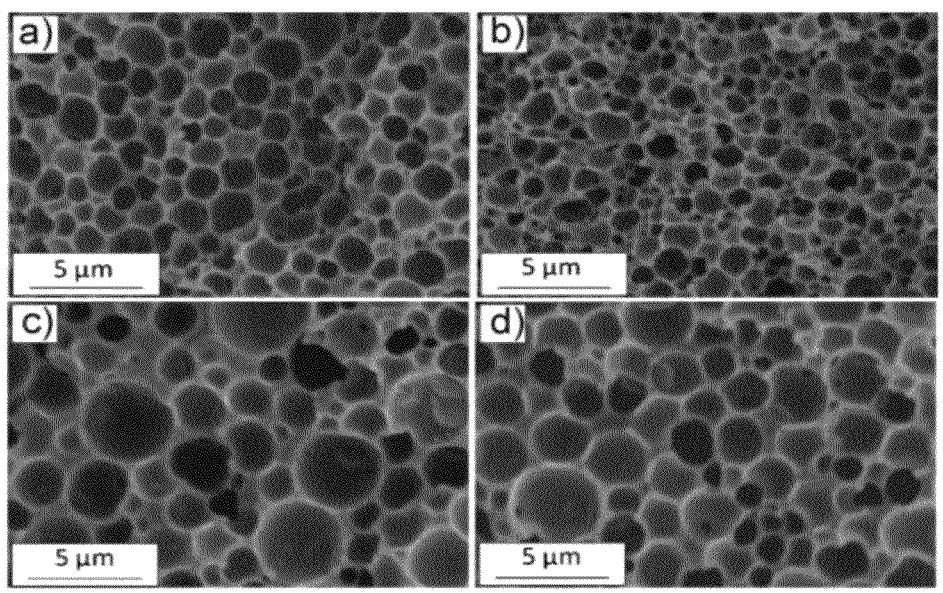

As can be seen in FIGS. 13 and 14, the films which were loaded with water-soluble drugs, 1% BSA was sufficient for optimal stabilization of the emulsion. The presence of BSA in these films was therefore less effective in structuring into fine nanostructures than in films loaded with hydrophobic drugs, where 5% BSA was added.

In general, both hydrophilic drugs exhibited relatively high burst effects (45-68%) and high release rates. Mafenide acetate was almost fully released after 21 days and ceftazidime hydrate was almost fully released within 3 days. In both cases, a higher homogenization rate and incorporation of BSA as surfactant resulted in a finer nanostructure, leading to a higher burst release and higher release rate. The surfactant had a more significant effect on the release profile than the process kinetics. It is therefore suggested that the incorporation of a hydrophilic surfactant in a system containing a hydrophilic drug, enhances the hydrophilic nature of the entire system and therefore facilitates diffusion of the drug to the surroundings. The release profiles from BSA-containing systems are fast, whereas the release profiles of the antibiotic drugs from systems with coarser structures (especially those obtained using a low homogenization rate) are more favorable.

Release profiles from finer porous films exhibited burst release values of 40-60% and more moderate sustained release profiles than coarser structures. Such burst release values are desirable for many antibiotic release applications, where an acute infection has already set in. If a specific application requires a lower burst release, such as in prophylactic treatment applications, it is recommended to choose emulsion formulations with higher O:A phase ratios, higher copolymer lactic acid content, or less hydrophilic drugs.

CONCLUSIONS

The results clearly demonstrate that nanostructured porous films (resulting from nanoemulsions) are desirable for systems loaded with hydrophobic drugs and less desirable for systems loaded with hydrophilic drugs. This is related to the fact that the main mechanism of release is diffusion of the drug within an aqueous medium. Nanostructuring in the systems described herein enables a larger surface area for diffusion and therefore a faster release rate of hydrophobic molecules. A delicate balance between the various formulation parameters is desired in order to obtain fine and stable inverted nanoemulsions.

BSA and HRP were found to be the most effective surfactants in forming the polymeric porous films, according to some embodiments of the present invention, and contribute to the formation of smaller pores of less than 1 μm.

Understanding the relationships between processing, structure, and the resulting controlled-drug release behavior can advance the field of active implants by enabling their adaptation to a wide variety of applications.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric system comprising a first polymeric porous film having incorporated therein a bioactive agent,
said first polymeric porous film being prepared by freeze-drying a water-in-oil emulsion in which:
a polymer forming said first polymeric porous film is PDLGA;
a lactic acid to glycolic acid ratio of said PDLGA is lower than 60:40;
a concentration of said PDLGA is higher than 17% w/v;
an initial molecular weight of said PDLGA is higher than about 100 kDa;
said emulsion comprises a high molecular weight amphiphilic or hydrophilic surfactant;
a concentration of said surfactant is higher than 3%;
said emulsion is prepared at a homogenization rate of more than 20000 rpm; and
an oil phase to aqueous phase ratio (O:A) in said emulsion is lower than 5:1;
whereas at least 20% of said bioactive agent are released within 6 hours of contacting the system with a physiological medium.

2. The polymeric system of claim 1, wherein said bioactive agent is selected from the group consisting of an antibiotic agent, an analgesic agent and a hemostatic agent.

3. The polymeric system of claim 1, wherein said polymeric film is prepared from an emulsion in which:
said lactic acid to glycolic acid ratio of said PDLGA is 50:50;
said concentration of said PDLGA is 25% w/v;
said initial molecular weight of said PDLGA is 185 kDa;
said emulsion comprises a protein-type surfactant;
said concentration of said surfactant is 5%;
said emulsion is prepared at a homogenization rate of 28000 rpm; and
said oil phase to aqueous phase ratio (O:A) in said emulsion is 4:1.

4. The polymeric system of claim 1, further comprising a second polymeric film onto which said first polymeric porous film is applied.

5. The polymeric system of claim 4, further comprising a third polymeric film applied on said first polymeric porous film.

6. A polymeric system comprising a first polymeric porous film having incorporated therein a bioactive agent, said first polymeric porous film being prepared by freeze-drying a water-in-oil emulsion in which:
said polymer forming said first polymeric porous film is PDLGA;
a lactic acid to glycolic acid ratio of said PDLGA is higher than 60:40;
a concentration of said PDLGA is lower than 17% w/v;
an initial molecular weight of said PDLGA is lower than about 100 kDa;
said emulsion comprises a low molecular weight hydrophobic surfactant;
a concentration of said surfactant is less than 3%;
said emulsion is prepared at a homogenization rate of less than 20000 rpm; and
an oil phase to aqueous phase ratio (O:A) in said emulsion is higher than 5:1;
whereas less than 20% of said bioactive agent are released within 6 hours of contacting the system with a physiological medium.

7. The polymeric system of claim 6, wherein said polymeric film is prepared from an emulsion comprising in which:
said lactic acid to glycolic acid ratio of said PDLGA is 75:25;
said concentration of said PDLGA is 15% w/v;
said initial molecular weight of said PDLGA is 50 kDa;
said emulsion is prepared at a homogenization rate of 14000 rpm; and
said oil phase to aqueous phase ratio (O:A) in said emulsion is 8:1.

8. The polymeric system of claim 6, further comprising a second polymeric film onto which said first polymeric porous film is applied.

9. The polymeric system of claim 8, wherein said second polymeric film comprises a wettable polymer.

10. The polymeric system of claim 9, wherein said wettable polymer is a wettable biodegradable polymer.

11. The polymeric system of claim 10, wherein said wettable biodegradable polymer is selected from the group consisting of collagen, chitosan, cellulosic-base polymer and a polyethylene glycol.

12. The polymeric system of claim 6, further comprising a third polymeric film applied on said first polymeric porous film.

13. The polymeric system of claim 1, being consisted of said first polymeric porous film having said bioactive agent incorporated therein.

14. A medical device comprising the polymeric system of claim 1.

15. The medical device of claim 14, being selected from the group consisting of a wound dressing and a skin patch.

16. A process of preparing the polymeric system of claim 1, the process comprising:
casting a first layer of a water-in-oil emulsion in or on a mold;
freeze-drying said first layer, thereby obtaining said first polymeric porous film; and
detaching said first polymeric porous film from said mold to thereby obtain the system.

17. The process of claim 16, further comprising:
prior to said detaching said first polymeric porous film, casting a second layer of a second water-in-oil emulsion on said first layer;
freeze-drying said first layer and said second layer, thereby obtaining a second polymeric porous film applied onto said first polymeric porous film; and
detaching said first polymeric porous film from said mold to thereby obtain composite structure which comprises said first polymeric porous film and which further comprises a second polymeric porous film onto which said first polymeric porous film is applied;
or subsequent to said detaching said first polymeric porous film, casting a second layer of a second water-in-oil emulsion on said first polymeric porous film;

freeze-drying said second layer, to thereby obtain composite structure which comprises said first polymeric porous film and which further comprises a second polymeric porous film onto which said first polymeric porous film is applied.

18. The process of claim 16, further comprising, subsequent to said detaching said first polymeric porous film, contacting said first polymeric porous film with a second water-in-oil emulsion said to thereby form a second layer of said second emulsion one side of said first polymeric porous film and a third layer of said second emulsion the other side of said first polymeric porous film;

freeze-drying said second layer and said third layer, to thereby obtain composite structure which comprises said first polymeric porous film and which further comprises a second polymeric porous film applied onto said first polymeric porous film and a third polymeric porous film applied onto said first polymeric porous film.

19. The process of claim 16, further comprising:

prior to said detaching said first polymeric porous film, casting a second layer which comprises a biodegradable and wettable polymer on said first layer;

freeze-drying said first layer and said second layer, thereby obtaining a biodegradable and wettable polymeric film applied onto said first polymeric porous film; and detaching said first polymeric porous film from said mold to thereby obtain composite structure which comprises said first polymeric porous film and which further comprises a biodegradable and wettable polymeric film applied onto said first polymeric porous film;

or subsequent to said detaching said first polymeric porous film, casting a second layer which comprises a biodegradable and wettable polymer on said first polymeric porous film;

freeze-drying said second layer, to thereby obtain composite structure which comprises said first polymeric porous film and which further comprises a biodegradable and wettable polymeric film applied onto said first polymeric porous film.

20. The polymeric system of claim 4, wherein said second polymeric film comprises a wettable polymer.

21. The polymeric system of claim 20, wherein said wettable polymer is a wettable biodegradable polymer.

22. The polymeric system of claim 21, wherein said wettable biodegradable polymer is selected from the group consisting of collagen, chitosan, cellulosic-base polymer and a polyethylene glycol.

23. The polymeric system of claim 6, said bioactive agent is selected from the group consisting of a proliferative agent, an antiproliferative agent, an analgesic agent, an anticancer agent, a vitamins and a hormones.

24. The polymeric system of claim 8, further comprising a third polymeric film applied on said first polymeric porous film.

25. The polymeric system of claim 6, being consisted of said first polymeric porous film having said bioactive agent incorporated therein.

26. A polymeric system comprising a first polymeric porous film having incorporated therein a bioactive agent, and a second polymeric film onto which said first polymeric porous film is applied, wherein said first polymeric porous film is prepared by freeze-drying a water-in-oil emulsion and said second polymeric film comprises a wettable polymer.

27. The polymeric system of claim 26, wherein said wettable polymer is a wettable biodegradable polymer.

28. The polymeric system of claim 27, wherein said wettable biodegradable polymer is selected from the group consisting of collagen, chitosan, cellulosic-base polymer and a polyethylene glycol.

29. The polymeric system of claim 26, wherein said first polymeric porous film is prepared by freeze-drying a water-in-oil emulsion in which:

a polymer is PDLGA;

a lactic acid to glycolic acid ratio of said PDLGA is lower than 60:40;

a concentration of said PDLGA is higher than 17% w/v;

an initial molecular weight of said PDLGA is higher than about 100 kDa;

said emulsion comprises a high molecular weight amphiphilic or hydrophilic surfactant;

a concentration of said surfactant is higher than 3%;

said emulsion is prepared at a homogenization rate of more than 20000 rpm; and an oil phase to aqueous phase ratio (O:A) in said emulsion is lower than 5:1;

whereas at least 20% of said bioactive agent are released within 6 hours of contacting the system with a physiological medium.

30. The polymeric system of claim 26, wherein said first polymeric porous film is prepared by freeze-drying a water-in-oil emulsion in which:

a polymer is PDLGA;

a lactic acid to glycolic acid ratio of said PDLGA is higher than 60:40;

a concentration of said PDLGA is lower than 17% w/v;

an initial molecular weight of said PDLGA is lower than about 100 kDa;

said emulsion comprises a low molecular weight hydrophobic surfactant;

a concentration of said surfactant is less than 3%;

said emulsion is prepared at a homogenization rate of less than 20000 rpm; and an oil phase to aqueous phase ratio (O:A) in said emulsion is higher than 5:1;

whereas less than 20% of said bioactive agent are released within 6 hours of contacting the system with a physiological medium.

31. The polymeric system of claim 26, further comprising a third polymeric film applied on said first polymeric porous film.

32. A polymeric system comprising a first polymeric porous film having incorporated therein a bioactive agent, wherein a mean pore diameter of said first polymeric porous film is lower than 1 micron, said first polymeric porous film is prepared by freeze-drying a water-in-oil emulsion in which:

a polymer is PDLGA;

a lactic acid to glycolic acid ratio of said PDLGA is lower than 60:40;

a concentration of said PDLGA is higher than 17% w/v;

an initial molecular weight of said PDLGA is higher than about 100 kDa; and said emulsion is prepared at a homogenization rate of more than 20000 rpm;

whereas at least 20% of said bioactive agent are released within 6 hours of contacting the system with a physiological medium.

33. The polymeric system of claim 32, wherein said polymeric film is prepared from an emulsion in which:

said emulsion comprises a high molecular weight amphiphilic or hydrophilic surfactant;

a concentration of said surfactant is higher than 3%; and
an oil phase to aqueous phase ratio (O:A) in said emulsion is lower than 5:1.

34. The polymeric system of claim 32, further comprising a second polymeric film onto which said first polymeric porous film is applied.

35. The polymeric system of claim 34, wherein said second polymeric film comprises a wettable polymer.

36. The polymeric system of claim 35, wherein said wettable polymer is a wettable biodegradable polymer.

37. The polymeric system of claim 36, wherein said wettable biodegradable polymer is selected from the group consisting of collagen, chitosan, cellulosic-base polymer and a polyethylene glycol.

38. The polymeric system of claim 34, further comprising a third polymeric film applied on said first polymeric porous film.

39. The polymeric system of claim 33, being consisted of said first polymeric porous film having said bioactive agent incorporated therein.

40. A medical device comprising the polymeric system of claim 6.

41. The medical device of claim 40, being selected from the group consisting of a sustained release drug delivery system, a wound dressing and a skin patch, a tissue regeneration device and a directed antitumor device.

* * * * *